(12) United States Patent
Han et al.

(10) Patent No.: US 9,312,497 B2
(45) Date of Patent: Apr. 12, 2016

(54) HETEROCYCLIC COMPOUND, ORGANIC LIGHT-EMITTING DIODE INCLUDING THE HETEROCYCLIC COMPOUND, AND FLAT DISPLAY DEVICE INCLUDING THE ORGANIC LIGHT-EMITTING DIODE

(75) Inventors: Sang-Hyun Han, Yongin (KR); Seok-Hwan Hwang, Yongin (KR); Young-Kook Kim, Yongin (KR); Hye-Jin Jung, Yongin (KR); Jin-O Lim, Yongin (KR); Se-Jin Cho, Yongin (KR); Jong-Hyuk Lee, Yongin (KR)

(73) Assignee: Samsung Display Co., Ltd., Samsung-ro, Giheung-Gu, Yongin-si, Gyeonggi-Do (KR)

( * ) Notice: Subject to any disclaimer, the term of this patent is extended or adjusted under 35 U.S.C. 154(b) by 1110 days.

(21) Appl. No.: 13/361,394

(22) Filed: Jan. 30, 2012

(65) Prior Publication Data

US 2013/0001527 A1 Jan. 3, 2013

(30) Foreign Application Priority Data

Jun. 28, 2011 (KR) .................. 10-2011-0063032

(51) Int. Cl.
*H01L 51/54* (2006.01)
*C07D 401/14* (2006.01)
(Continued)

(52) U.S. Cl.
CPC .......... *H01L 51/0072* (2013.01); *C07D 221/18* (2013.01); *C07D 401/04* (2013.01);
(Continued)

(58) Field of Classification Search
None
See application file for complete search history.

(56) References Cited

U.S. PATENT DOCUMENTS 5,635,308 A 6/1997 Inoue et al.
5,645,948 A 7/1997 Shi et al.
(Continued)

FOREIGN PATENT DOCUMENTS

JP 08012600 A 1/1996
JP 2000003782 A 1/2000
(Continued)

OTHER PUBLICATIONS

Tanga et al. (J. Het. Chem. 1985, 22, p. 1597) (English abstract).*
(Continued)

*Primary Examiner* — J. L. Yang
(74) *Attorney, Agent, or Firm* — Robert E. Bushnell, Esq.

(57) ABSTRACT

Provided are a heterocyclic compound represented by Formula 1 below, and an organic light-emitting diode and a flat display device each including the heterocyclic compound.

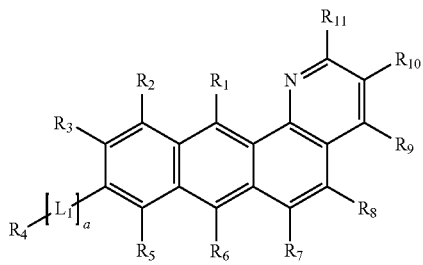

The organic light-emitting diode including an organic layer including the heterocyclic compound has a low driving voltage, high luminescence efficiency, and long lifetime.

23 Claims, 2 Drawing Sheets

(51) Int. Cl.
   *C07D 221/18* (2006.01)
   *H01L 51/00* (2006.01)
   *C07D 401/04* (2006.01)
   *C07D 401/10* (2006.01)
   *C07D 413/10* (2006.01)
   *C07D 471/04* (2006.01)
   *C09K 11/06* (2006.01)
   *H05B 33/14* (2006.01)
   *H01L 51/50* (2006.01)

(52) U.S. Cl.
   CPC ............ *C07D401/10* (2013.01); *C07D 401/14* (2013.01); *C07D 413/10* (2013.01); *C07D 471/04* (2013.01); *C09K 11/06* (2013.01); *H05B 33/14* (2013.01); *C09K 2211/1011* (2013.01); *C09K 2211/1014* (2013.01); *C09K 2211/1029* (2013.01); *C09K 2211/1033* (2013.01); *C09K 2211/1044* (2013.01); *H01L 51/0061* (2013.01); *H01L 51/5012* (2013.01); *H01L 51/5016* (2013.01)

(56) References Cited

U.S. PATENT DOCUMENTS

| | | |
|---|---|---|
| 5,972,247 A | 10/1999 | Shi et al. |
| 6,465,115 B2 | 10/2002 | Shi et al. |
| 6,596,415 B2 | 7/2003 | Shi et al. |
| 7,839,074 B2 | 11/2010 | Ikeda et al. |
| 2010/0289013 A1 | 11/2010 | Ito et al. |

FOREIGN PATENT DOCUMENTS

| | | |
|---|---|---|
| JP | 4025136 B2 | 10/2007 |
| JP | 4041816 B2 | 11/2007 |
| KR | 1020100064712 A | 6/2010 |
| KR | 1020100111037 A | 10/2010 |

OTHER PUBLICATIONS

Crusa et al. (Gazz. Chim. Ital. 1929, 59, p. 70).*
Campos et al. (Tetrahedron 1998, 54, p. 6929).*
Adachi et al., Confinement of charge carriers and molecular excitons within 5-nm-thick emitter layer in organic electroluminescent devices with a double heterostructure, Appl. Phys. Lett. (1990) 57, pp. 531-533.
Sakamoto et al., Synthesis, Characterization, and Electron-Transport Property of Perlluorinated Phenylene Dendrimers, J. Am. Chem. Soc. (2000) 122, pp. 1832-1833.
Tang et al., Organic elcectroluminescent diodes, Appl. Phys. Lett. (1987) 51, pp. 913-915.
Yamaguchi et al., Diphenylamino-Substituted 2,5-Diarylsiloles for Single-Layer Organic Electroluminescent Devices, Chem. Lett. (2001) pp. 98-99.

* cited by examiner

HETEROCYCLIC COMPOUND, ORGANIC LIGHT-EMITTING DIODE INCLUDING THE HETEROCYCLIC COMPOUND, AND FLAT DISPLAY DEVICE INCLUDING THE ORGANIC LIGHT-EMITTING DIODE

CLAIM OF PRIORITY

This application claims the benefit of Korean Patent Application Serial No. 10-2011-0063032, filed on 28 Jun. 2011 in the Korean Intellectual Property Office, the disclosure of which is incorporated herein in its entirety by reference.

BACKGROUND OF THE INVENTION

1. Field of the Invention

The present invention relates to a heterocyclic compound, an organic light-emitting diode including the heterocyclic compound, and a flat display device including the organic light-emitting diode.

2. Description of the Related Art

Organic light emitting diodes are self-emission devices that have a wide viewing angle, a high contrast ratio, a short response time, and excellent brightness, driving voltage, and response speed characteristics, thus enabling the generation of multi-color images.

In a typical organic light-emitting diode, an anode is formed on a substrate, and a hole transport layer, an emission layer, an electron transport layer, and a cathode are sequentially formed in this stated order on the anode. In this regard, the hole transport layer, the emission layer, and the electron transport layer are organic films including organic compounds.

A driving principle of an organic light-emitting diode having the structure described above will now be described in detail. When a voltage is applied between the anode and the cathode, holes injected from the anode pass the hole transport layer to the emission layer, and electrons injected from the cathode pass the electron transport layer to the emission layer. The holes and electrons, which are carriers, are recombined in the emission layer to generate excitons, which then change from an excited state to a ground state, thereby generating light.

SUMMARY OF THE INVENTION

The present invention provides a heterocyclic compound for an organic light-emitting diode having a low voltage, high brightness, high efficiency, long lifetime, an organic light-emitting diode including an organic layer including the heterocyclic compound, and a flat display device including the organic light-emitting diode.

According to an aspect of the present invention, there is provided a heterocyclic compound represented by Formula 1 below.

<Formula 1>

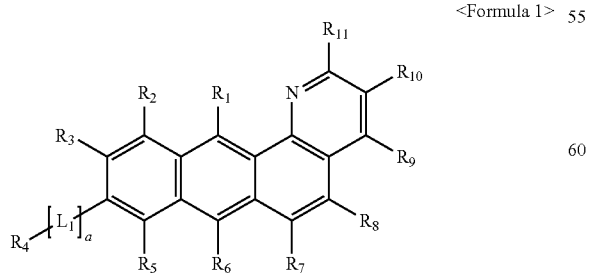

$R_1$ to $R_{11}$ are each independently a hydrogen atom, a deuterium atom, a halogen atom, a hydroxyl group, a cyano group, a nitro group, a carboxyl group, a substituted or unsubstituted $C_1$-$C_{30}$ alkyl group, a substituted or unsubstituted $C_2$-$C_{30}$ alkenyl group, a substituted or unsubstituted $C_2$-$C_{30}$ alkynyl group, a substituted or unsubstituted $C_1$-$C_{30}$ alkoxy group, a substituted or unsubstituted $C_3$-$C_{30}$ cycloalkyl group, a substituted or unsubstituted $C_3$-$C_{30}$ cycloalkenyl group, a substituted or unsubstituted $C_5$-$C_{30}$ aryl group, a substituted or unsubstituted $C_2$-$C_{30}$ heteroaryl group, a substituted or unsubstituted $C_5$-$C_{30}$ aryloxy group, a substituted or unsubstituted $C_5$-$C_{30}$ arylthio group, or a group represented by $N(Q_1)(Q_2)$ where $Q_1$ and $Q_2$ are each independently a hydrogen atom, a deuterium atom, a substituted or unsubstituted methyl group, a substituted or unsubstituted ethyl group, a substituted or unsubstituted propyl group, a substituted or unsubstituted butyl group, a substituted or unsubstituted pentyl group, a substituted or unsubstituted phenyl group, a substituted or unsubstituted pyridinyl group, a substituted or unsubstituted naphthyl group, a substituted or unsubstituted anthryl group, a substituted or unsubstituted fluorenyl group, a substituted or unsubstituted carbazolyl group, or a substituted or unsubstituted pyrimidinyl group.

$L_1$ is a substituted or unsubstituted $C_5$-$C_{30}$ arylene group, or a substituted or unsubstituted $C_3$-$C_{30}$ heteroarylene group, and a is an integer of 0 to 2, wherein if a is 2, two $L_1$ are identical to or different from each other.

According to another aspect of the present invention, there is provided an organic light-emitting diode including: a first electrode; a second electrode facing the first electrode; and a first layer interposed between the first electrode and the second electrode, wherein the first layer includes the heterocyclic compound described above.

According to another aspect of the present invention, there is provided a flat display device including: a transistor including a source, a drain, a gate, and an active layer; and the organic light-emitting diode, wherein one of the source and the drain is electrically connected to the first electrode of the organic light-emitting diode.

BRIEF DESCRIPTION OF THE DRAWINGS

The above and other features and advantages of the present invention will become more apparent by describing in detail exemplary embodiments thereof with reference to FIG. 1, which is a schematic view of an organic light-emitting diode according to an embodiment of the present invention.

DETAILED DESCRIPTION OF THE INVENTION

Figure 1:
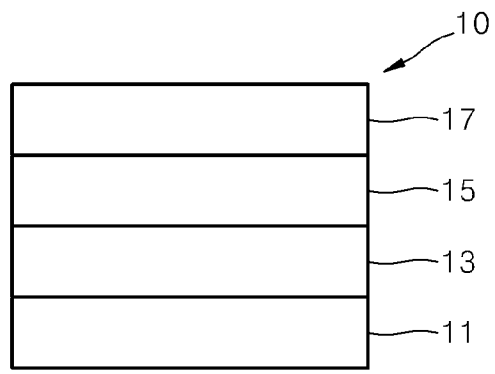

A heterocyclic compound according to an embodiment of the present invention is represented by Formula 1 below.

<Formula 1>

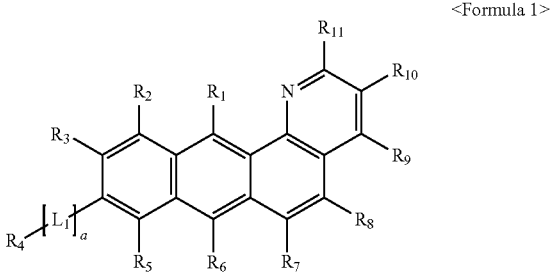

$R_1$ to $R_{11}$ may each be independently a hydrogen atom, a deuterium atom, a halogen atom, a hydroxyl group, a cyano group, a nitro group, a carboxyl group, a substituted or unsubstituted $C_1$-$C_{30}$ alkyl group, a substituted or unsubstituted $C_2$-$C_{30}$ alkenyl group, a substituted or unsubstituted $C_2$-$C_{30}$ alkynyl group, a substituted or unsubstituted $C_1$-$C_{30}$ alkoxy group, a substituted or unsubstituted $C_3$-$C_{30}$ cycloalkyl group, a substituted or unsubstituted $C_3$-$C_{30}$ cycloalkenyl group, a substituted or unsubstituted $C_5$-$C_{30}$ aryl group, a substituted or unsubstituted $C_2$-$C_{30}$ heteroaryl group, a substituted or unsubstituted $C_5$-$C_{30}$ aryloxy group, or a substituted or unsubstituted $C_5$-$C_{30}$ arylthio group, or a group represented by $N(Q_1)(Q_2)$ where $Q_1$ and $Q_2$ may each be independently a hydrogen atom, a deuterium atom, a substituted or unsubstituted methyl group, a substituted or unsubstituted ethyl group, a substituted or unsubstituted propyl group, a substituted or unsubstituted butyl group, a substituted or unsubstituted pentyl group, a substituted or unsubstituted phenyl group, a substituted or unsubstituted pyridinyl group, a substituted or unsubstituted naphthyl group, a substituted or unsubstituted anthryl group, a substituted or unsubstituted fluorenyl group, a substituted or unsubstituted carbazolyl group, or a substituted or unsubstituted pyrimidinyl group.

$L_1$ may be a substituted or unsubstituted $C_5$-$C_{30}$ arylene group, or a substituted or unsubstituted $C_3$-$C_{30}$ heteroarylene group, a is an integer of 0 to 2, and if a is 2, two $L_1$ may be identical to or different from each other.

In detail, $R_1$ to $R_{11}$ may each be independently a hydrogen atom, a deuterium atom, a halogen atom, a hydroxyl group, a cyano group, a nitro group, a carboxyl group, a substituted or unsubstituted methyl group, a substituted or unsubstituted ethyl group, a substituted or unsubstituted propyl group, a substituted or unsubstituted butyl group, a substituted or unsubstituted pentyl group, a substituted or unsubstituted phenyl group, a substituted or unsubstituted biphenyl group, a substituted or unsubstituted terphenyl group, a substituted or unsubstituted phenoxy group, a substituted or unsubstituted fluorenyl group, a substituted or unsubstituted carbazolyl group, a substituted or unsubstituted naphthyl group, a substituted or unsubstituted phenanthrenyl group, a substituted or unsubstituted pyridinyl group, a substituted or unsubstituted diazinyl group, a substituted or unsubstituted triazinyl group, a substituted or unsubstituted quinolinyl group, a substituted or unsubstituted benzimidazolyl group, a substituted or unsubstituted benzoxazolyl group, a substituted or unsubstituted pentalenyl group, a substituted or unsubstituted indenyl group, a substituted or unsubstituted azulenyl group, a substituted or unsubstituted heptalenyl group, a substituted or unsubstituted indacenyl group, a substituted or unsubstituted acenaphthyl group, a substituted or unsubstituted spirofluorenyl group, a substituted or unsubstituted phenalenyl group, a substituted or unsubstituted phenanthridinyl group, a substituted or unsubstituted phenanthrolinyl group, a substituted or unsubstituted anthryl group, a substituted or unsubstituted fluoranthenyl group, a substituted or unsubstituted triphenylenyl group, a substituted or unsubstituted pyrenyl group, a substituted or unsubstituted chricenyl group, a substituted or unsubstituted naphthacenyl group, a substituted or unsubstituted picenyl group, a substituted or unsubstituted perylenyl group, a substituted or unsubstituted pentaphenyl group, a substituted or unsubstituted hexacenyl group, a substituted or unsubstituted pyrrolyl group, a substituted or unsubstituted imidazolyl group, a substituted or unsubstituted pyrazolyl group, a substituted or unsubstituted imidazopyrimidinyl group, a substituted or unsubstituted pyridazinyl group, a substituted or unsubstituted pyrimidinyl group, a substituted or unsubstituted imidazopyrimidinyl group, a substituted or unsubstituted pyridazinyl group, a substituted or unsubstituted indolyl group, a substituted or unsubstituted isoindolyl group, a substituted or unsubstituted pyrido indolyl group, a substituted or unsubstituted indazolyl group, a substituted or unsubstituted purinyl group, a substituted or unsubstituted benzoquinolinyl group, a substituted or unsubstituted phthalazinyl group, substituted or unsubstituted naphthyridinyl group, a substituted or unsubstituted quinoxalinyl group, a substituted or unsubstituted quinazolinyl group, a substituted or unsubstituted phenazinyl group, a substituted or unsubstituted furanyl group, a substituted or unsubstituted benzofuranyl group, a substituted or unsubstituted dibenzofuranyl group, a substituted or unsubstituted thiophenyl group, a substituted or unsubstituted benzothiophenyl group, a substituted or unsubstituted dibenzothiophenyl group, a substituted or unsubstituted thiazolyl group, a substituted or unsubstituted isothiazolyl group, a substituted or unsubstituted benzothiazolyl group, a substituted or unsubstituted oxazolyl group, a substituted or unsubstituted isooxazolyl group, a substituted or unsubstituted oxadiazolyl group, a substituted or unsubstituted triazolyl group, a substituted or unsubstituted tetrazolyl group, or a group represented by $N(Q_1)(Q_2)$. In this regard, $Q_1$ and $Q_2$ may each be independently a hydrogen atom, a deuterium atom, a substituted or unsubstituted methyl group, a substituted or unsubstituted ethyl group, a substituted or unsubstituted propyl group, a substituted or unsubstituted butyl group, a substituted or unsubstituted pentyl group, a substituted or unsubstituted phenyl group, a substituted or unsubstituted pyridinyl group, a substituted or unsubstituted naphthyl group, a substituted or unsubstituted anthryl group, a substituted or unsubstituted fluorenyl group, a substituted or unsubstituted carbazolyl group, or a substituted or unsubstituted pyrimidinyl group, but are not limited thereto.

For example, $R_1$ to $R_{11}$ may each be independently a hydrogen atom, a deuterium atom, a halogen atom, a substituted or unsubstituted methyl group, a substituted or unsubstituted ethyl group, a substituted or unsubstituted propyl group, a substituted or unsubstituted butyl group, or a group represented by Formulae 2A to 2P below, but are not limited thereto.

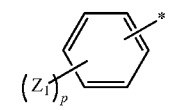

<Formula 2A>

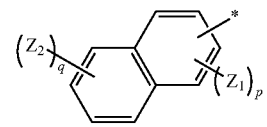

<Formula 2B>

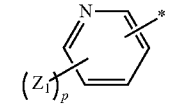

<Formula 2C>

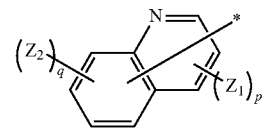

<Formula 2D>

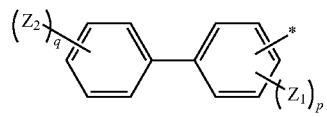

<Formula 2E>

-continued

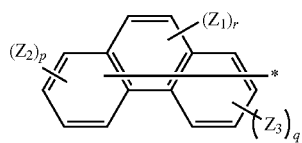
<Formula 2F>

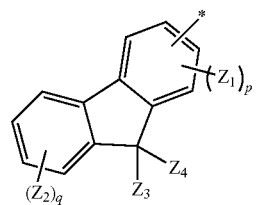
<Formula 2G>

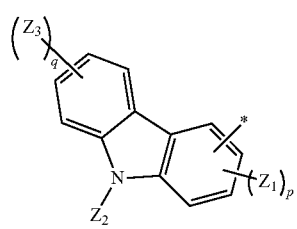
<Formula 2H>

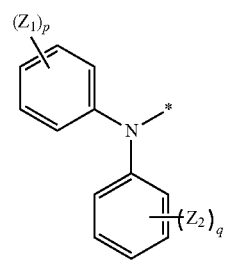
<Formula 2I>

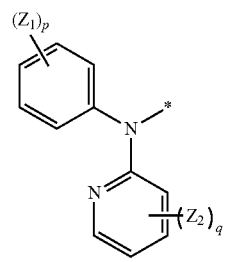
<Formula 2J>

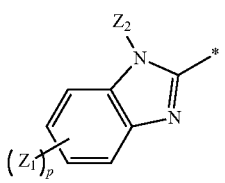
<Formula 2K>

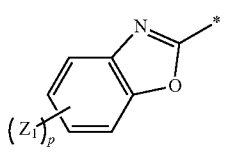
<Formula 2L>

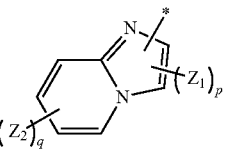
<Formula 2M>

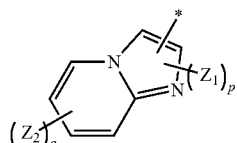
<Formula 2N>

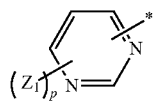
<Formula 2O>

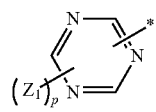
<Formula 2P>

$Z_1$, $Z_2$, $Z_3$, and $Z_4$ may each be independently a hydrogen atom, a deuterium atom, a halogen atom, a hydroxyl group, a cyano group, a substituted or unsubstituted methyl group, a substituted or unsubstituted ethyl group, a substituted or unsubstituted propyl group, a substituted or unsubstituted butyl group, a substituted or unsubstituted methoxy group, a substituted or unsubstituted ethoxy group, a substituted or unsubstituted phenyl group, a substituted or unsubstituted naphthyl group, a substituted or unsubstituted anthryl group, and a substituted or unsubstituted quinolinyl group, or a substituted or unsubstituted pyridinyl group, and a plurality of each of $Z_1$, $Z_2$, $Z_3$, and $Z_4$ may be identical to or different from each other. p and q may each be an integer of 1 to 5, r may be 1 or 2, and * indicates a binding site.

For example, $R_1$ to $R_{11}$ may each be independently a hydrogen atom, a deuterium atom, a halogen atom, a substituted or unsubstituted methyl group, a substituted or unsubstituted ethyl group, a substituted or unsubstituted propyl group, a substituted or unsubstituted tert-butyl group, or one of the groups represented by Formulae 3A to 3R, but are not limited thereto.

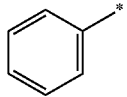
<Formula 3A>

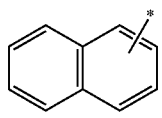
<Formula 3B>

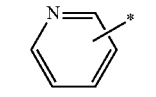
<Formula 3C>

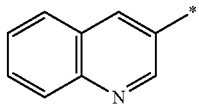
<Formula 3D>

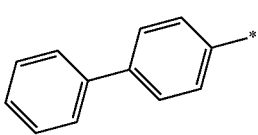
<Formula 3E>

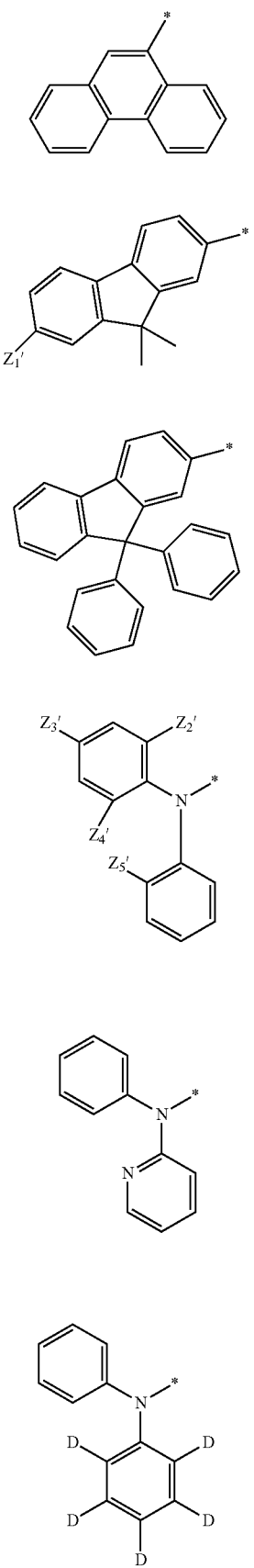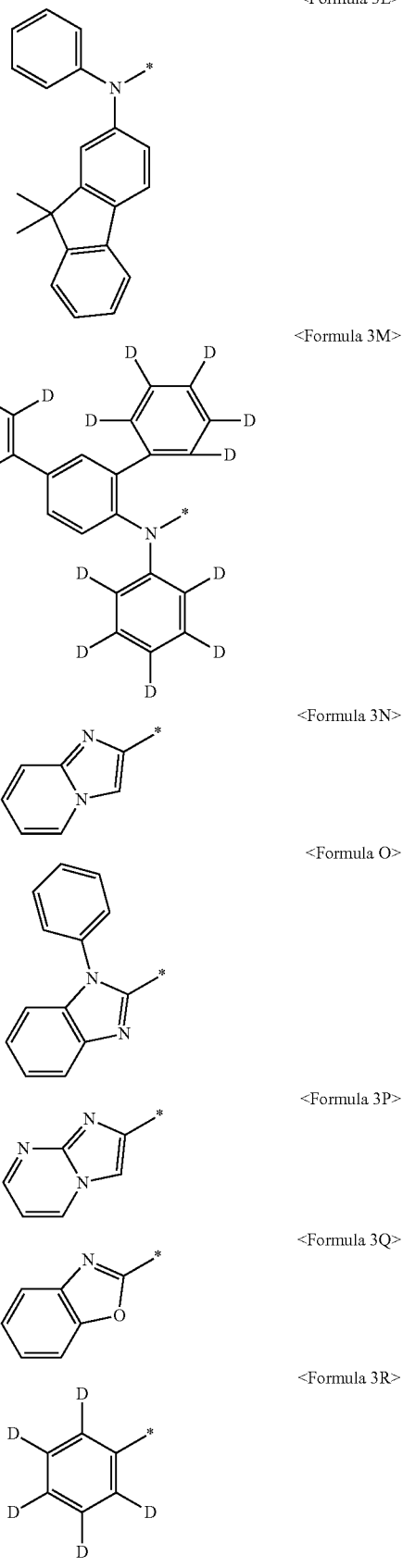

$Z_{1'}$ may be a hydrogen atom or a phenyl group, $Z_{2'}$, $Z_{3'}$, $Z_{4'}$, and $Z_{5'}$ may each be independently a hydrogen atom, a deuterium atom, a fluoro group, a methyl group, or a phenyl group, and a plurality of each of $Z_{2'}$, $Z_{3'}$, $Z_{4'}$, and $Z_{5'}$ may be identical to or different from each other. * indicates a binding site.

$L_1$ may be a substituted or unsubstituted phenylene group, a substituted or unsubstituted naphthylene group, a substituted or unsubstituted fluorenylene group, a substituted or unsubstituted carbazolylene group, a substituted or unsubstituted pyridinylene group, a substituted or unsubstituted pyrimidinylene group, a substituted or unsubstituted triazinylene group, a substituted or unsubstituted anthrylene group, a substituted or unsubstituted phenanthrenylene group, a substituted or unsubstituted pyrenylene group, a substituted or unsubstituted chrycenylene group, a substituted or unsubstituted perilenylene group, a substituted or unsubstituted spirofluorenyl group, or a substituted or unsubstituted oxadiazolylene group, but is not limited thereto.

In detail, $L_1$ may be one of the groups represented by Formulae 4A to 4H below, but is not limited thereto.

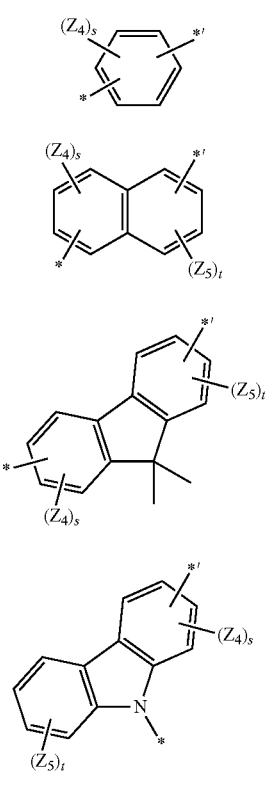

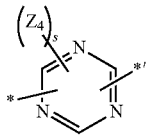

<Formula 4G>

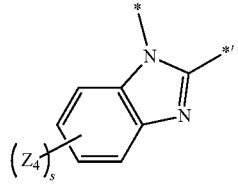

<Formula 4H>

In Formulae 4A to 4H, $Z_4$ and $Z_5$ may each be independently a hydrogen atom, a deuterium atom, halogen atom, a substituted or unsubstituted methyl group, a substituted or unsubstituted ethyl group, a substituted or unsubstituted propyl group, a substituted or unsubstituted butyl group, or a substituted or unsubstituted phenyl group, and a plurality of each of $Z_4$ and $Z_5$ may be identical to or different from each other. s and t each are an integer of 1 to 4, *' indicates a binding site with an anthracene back bone, and * indicates a binding site with $R_4$.

For example, $L_1$ is one of the groups represented by Formulae 5A to 5I below, but is not limited thereto.

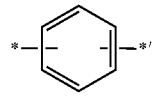

<Formula 5A>

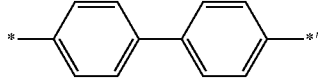

<Formula 5B>

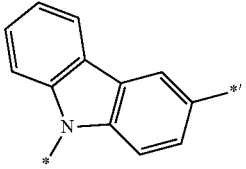

<Formula 5C>

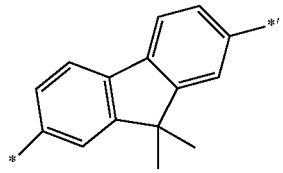

<Formula 5D>

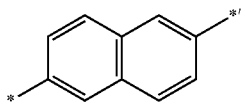

<Formula 5E>

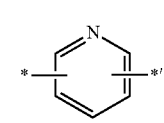

<Formula 5F>

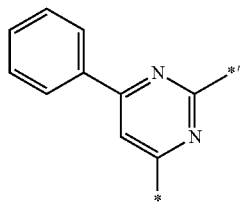

<Formula 5G>

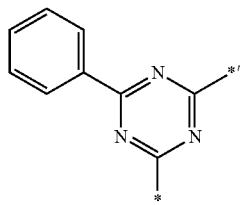

<Formula 5H>

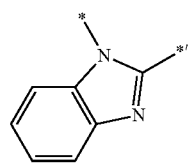

<Formula 5I>

In Formulae 5A to 5I, *' indicates a binding site with the anthracene back bone, and * indicates a binding site with $R_4$.

Also, $R_1$ and $R_6$ may be identical to each other.

For example, the heterocyclic compound represented by Formula 1 may be represented by Formula 1a below.

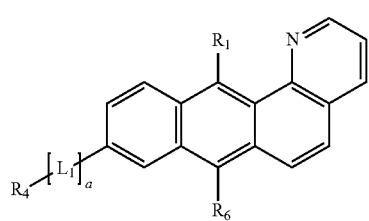

<Formula 1a>

$R_1$, $R_4$, and $R_6$ in Formula 1a may each be independently a hydrogen atom, a deuterium atom, a halogen atom, a hydroxyl group, a cyano group, a nitro group, a carboxyl group, a substituted or unsubstituted methyl group, a substituted or unsubstituted ethyl group, a substituted or unsubstituted propyl group, a substituted or unsubstituted butyl group, a substituted or unsubstituted pentyl group, a substituted or unsubstituted phenyl group, a substituted or unsubstituted biphenyl group, a substituted or unsubstituted fluorenyl group, a substituted or unsubstituted carbazolyl group, a substituted or unsubstituted naphthyl group, a substituted or unsubstituted phenanthrenyl group, a substituted or unsubstituted pyridinyl group, a substituted or unsubstituted diazinyl group, a substituted or unsubstituted triazinyl group, a substituted or unsubstituted quinolinyl group, a substituted or unsubstituted benzimidazolyl group, a substituted or unsubstituted benzoxazolyl group, a substituted or unsubstituted imidazopyrimidinyl group, a substituted or unsubstituted pyrimidinyl group, a substituted or unsubstituted imidazopyrimidinyl group, a substituted or unsubstituted indolyl group, a substituted or unsubstituted pyrido indolyl group, a substituted or unsubstituted (uranyl group, a substituted or unsubstituted benzofuranyl group, a substituted or unsubstituted dibenzofuranyl group, a substituted or unsubstituted thiophenyl group, a substituted or unsubstituted benzothiophenyl group, a substituted or unsubstituted dibenzothiophenyl group, a substituted or unsubstituted oxazolyl group, a substituted or unsubstituted oxadiazolyl group, or a group represented by $N(Q_1)(Q_2)$ where $Q_1$ and $Q_2$ are each independently a hydrogen atom, a deuterium atom, a substituted or unsubstituted methyl group, a substituted or unsubstituted ethyl group, a substituted or unsubstituted propyl group, a substituted or unsubstituted butyl group, a substituted or unsubstituted phenyl group, a substituted or unsubstituted pyridinyl group, a substituted or unsubstituted naphthyl group, a substituted or unsubstituted fluorenyl group, or a substituted or unsubstituted carbazolyl group.

$L_1$ may be a substituted or unsubstituted phenylene group, a substituted or unsubstituted naphthylene group, a substituted or unsubstituted fluorenylene group, a substituted or unsubstituted carbazolylene group, a substituted or unsubstituted pyridinylene group, a substituted or unsubstituted pyrimidinylene group, a substituted or unsubstituted triazinylene group, a substituted or unsubstituted anthrylene group, a substituted or unsubstituted phenanthrenylene group, a substituted or unsubstituted pyrenylene group, a substituted or unsubstituted chrycenylene group, a substituted or unsubstituted perilenylene group, a substituted or unsubstituted spirofluorenyl group, or a substituted or unsubstituted oxadiazolylene group.

a may be an integer of 0 to 2; if a is 2, two $L_1$ may be identical to or different from each other.

In detail, $R_1$, $R_4$, and $R_6$ in Formula 1a may each be independently a hydrogen atom, a deuterium atom, halogen atom, a substituted or unsubstituted methyl group, a substituted or unsubstituted ethyl group, a substituted or unsubstituted propyl group, a substituted or unsubstituted butyl group, or one of the groups represented by Formulae 2A to 2P below.

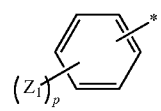

<Formula 2A>

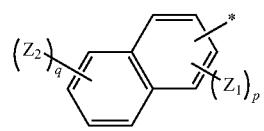

<Formula 2B>

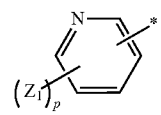

<Formula 2C>

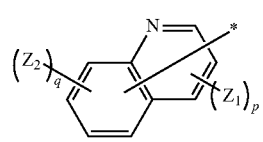

<Formula 2D>

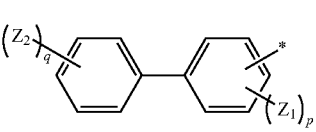

<Formula 2E>

-continued

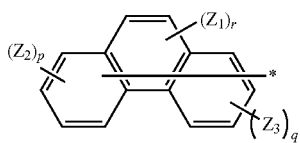
<Formula 2F>

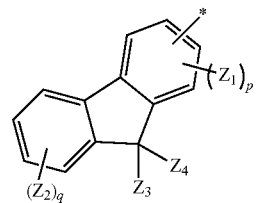
<Formula 2G>

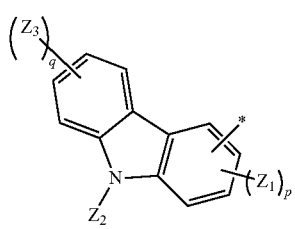
<Formula 2H>

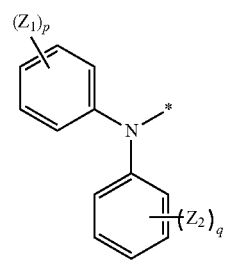
<Formula 2I>

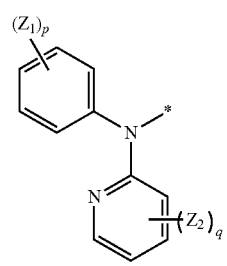
<Formula 2J>

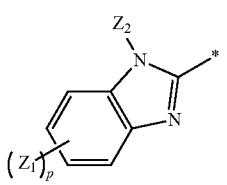
<Formula 2K>

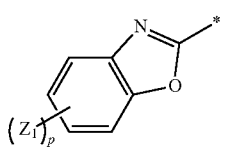
<Formula 2L>

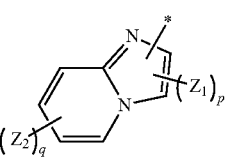
<Formula 2M>

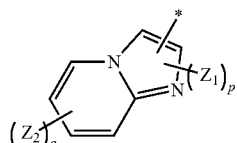
<Formula 2N>

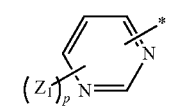
<Formula 2O>

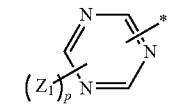
<Formula 2P>

$Z_1$, $Z_2$, $Z_3$, and $Z_4$ in Formulae 2A to 2P may each be independently a hydrogen atom, a deuterium atom, a halogen atom, a hydroxyl group, a cyano group, a substituted or unsubstituted methyl group, a substituted or unsubstituted ethyl group, a substituted or unsubstituted propyl group, a substituted or unsubstituted butyl group, a substituted or unsubstituted methoxy group, a substituted or unsubstituted ethoxy group, a substituted or unsubstituted phenyl group, a substituted or unsubstituted naphthyl group, a substituted or unsubstituted anthryl group, and a substituted or unsubstituted quinolinyl group, or a substituted or unsubstituted pyridinyl group, and a plurality of each of $Z_1$, $Z_2$, $Z_3$, and $Z_4$ may be identical to or different from each other. p, and q may each be an integer of 1 to 5, r may be 1 or 2, and * indicates a binding site.

In detail, $L_1$ in Formula 1a may be one of the groups represented by Formulae 4A to 4H below.

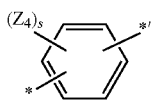
<Formula 4A>

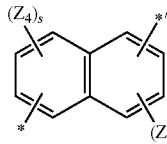
<Formula 4B>

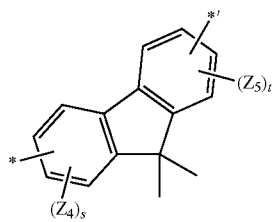
<Formula 4C>

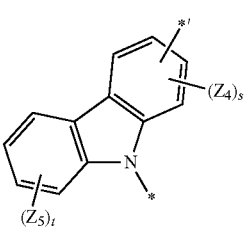
<Formula 4D>

-continued

<Formula 4E>
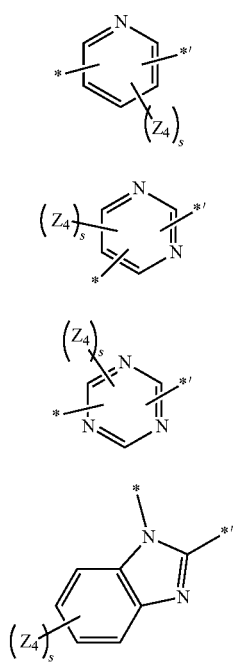
<Formula 4F>
<Formula 4G>
<Formula 4H>

In Formulae 4A to 4H, $Z_4$ and $Z_5$ may each be independently a hydrogen atom, a deuterium atom, halogen atom, a substituted or unsubstituted methyl group, a substituted or unsubstituted ethyl group, a substituted or unsubstituted propyl group, a substituted or unsubstituted butyl group, or a substituted or unsubstituted phenyl group, and a plurality of each of $Z_4$ and $Z_5$ may be identical to or different from each other. s and t may each be an integer of 1 to 4, *' indicates a binding site with the anthracene back bone, and * indicates a binding site with $R_4$.

For example, $R_1$, $R_4$, and $R_6$ in Formula 1a may each be independently a hydrogen atom, a deuterium atom, a halogen atom, a substituted or unsubstituted methyl group, a substituted or unsubstituted ethyl group, a substituted or unsubstituted propyl group, a substituted or unsubstituted tert-butyl group, or a group represented by Formula 3A to 3R below.

<Formula 3A>
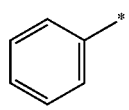

<Formula 3B>
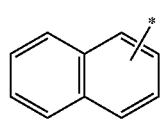

<Formula 3C>
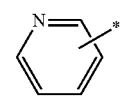

<Formula 3D>
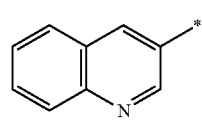

<Formula 3E>
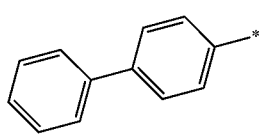

<Formula 3F>
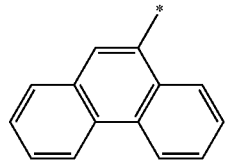

<Formula 3G>
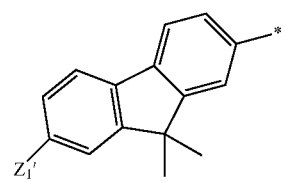

<Formula 3H>
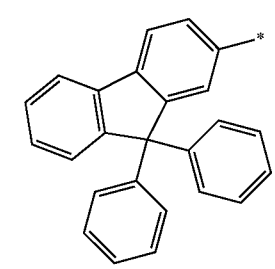

<Formula 3I>
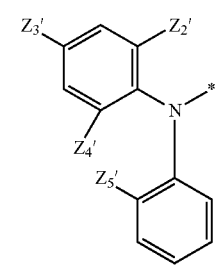

<Formula 3J>
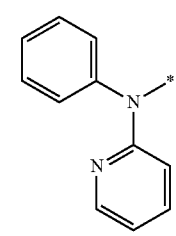

<Formula 3K>
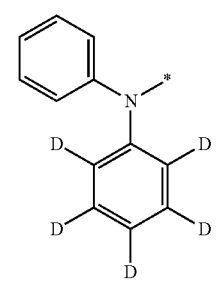

-continued

<Formula 3L>
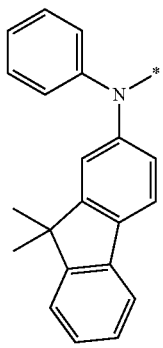

<Formula 3M>
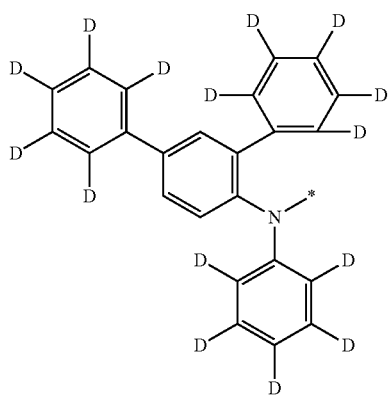

<Formula 3N>
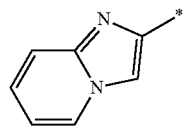

<Formula O>
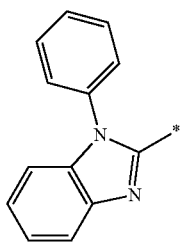

<Formula 3P>
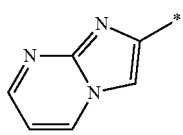

<Formula 3Q>
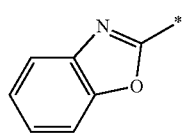

<Formula 3R>
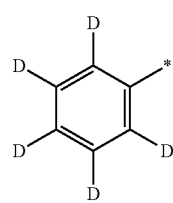

In Formula 3A to 3R, $Z_{1'}$ may be a hydrogen atom or a phenyl group, $Z_{2'}$, $Z_{3'}$, $Z_{4'}$, and $Z_{5'}$ may each be independently a hydrogen atom, a deuterium atom, a fluoro group, a methyl group, or a phenyl group, and a plurality of each of $Z_{2'}$, $Z_{3'}$, $Z_{4'}$, and $Z_{5'}$ may be identical to or different from each other. * indicates a binding site.

Also, $R_1$ and $R_6$ may be identical to each other.

For example, $L_1$ in Formula 1a may be one of the groups represented by Formulae 5A to 5I below.

<Formula 5A>
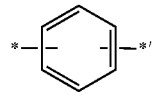

<Formula 5B>
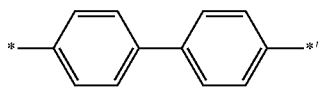

<Formula 5C>
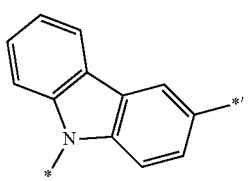

<Formula 5D>
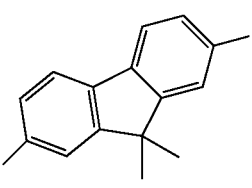

<Formula 5E>
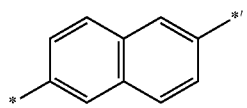

<Formula 5F>
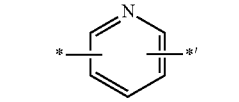

<Formula 5G>
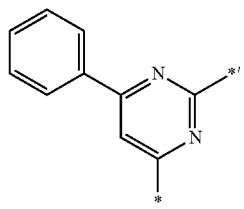

<Formula 5H>
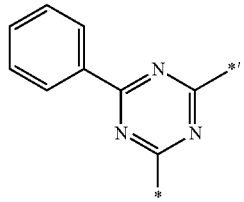

<Formula 5I>

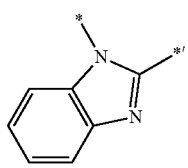

In Formulae 5A to 5I, *' indicates a binding site with the anthracene back bone, and * indicates a binding site with R₄.

The heterocyclic compound represented by Formula 1 may have a function as an emission material and/or electron transport material for an organic light-emitting diode. Also, the heterocyclic compound represented by Formula 1 having a heterocycle may have a high glass transition temperature (Tg) or melting point due to the introduction of a heterocycle therein. Accordingly, during the light-emission, the heterocyclic compound has stronger resistance against Joule heat that is generated within organic layers, between organic layers, or between an organic layer and a metallic electrode, and stronger resistance under high-temperature. Also, the heterocyclic compound represented by Formula 1 has nitrogen as a hetero atom in its molecular structure and an anthracene cycle to which a hetero cycle is fused. Due to such a structure, the heterocyclic compound represented by Formula 1 is enriched with more π electrons than an anthracene molecule, and a non-covalent electron pair may also participate in emission of light and it is highly likely that the probability of π→π* transition and n→π* transition in its molecular structure increases and thus, it is assumed that light emission efficiency may be increased. Also, if a substituent, such as a fluorene group, is introduced to the heterocyclic compound represented by Formula 1, a morphology of an organic layer may be improved and thus, characteristics of a formed organic light-emitting diode may be improved.

The heterocyclic compound represented by Formula 1 may be one of Compounds 1 to 80 having the following structures, but is not limited thereto.

1

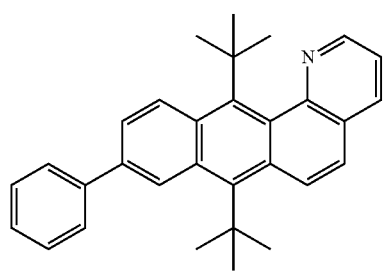

2

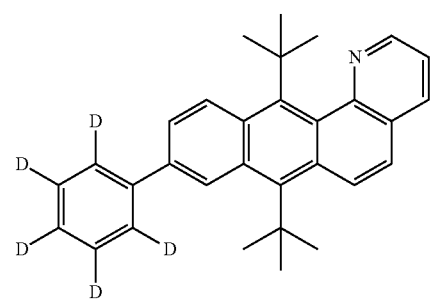

3

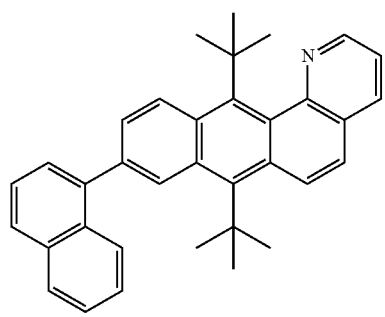

4

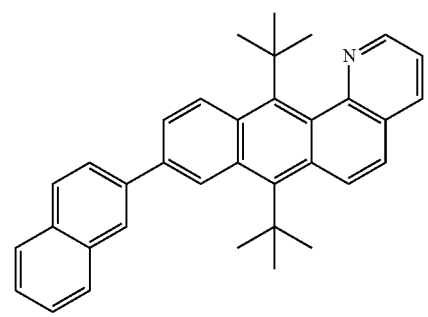

5

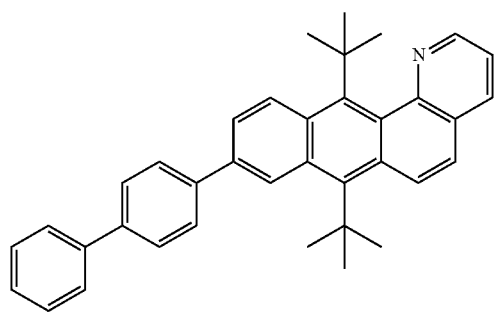

6

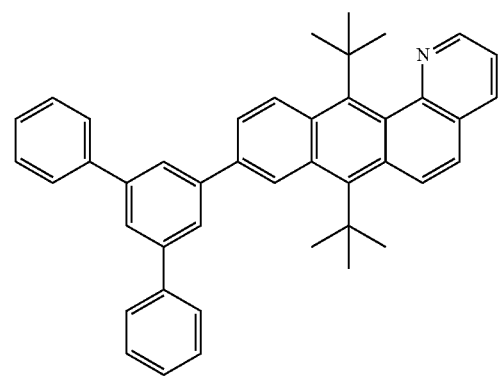

-continued
7
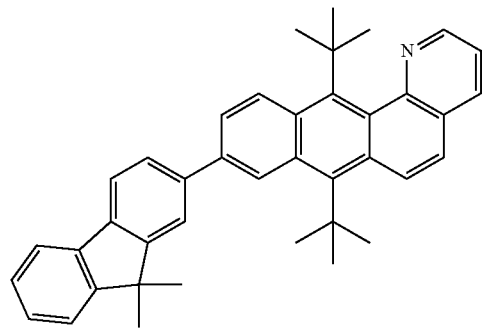
8
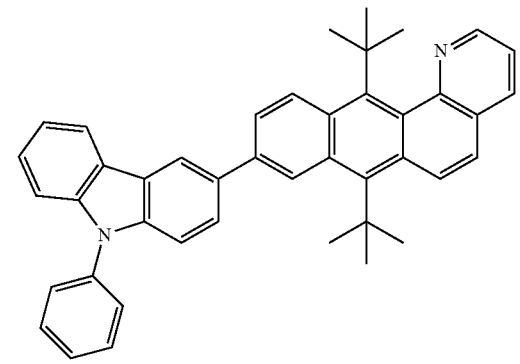
9
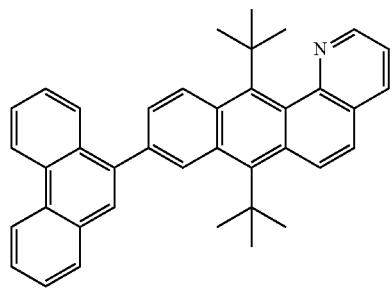
10
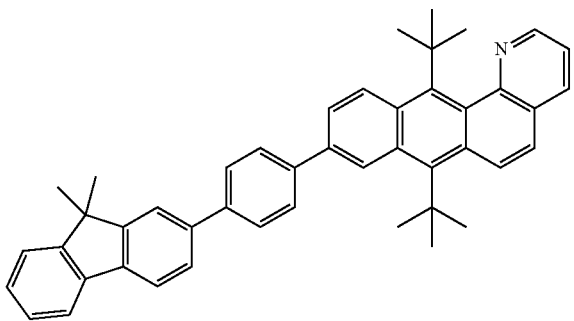
11
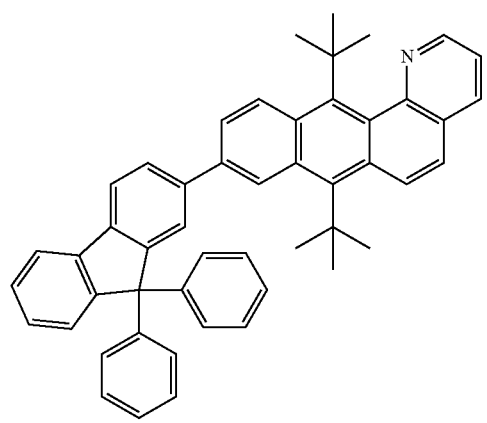
12
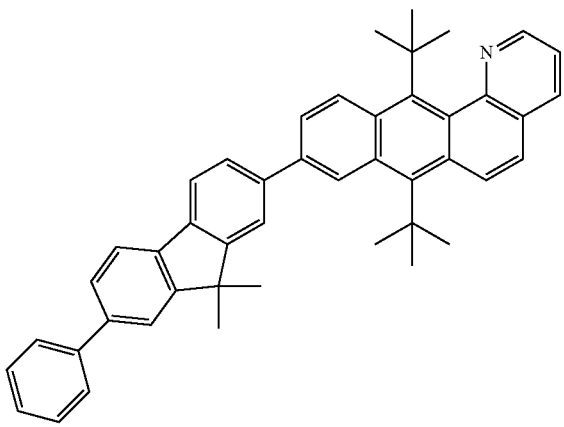
13
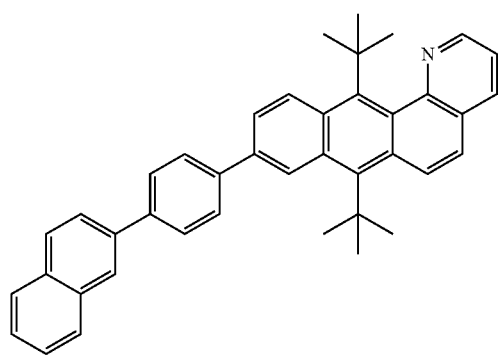
14
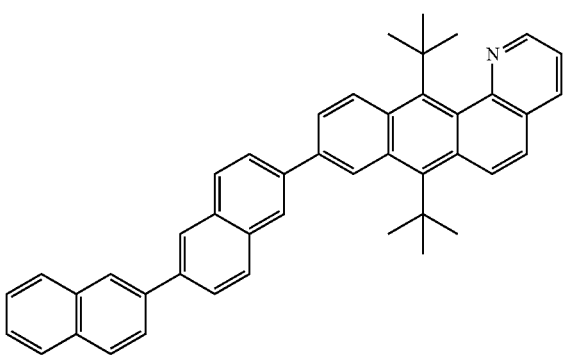

-continued
15
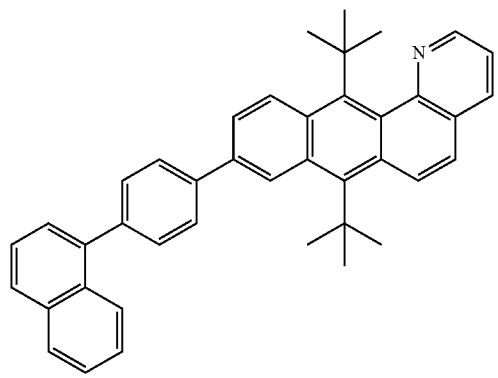
16
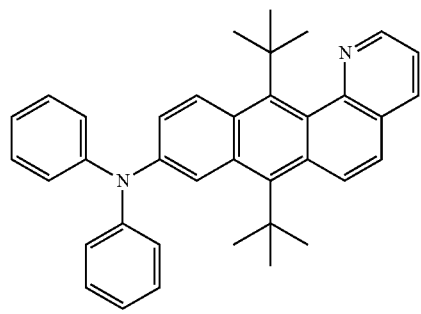
17
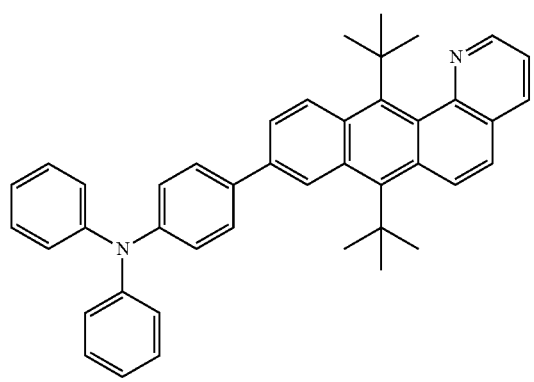
18
19
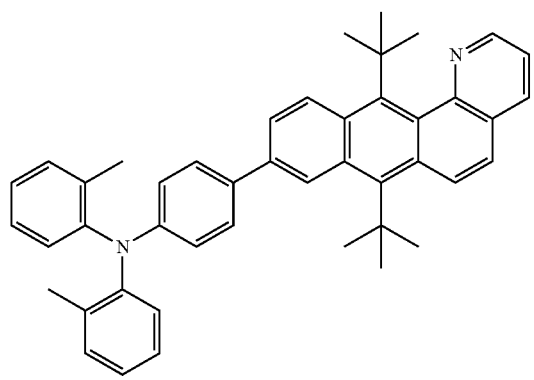
20
21
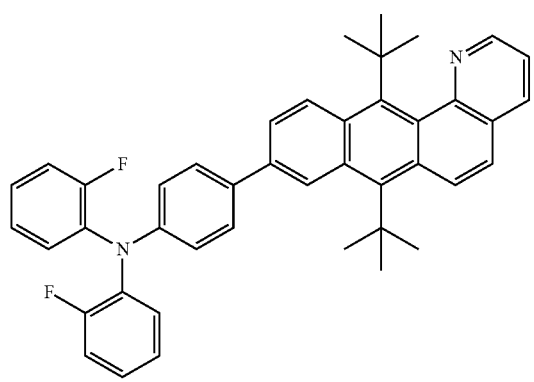
22
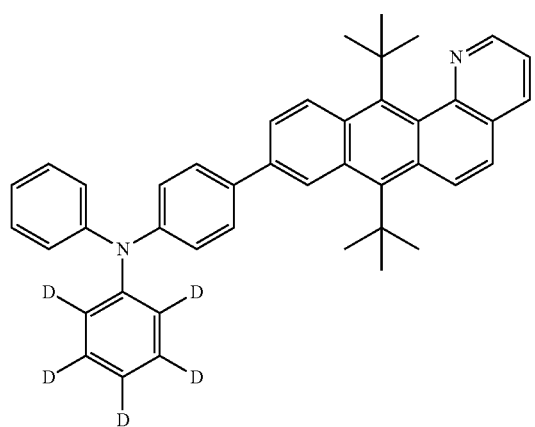

-continued
23
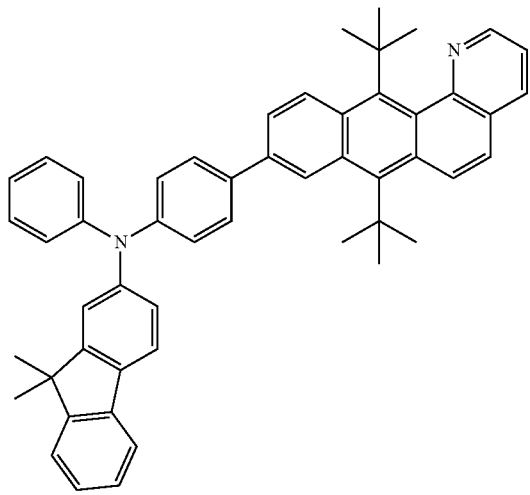
24
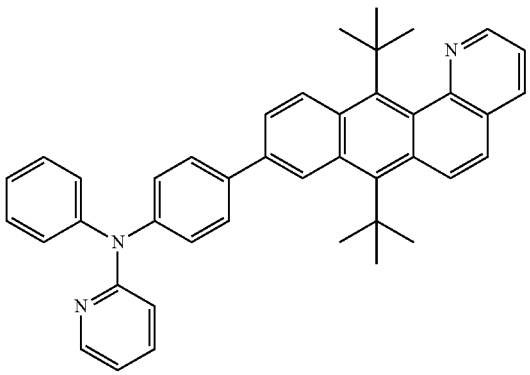
25
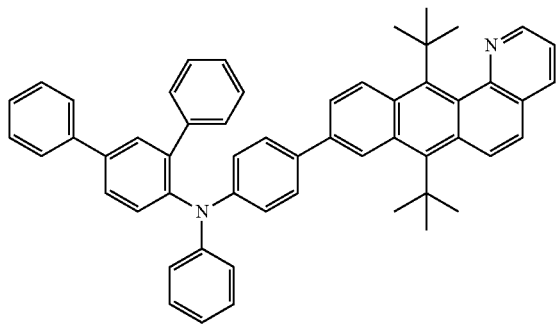
26
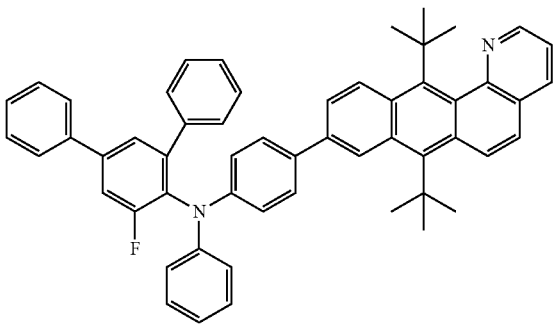
27
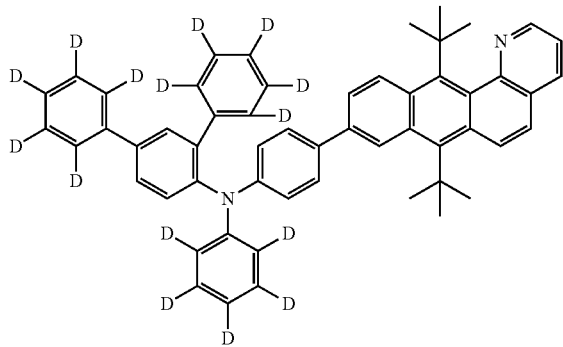
28
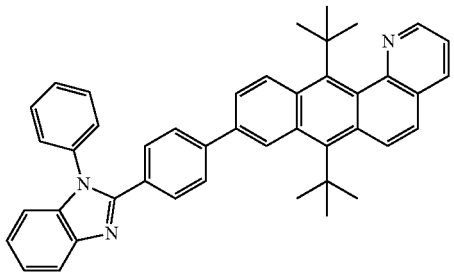
29
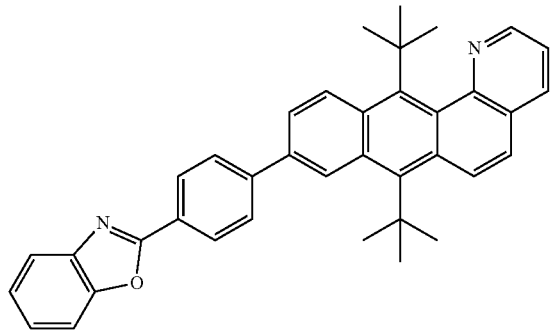
30
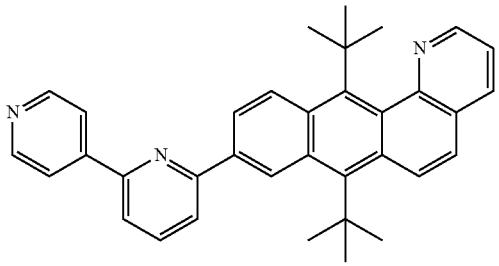

-continued
31
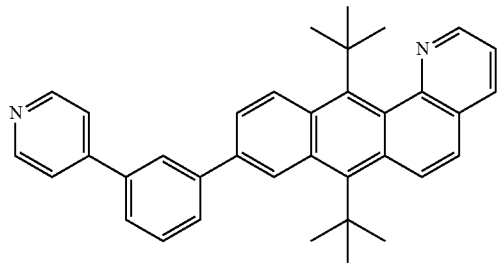
32
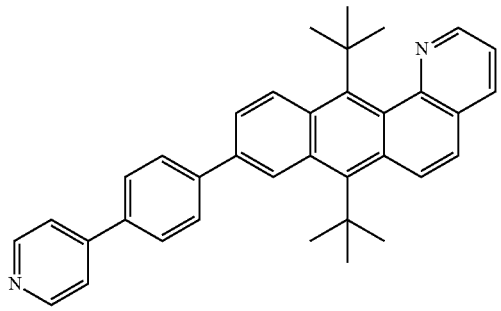
33
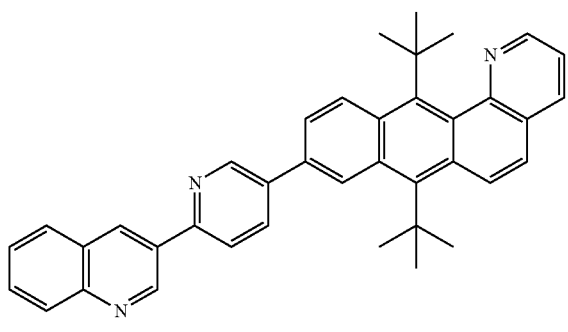
34
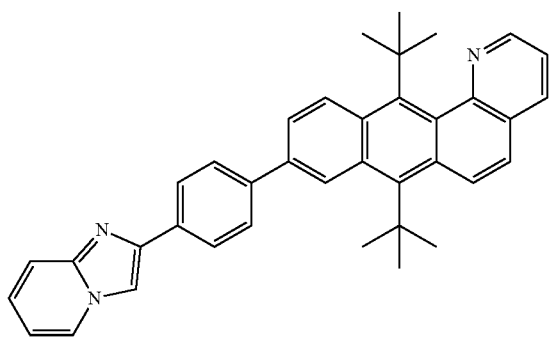
35
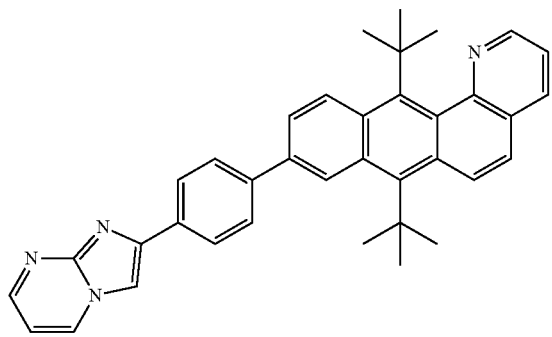
36
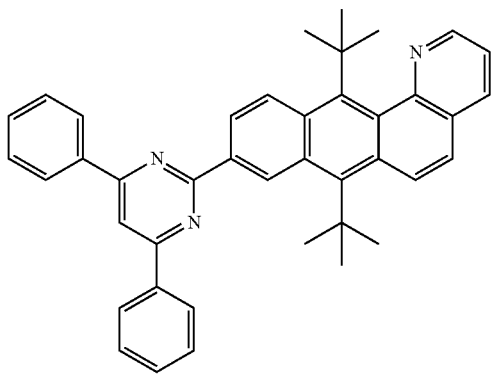
37
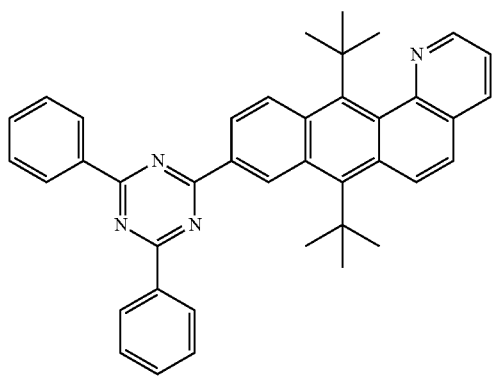
38
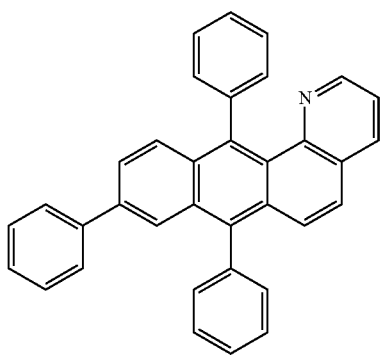

-continued
39
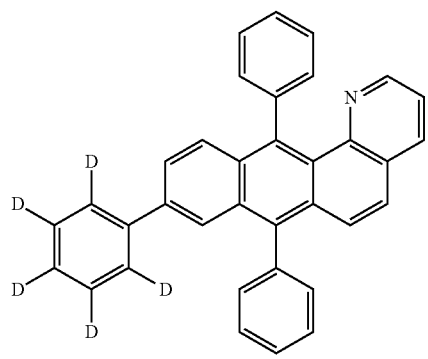
40
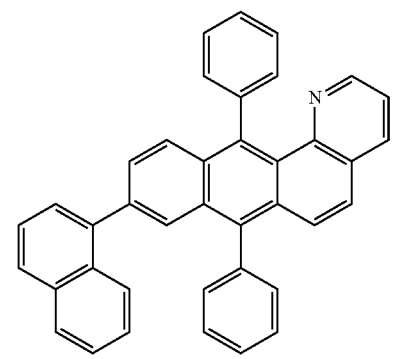
41
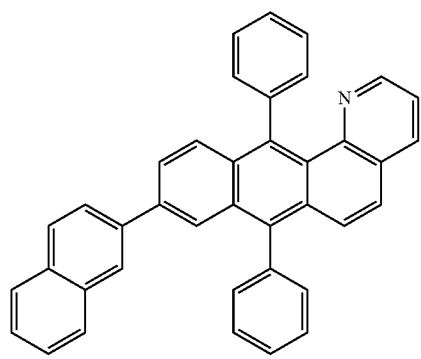
42
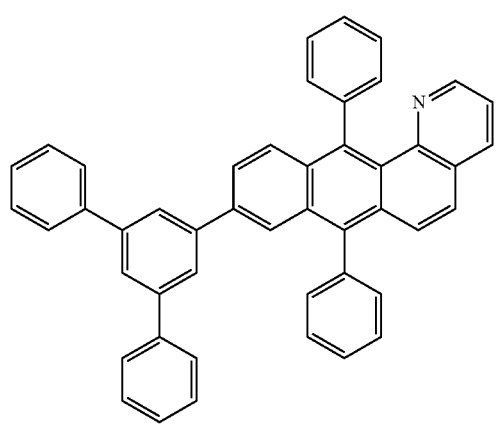
43
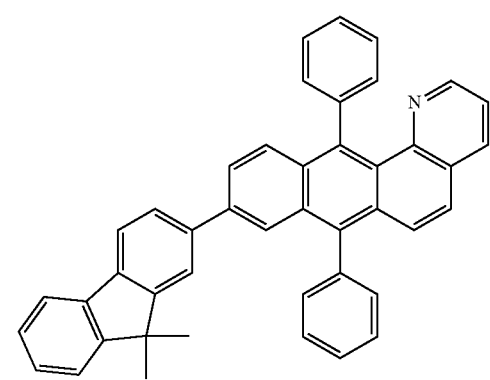
44
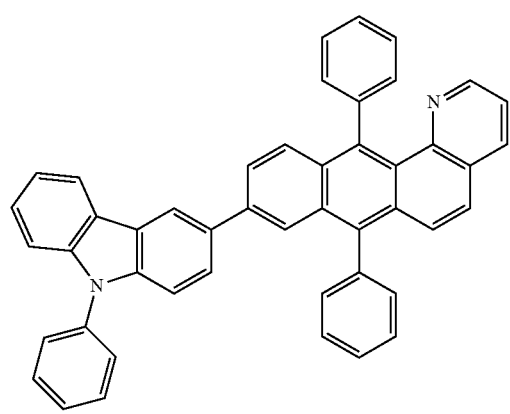
45
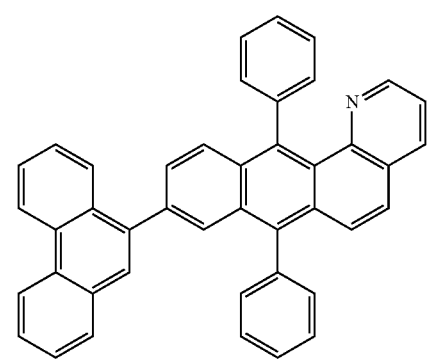
46

47
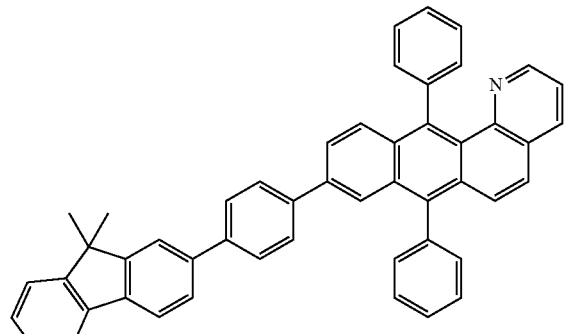
48
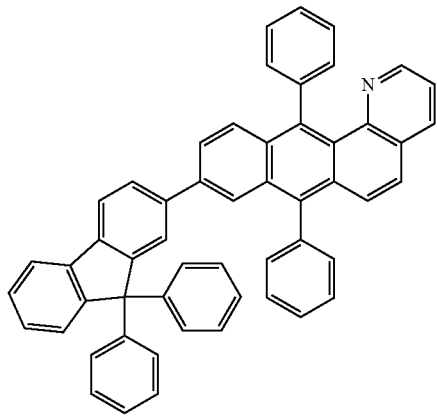
49
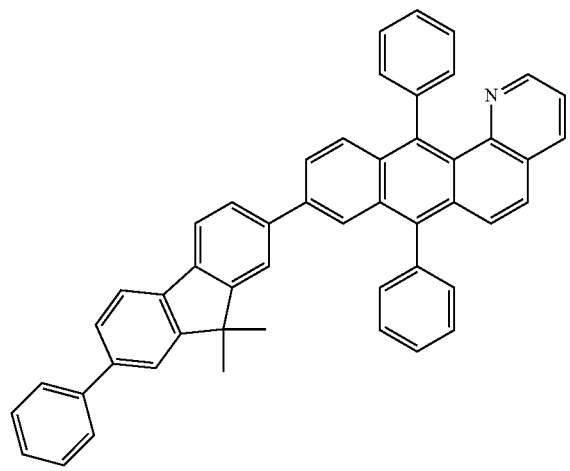
50
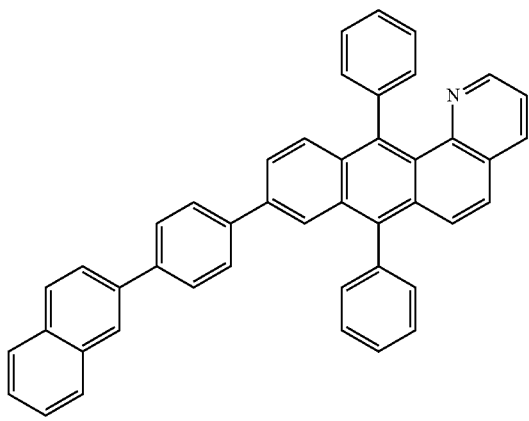
51
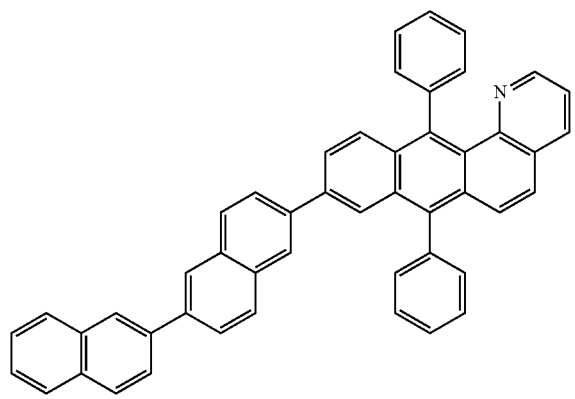
52
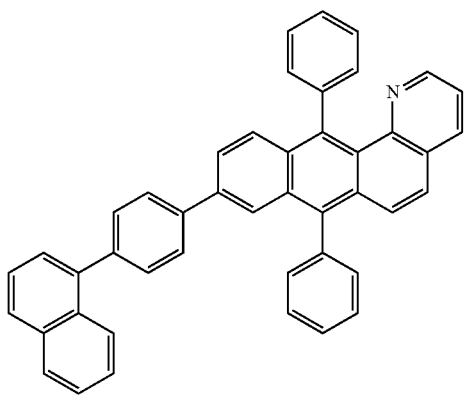

53
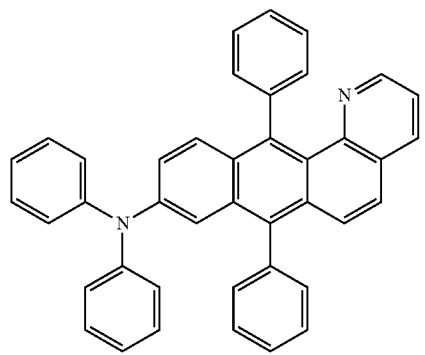
54
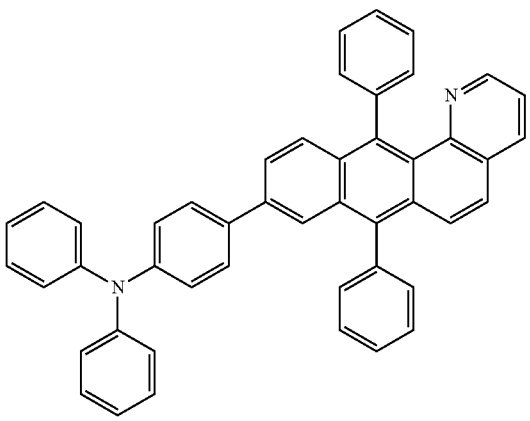
55
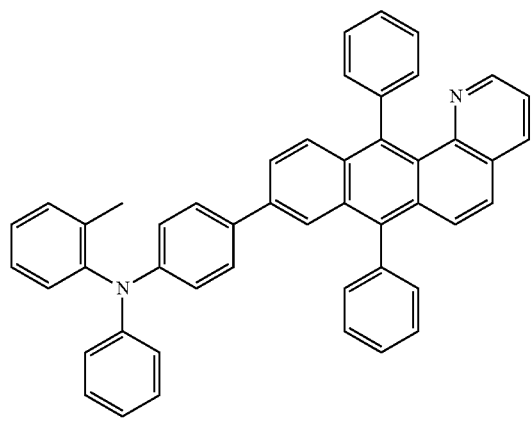
56
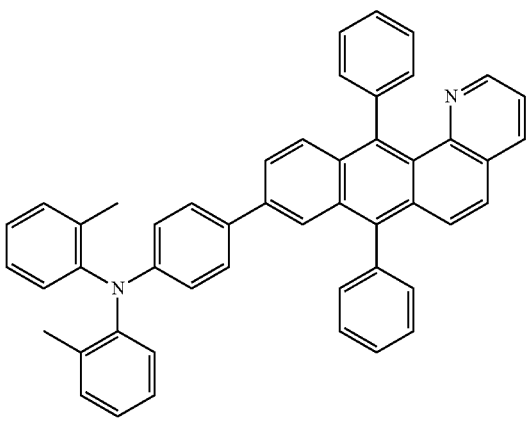
57
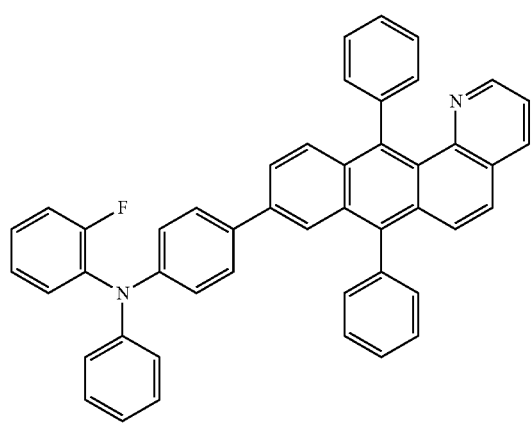
58
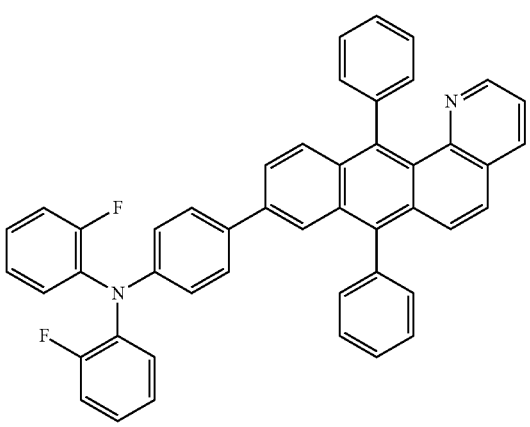

59
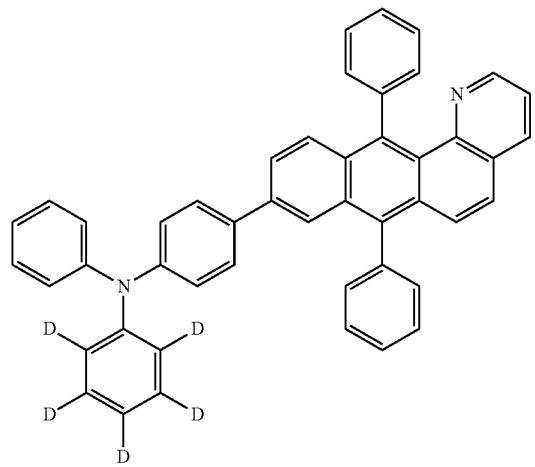
60
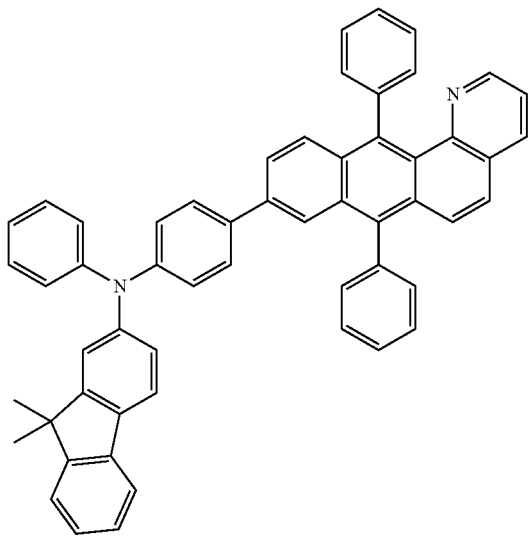
61
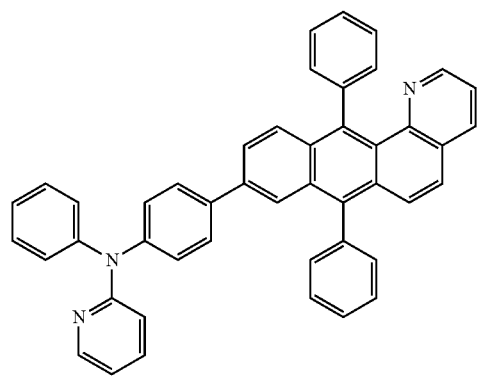
62
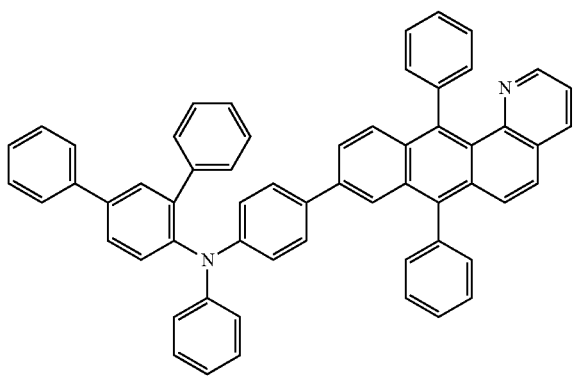
63
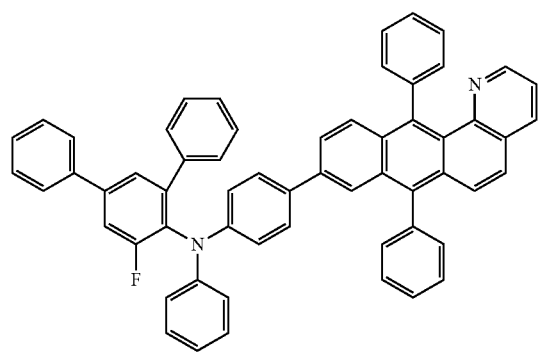
64
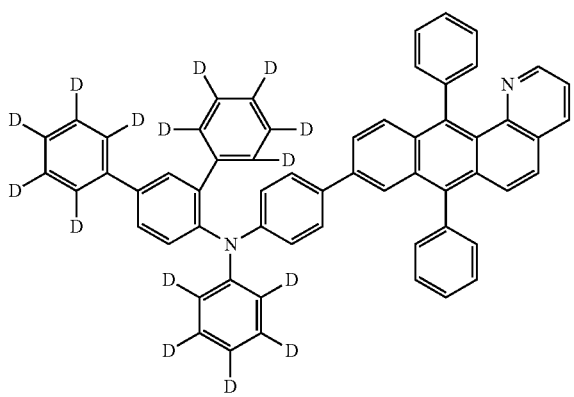

-continued
65 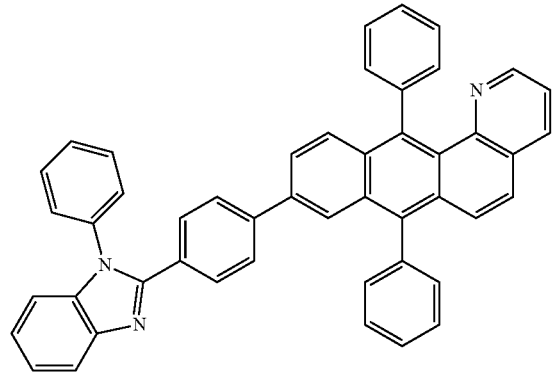
66 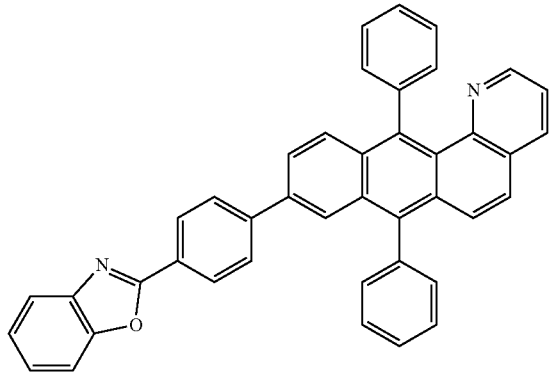
67 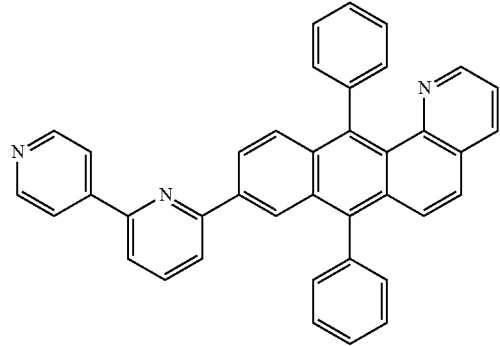
68 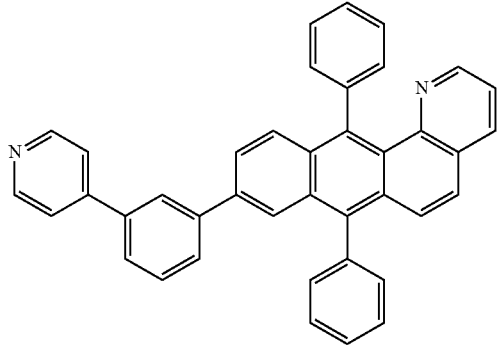
69 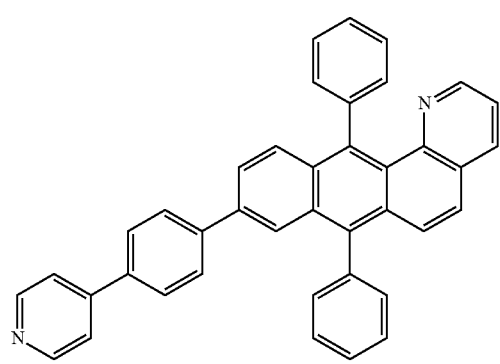
70 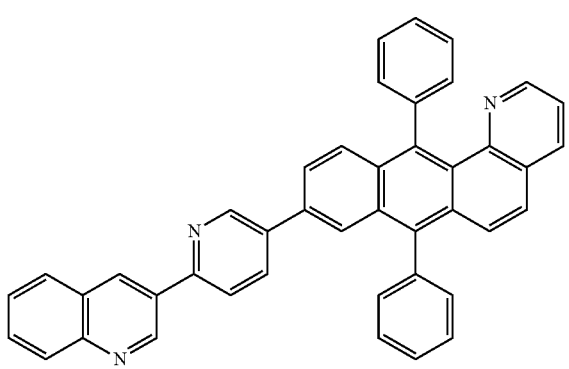
71 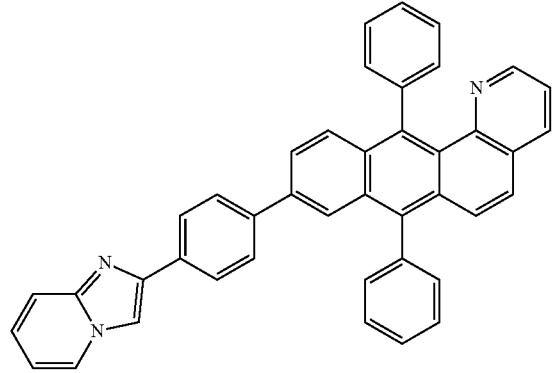
72 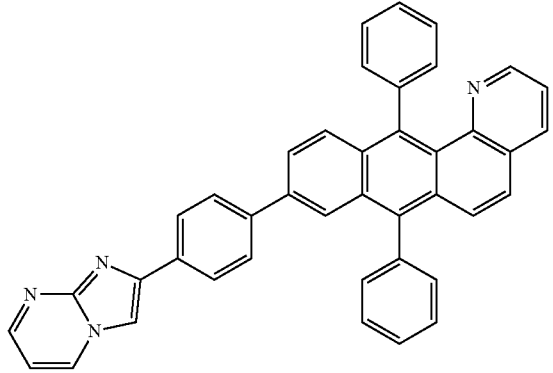

-continued
73
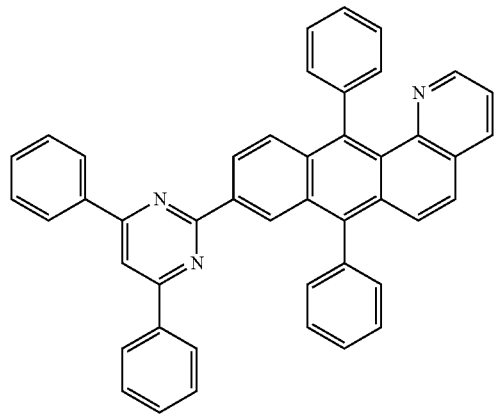
74
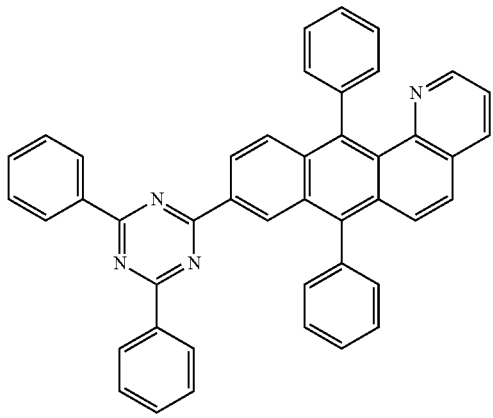
75
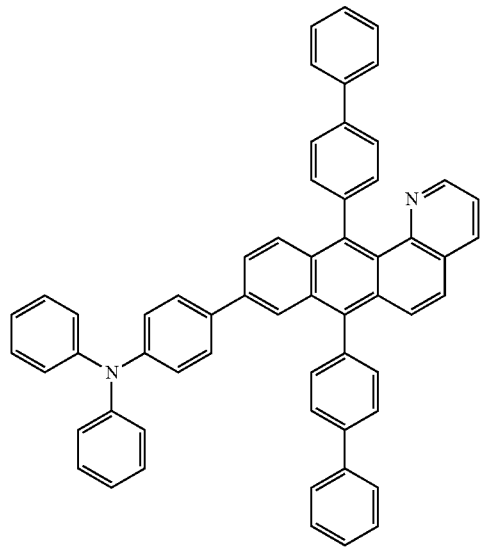
76
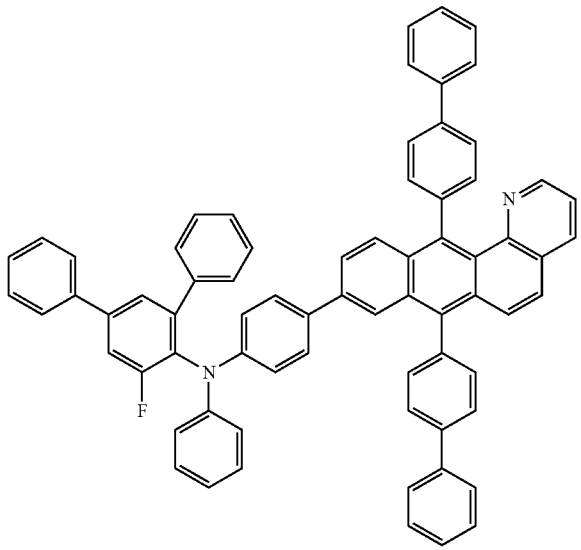
77
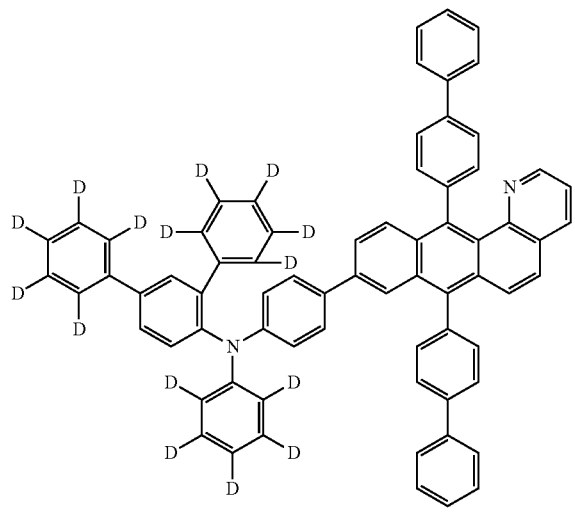
78
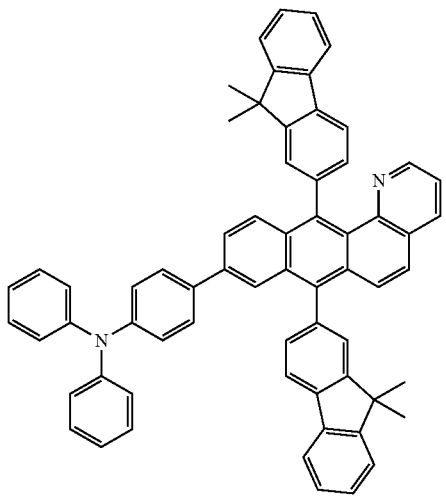

-continued

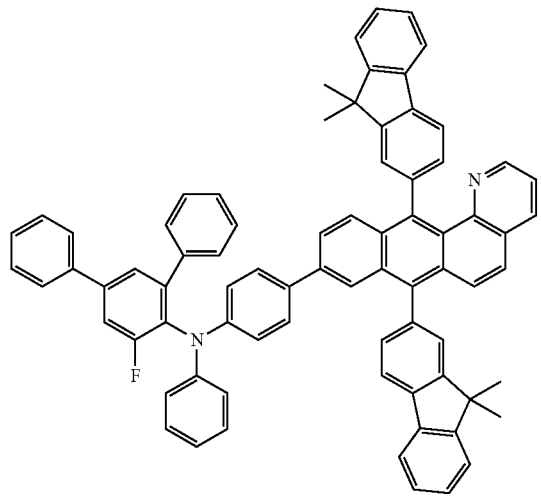
79

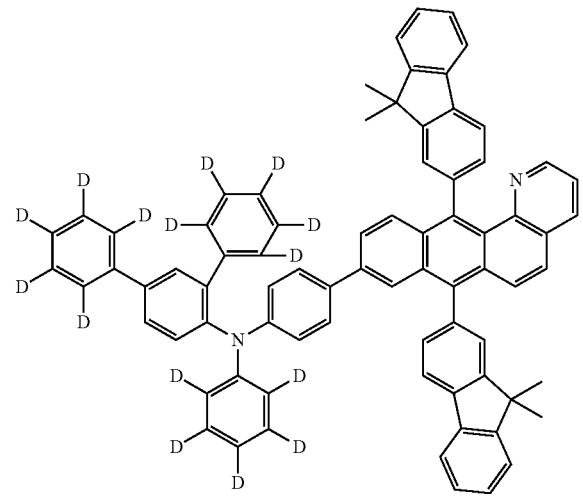
80

The term "substituted A" in the term "substituted or unsubstituted A (where A is an arbitrary substituent)" used herein refers to "a case in which one or more hydrogen atoms of the A are substituted with a deuterium atom, a halogen atom, a hydroxyl group, a cyano group, a nitro group, an amino group, hydrazine, hydrazone, a carboxyl group or a salt derivative thereof, a sulfonic acid group or a salt derivative thereof, a phosphoric acid group or a salt derivative thereof, a $C_1$-$C_{30}$ alkyl group, a $C_2$-$C_{30}$ alkenyl group, a $C_2$-$C_{30}$ alkynyl group, a $C_1$-$C_{30}$ alkoxy group, a $C_3$-$C_{30}$ cycloalkyl group, a $C_3$-$C_{30}$ cycloalkenyl group, a $C_5$-$C_{30}$ aryl group, a $C_5$-$C_{30}$ aryloxy group, a $C_5$-$C_{30}$ arylthio group, a $C_3$-$C_{30}$ heteroaryl group, a group represented by $N(Q_{101})(Q_{102})$, or a group represented by $Si(Q_{103})(Q_{104})(Q_{105})$. In this regard, $Q_{101}$ to $Q_{105}$ may each be independently a hydrogen atom, a deuterium atom, a halogen atom, a hydroxyl group, a cyano group, an amino group, a nitro group, a carboxyl group, a $C_1$-$C_{30}$ alkyl group, a $C_2$-$C_{30}$ alkenyl group, a $C_2$-$C_{30}$ alkynyl group, a $C_1$-$C_{30}$ alkoxy group, a $C_3$-$C_{30}$ cycloalkyl group, a $C_3$-$C_{30}$ cycloalkenyl group, a $C_5$-$C_{30}$ aryl group, a $C_5$-$C_{30}$ aryloxy group, a $C_5$-$C_{30}$ arylthio group, or a $C_3$-$C_{30}$ heteroaryl group.

For example, "substituted A" refers to a case in which one or more hydrogen atoms of the A are substituted with a deuterium atom, a halogen atom, a hydroxyl group, a cyano group, a nitro group, a carboxyl group, a methyl group, an ethyl group, a propyl group, a butyl group, a pentyl group, a methoxy group, an ethoxy group, a phenyl group, a biphenyl group, a pentalenyl group, an indenyl group, a naphthyl group, an azulenyl group, a heptalenyl group, an indacenyl group, an acenaphthyl group, a fluorenyl group, a spiro-fluorenyl group, a phenalenyl group, a phenanthrenyl group, a phenanthridinyl group, a phenanthrolinyl group, an anthryl group, a fluoranthenyl group, a triphenylenyl group, a pyrenyl group, a chricenyl group, a naphthacenyl group, a picenyl group, a perylenyl group, a pentaphenyl group, a hexacenyl group, a pyrrolyl group, an imidazolyl group, a benzoimidazolyl group, a pyrazolyl group, a pyridinyl group, a pyrazinyl group, a pyrimidinyl group, an imidazopyrimidinyl group, a pyridazinyl group, an indolyl group, an isoindolyl group, a pyrido indolyl group, an indazolyl group, a purinyl group, a quinolinyl group, a benzoquinolinyl group, a phthalazinyl group, a naphthyridinyl group, a quinoxalinyl group, a quinazolinyl group, a carbazolyl group, a phenazinyl group, a furanyl group, a benzofuranyl group, a dibenzofuranyl group, a thiophenyl group, a benzothiophenyl group, a dibenzothiophenyl group, a thiazolyl group, an isothiazolyl group, a benzothiazolyl group, an oxazolyl group, a benzooxazolyl group, an isooxazolyl group, an oxadiazolyl group, a triazolyl group, a triazinyl group, a tetrazolyl group, a group represented by $N(Q_{101})(Q_{102})$, or a group represented by $Si(Q_{103})(Q_{104})(Q_{105})$.

The unsubstituted $C_1$-$C_{30}$ alkyl group refers to a linear or branched saturated hydrocarbon group of alkane from which one hydrogen atom is removed. Examples of the unsubstituted $C_1$-$C_{30}$ alkyl group are methyl, ethyl, propyl, isobutyl, sec-butyl, pentyl, iso-amyl, hexyl, etc. A substituent of the substituted $C_1$-$C_{30}$ alkyl group may be any one of the substituents presented above where the term "substituted A" is described in detail.

The unsubstituted $C_2$-$C_{30}$ alkenyl group used herein refers to a group having at least one carbon-carbon double blond at the center or at a terminal of the unsubstituted $C_2$-$C_{30}$ alkyl group. Non-limiting examples of the unsubstituted $C_2$-$C_{30}$ alkenyl group are an ethenyl group, a propenyl group, a butenyl group, a pentenyl group, a hexenyl group, a heptenyl group, an octenyl group, a propadienyl group, an isoprenyl group, and an allyl group. A substituent of the substituted $C_2$-$C_{30}$ alkenyl group may be any one of the substituents presented above where the term "substituted A" is described in detail.

The unsubstituted $C_2$-$C_{30}$ alkynyl group used herein refers to a group having at least one carbon-carbon triple bond at the center or at a terminal of the unsubstituted $C_2$-$C_{30}$ alkyl group. Non-limiting examples of the unsubstituted $C_2$-$C_{30}$ alkynyl group are acetylenyl group, etc. A substituent of the substituted $C_2$-$C_{30}$ alkynyl group may be any one of the substituents presented above where the term "substituted A" is described in detail.

The unsubstituted $C_1$-$C_{30}$ alkoxy group used herein has a formula represented by —OY where Y is the unsubstituted $C_1$-$C_{30}$ alkyl group as defined above. Non-limiting examples of the unsubstituted $C_1$-$C_{30}$ alkoxy group are methoxy, ethoxy, isopropyloxy, butoxy, pentoxy, etc. A substituent of the substituted $C_1$-$C_{30}$ alkoxy group may be any one of the substituents presented above where the term "substituted A" is described in detail.

The unsubstituted $C_3$-$C_{30}$ cycloalkyl group used herein refers to a cyclic saturated hydrocarbon group. Non-limiting examples of the unsubstituted $C_3$-$C_{30}$ cycloalkyl group are cyclopropyl group, cyclobutyl group, cyclopentyl group, cyclohexyl group, cyclooctyl group, etc. A substituent of the substituted $C_1$-$C_{30}$ cycloalkyl group may be any one of the substituents presented above where the term "substituted A" is described in detail.

The unsubstituted $C_3$-$C_{30}$ cycloalkenyl group used herein refers to a cyclic unsaturated hydrocarbon group having one or more carbon double bonds that is not an aromatic cycle. Non-limiting examples of the unsubstituted $C_3$-$C_{30}$ cycloalkenyl group are a cyclopropenyl group, a cyclobutenyl group, a cyclopentenyl group, a cyclohexenyl group, a cycloheptenyl group, a 1,3-cyclohexadienyl group, a 1,4-cyclohexadienyl group, a 2,4-cycloheptadienyl group, a 1,5-cyclooctadienyl group, etc. A substituent of the substituted $C_3$-$C_{30}$ cycloalkenyl group may be any one of the substituents presented above where the term "substituted A" is described in detail.

The unsubstituted $C_5$-$C_{30}$ aryl group used herein refers to a monovalent group having a carbocyclic aromatic system in which the number of carbon atoms is 5 to 30, and may be a monocyclic group or a polycyclic group. If the unsubstituted $C_5$-$C_{30}$ aryl group is a polycyclic group, two or more rings contained in the unsubstituted $C_5$-$C_{30}$ aryl group may be fused. Non-limiting examples of the unsubstituted $C_5$-$C_{30}$ aryl group are a phenyl group, a pentalenyl group, an indenyl group, a naphthyl group, an azulenyl group, a heptalenyl group, an indacenyl group, an acenaphthyl group, a fluorenyl group, a spiro-fluorenyl group, a phenalenyl group, a phenanthrenyl group, an anthryl group, a fluoranthenyl group, a triphenylenyl group, a pyrenyl group, a chrysenyl group, a naphthacenyl group, a picenyl group, a perylenyl group, a pentaphenyl group, and a hexacenyl group. A substituent of the substituted $C_5$-$C_{30}$ aryl group may be any one of the substituents presented above where the term "substituted A" is described in detail.

The unsubstituted $C_5$-$C_{30}$ aryloxy group used herein refers to a monovalent group wherein a carbon atom of the $C_5$-$C_{30}$ aryl group is bonded via an oxygen linker (—O—). A substituent of the substituted $C_5$-$C_{30}$ aryloxy group may be any one of the substituents presented above where the term "substituted A" is described in detail.

The unsubstituted $C_5$-$C_{30}$ arylthio group used herein refers to a monovalent group wherein a carbon atom of the $C_5$-$C_{30}$ aryl group is bonded via a sulfur linker (—S—). Examples of the unsubstituted $C_5$-$C_{30}$ arylthio group are a phenylthio group, a naphthylthiol group, an indanylthiol group, and an indenyl thio group. A substituent of the substituted $C_5$-$C_{30}$ arylthio group may be any one of the substituents presented above where the term "substituted A" is described in detail.

The unsubstituted $C_3$-$C_{30}$ heteroaryl group used herein refers to a monovalent group that has at least one ring having one or more hetero atoms selected from the group consisting of nitrogen (N), oxygen (O), phosphorous (P), and sulfur (S), and may be a monocyclic or polycyclic group. If the unsubstituted $C_3$-$C_{30}$ heteroaryl group is a polycyclic group, two or more rings contained in the unsubstituted $C_3$-$C_{30}$ heteroaryl group may be fused. Examples of the unsubstituted $C_3$-$C_{30}$ heteroaryl group are a pyrrolyl group, an imidazolyl group, a pyrazolyl group, a pyridinyl group, a pyrazinyl group, a pyrimidinyl group, a pyridazinyl group, an isoindolyl group, an indolyl group, an indazolyl group, a purinyl group, a quinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzooxazolyl group, a benzoimidazolyl group, a furanyl group, a benzofuranyl group, a thiophenyl group, a benzothiophenyl group, a thiazolyl group, an isothiazolyl group, a benzothiazolyl group, an isoxazolyl group, an oxazolyl group, a triazolyl group, a tetrazolyl group, an oxadiazolyl group, a triazinyl group, a benzooxazolyl group, etc. A substituent of the substituted $C_3$-$C_{30}$ heteroaryl group may be any one of the substituents presented above where the term "substituted A" is described in detail.

The unsubstituted $C_1$-$C_{30}$ alkylene group used herein is a linear or branched divalent group of alkane from which two hydrogen atoms are removed. Examples of the unsubstituted $C_1$-$C_{30}$ alkylene group may be understood by referring to the examples of the unsubstituted $C_1$-$C_{30}$ alkyl group presented above. A substituent of the substituted $C_1$-$C_{30}$ may be any one of the substituents presented above where the term "substituted A" is described in detail.

The unsubstituted $C_5$-$C_{30}$ arylene used herein refers to a divalent group having a carbocyclic aromatic system having 5 to 30 carbon atoms, and the divalent group may be a monocyclic or polycyclic group. Examples of the unsubstituted $C_5$-$C_{30}$ arylene may be understood by referring to the examples of the unsubstituted $C_5$-$C_{30}$ aryl group. A substituent of the substituted $C_5$-$C_{30}$ arylene may be any one of the substituents presented above where the term "substituted A" is described in detail.

The heterocyclic compound represented by Formula 1 may be synthesized by using known organic synthesis methods, which may be obvious to one of ordinary skill in the art in view of the following Examples.

The heterocyclic compound represented by Formula 1 may be used in an organic light-emitting diode.

An organic light-emitting diode according to an embodiment of the present invention includes a first electrode; a second electrode facing the first electrode; and a first layer interposed between the first electrode and the second electrode, wherein the first layer includes the heterocyclic compound represented by Formula 1.

The organic light-emitting diode may further include, between the first electrode and the second electrode, in addition to the first layer described above, a hole injection layer, a hole transport layer, a function layer having a hole injection function and, a hole transport function, an emission layer, a hole blocking layer, an electron injection layer, an electron transport layer, a function layer having an electron injection function and an electron transport function, or a combination of two or more thereof. For example, the organic light-emitting diode may have a structure of first electrode/hole injection layer/hole transport layer/first layer including the heterocyclic compound (that is, functioning as an emission layer)/electron transport layer/electron injection layer/second electrode, but the structure of the organic light-emitting diode is not limited thereto.

One or more layers between the first electrode and second electrode may be formed by using a deposition process or a wet process.

The term "wet process" used herein refers to a process in which a material is mixed with a solvent to prepare a mixture, and the mixture is provided on a substrate, followed by drying and/or heat treating so as to remove at least a portion of the solvent, thereby forming a film including the material on the substrate.

For example, the first layer may be formed by using a typical vacuum deposition method. Alternatively, a mixture including the heterocyclic compound and a solvent may be provided on a first layer formation region (for example, on an upper portion of a hole transport layer) by spin coating, spraying, ink-jet printing, dipping, casting, Gravia coating, bar coating, roll coating, wire bar coating, screen coating, flexo coating, offset coating, or laser transferring, and then, the mixture provided on the first layer formation region is dried and/or heat treated to remove at least a portion of the solvent, thereby forming the first layer.

Alternatively, after a first layer is formed on a base film by using the wet process as described above, the first layer may be transferred to a first layer formation region (for example, an upper portion of the hole transport layer) by using, for example, a laser.

The first layer may include at least one selected from the group consisting of an electron injection layer, an electron transport layer, a layer having an electron injection function and an electron transport function, and an emission layer, but is not limited thereto.

If the first layer is an emission layer, the first layer may include only the heterocyclic compound, or both the heterocyclic compound and a compound that is different from the heterocyclic compound.

For example, the first layer is an emission layer, and the heterocyclic compound included in the first layer may be used as a fluorescent host or a phosphorescent host. In this case, the first layer may further include a fluorescent dopant or a phosphorescent dopant. In detail, the first layer may be an emission layer including the heterocyclic compound functioning as a fluorescent host, and a fluorescent dopant, and alternatively, may be an emission layer including the heterocyclic compound functioning as a phosphorescent host, and a phosphorescent dopant. Alternatively, the first layer may be an emission layer, and the heterocyclic compound included in the first layer may be used as a fluorescent dopant. In this case, the first layer may further include a fluorescent host or a phosphorescent host. In detail, the first layer may be an emission layer including the heterocyclic compound functioning as a fluorescent dopant, and a phosphorescent host or fluorescent host.

Also, the emission layer included in the organic light-emitting diode may further include at least one selected from the group consisting of an anthracene-based compound, an arylamine-based compound, and a styryl-based compound.

Also, the first layer included in the organic light-emitting diode may instead be an electron transport layer, and the electron transport layer may include the heterocyclic compound and a metal-containing material. In this case, the metal-containing material may include a Li complex.

Also, the first layer included in the organic light-emitting diode is an electron transport layer, an emission layer is additionally interposed between the first electrode and the second electrode, and the emission layer includes at least one region selected from the group consisting of a red light-emitting region, a green light-emitting region, a blue light-emitting region, and a white light-emitting region, wherein the at least one region selected from the group consisting of the red light-emitting region, green light-emitting region, the blue light-emitting region, and the white light-emitting region may include a phosphorescent compound. The red light-emitting region, the green light-emitting region, the blue light-emitting region, and the white light-emitting region may be patterned by using known methods so as to embody full color images or white light emission. The phosphorescent compound may be selected from known phosphorescent hosts and phosphorescent dopants. A phosphorescent dopant may be, for example, an organometallic complex including Ir, Pt, Os, Re, Ti, Zr, Hf, or a combination of two or more thereof.

FIG. 1 is a schematic view of an organic light-emitting diode 10 according to an embodiment of the present invention. Hereinafter, with reference to FIG. 1, the structure of an organic light-emitting diode according to an embodiment of the present invention, and a method of manufacturing the organic light-emitting diode, according to an embodiment of the present invention, will be described in detail.

Figure 2:
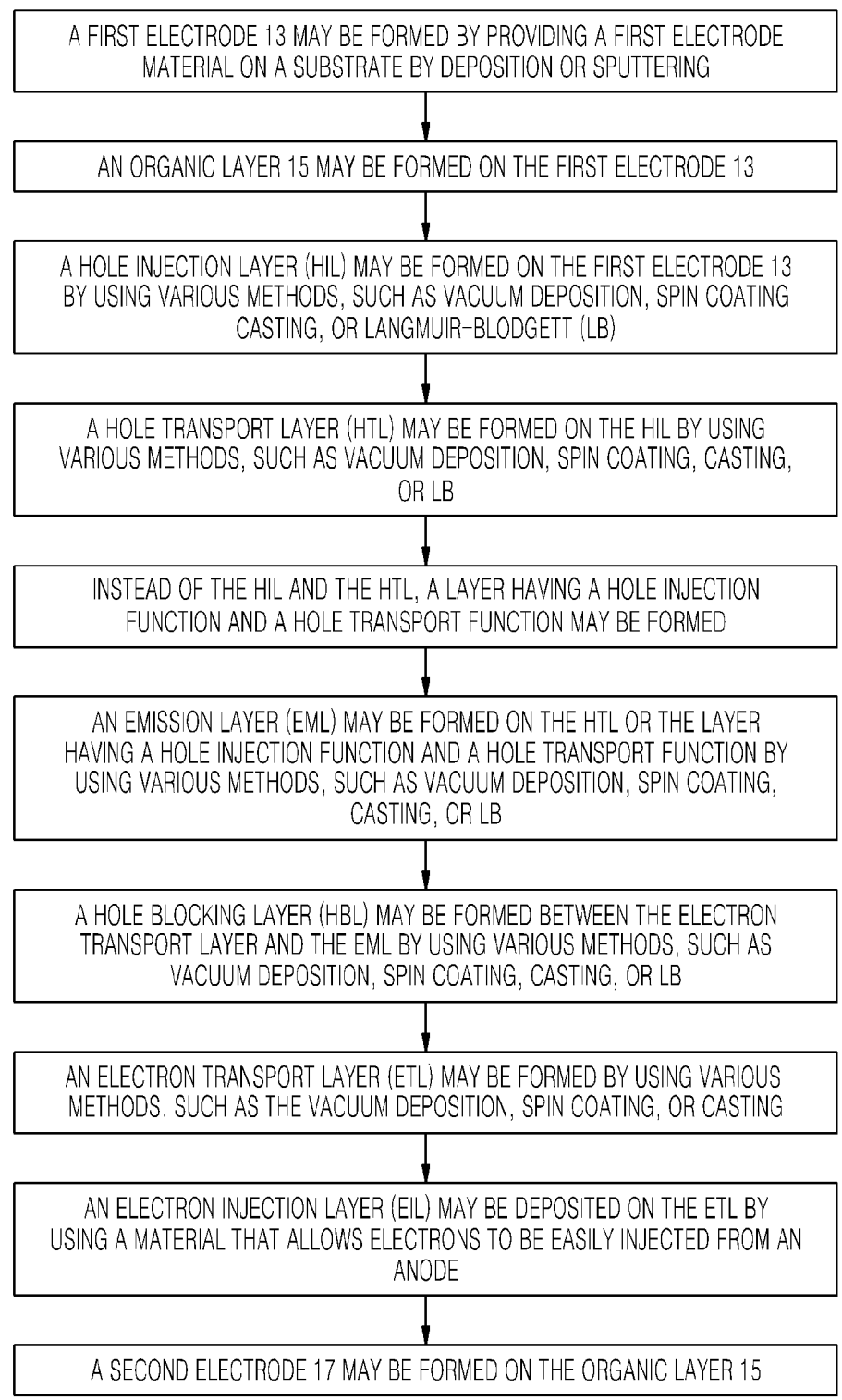
FIG. 2 is a flowchart showing a method of manufacturing an organic light-emitting diode according to an embodiment of the present invention.

FIG. 2 shows a method of manufacturing an organic light-emitting diode according to an embodiment of the present invention.

The organic light-emitting diode 10 sequentially includes a substrate 11, a first electrode 13, an organic layer 15, and a second electrode 17.

The substrate 11 may be any one of various substrates that are used in a known organic light-emitting device, and may be a glass substrate or a transparent plastic substrate with excellent mechanical strength, thermal stability, transparency, surface smoothness, ease of handling, and water repellency.

The first electrode 13 may be formed by providing a first electrode material on a substrate by deposition or sputtering. If the first electrode 13 is an anode, to allow holes to be injected thereinto easily, the first electrode material may be selected from materials having a high work function. Also, the first electrode 13 may be a reflection electrode or a transmission electrode. The first electrode material may be a transparent and highly conductive material, such as an indium tin oxide (ITO), or an indium zinc oxide (IZO), tin oxide ($SnO_2$), zinc oxide (ZnO), etc. Alternatively, if magnesium (Mg), aluminum (Al), aluminum-lithium (Al—Li), calcium (Ca), magnesium-indium (Mg—In), magnesium-silver (Mg—Ag) etc, are used as the first electrode material, the first electrode 13 may be formed as a reflection electrode.

The organic layer 15 may be formed on the first electrode 13. The term "organic layer" used herein refers to a layer interposed between the first electrode and the second electrode, and the organic layer may not be limited to a layer that includes only an organic material. For example, the organic layer may also include a metallic complex.

The organic layer 15 may include the first layer including the heterocyclic compound represented by Formula 1, and may further include at least one layer selected from the group consisting of a hole injection layer, a hole transport layer, a function layer having a hole injection function and a hole transport function, an emission layer, a hole blocking layer, an electron transport layer, and an electron injection layer. For example, if the first layer is an electron transport layer, the organic layer 15 may include, in addition to the first layer functioning as the electron transport layer, a hole injection layer, a hole transport layer, an emission layer, and an electron injection layer. However, the structure of the organic layer 15 is not limited thereto.

The hole injection layer (HIL) may be formed on the first electrode 13 by using various methods, such as vacuum deposition, spin coating, casting, or Langmuir-Blodgett (LB).

If the HIL is formed by vacuum deposition, the deposition conditions may vary according to a material that is used to form the HIL, and the structure and thermal characteristics of the HIL. For example, the deposition conditions may include a deposition temperature of about 100 to about 500 Å, a vacuum pressure of about $10^{18}$ to about $10^{-3}$ torr, and a deposition rate of about 0.01 to about 100 Å/sec. However, the deposition conditions are not limited thereto.

When the HIL is formed using spin coating as a wet process, coating conditions may vary according to the material used to form the HIL, and the structure and thermal properties of the HIL. For example, a coating speed may be from about 2000 rpm to about 5000 rpm, and a temperature at which a heat treatment is performed to remove a solvent after coating may be from about 80 Å to about 200 Å. However, the coating conditions are not limited thereto.

A hole injection layer material may be any one of known hole injecting materials. Non-limiting examples of the hole injection layer material are a N,N'-diphenyl-N,N'-bis-[4-(phenyl-m-tolyl-amino)-phenyl]-biphenyl-4,4'-diamine (DNTPD), a phthalocyanine compound, such as copper phthalocyanine, 4,4',4"-tris(3-methylphenylphenylamino) triphenylamine (m-MTDATA), N,N'-di(1-naphthyl)-N,N'-diphenylbenzidine (NPB), 4,4'4"-tris(N,N-diphenylamino) triphenylamine (TDATA), 4,4',4"-tris{N,-(2-naphthyl)-N-phenylamino}-triphenylamine (2T-NATA), polyaniline/dodecylbenzenesulfonic acid (PANI/DBSA), poly(3,4-ethylenedioxythiophene)/poly(4-styrenesulfonate) (PEDOT/PSS), polyaniline/camphor sulfonic acid (PANI/CSA), and polyaniline/poly(4-styrenesulfonate) (PANI/PSS).

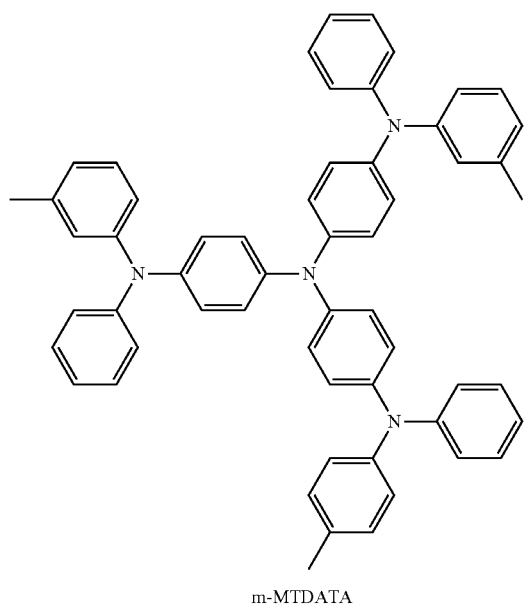

m-MTDATA

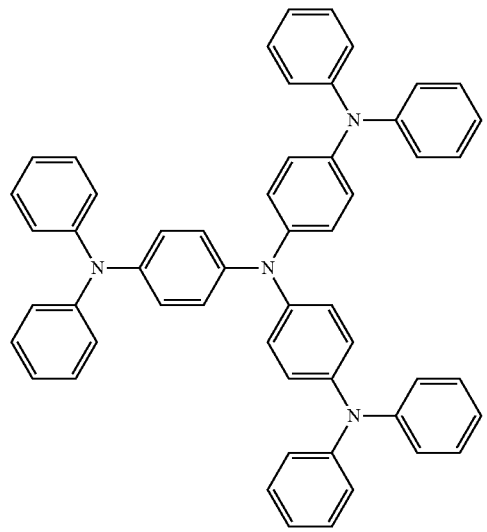

TDATA

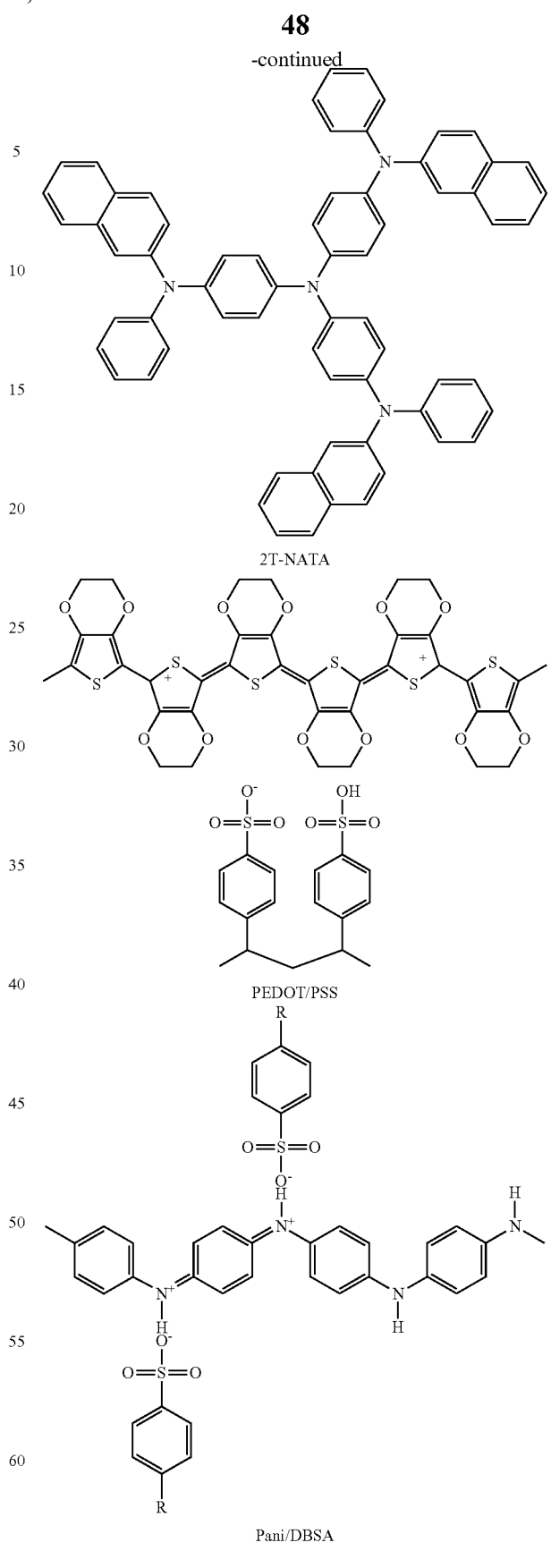

2T-NATA

PEDOT/PSS

Pani/DBSA

The HIL may have a thickness of about 100 Å to about 10,000 Å, for example, a thickness of about 100 Å to about 1,000 Å. When the thickness of the HIL is within these ranges, the HIL may have satisfactory hole injection characteristics without an increase in driving voltage.

Then, the hole transport layer (HTL) may be formed on the HIL by using various methods, such as vacuum deposition, spin coating, casting, or LB. If the HTL is formed on the HIL by vacuum deposition or spin coating, the deposition or coating conditions may be similar to those applied to form the HIL, although the deposition or coating conditions may vary according to the material that is used to form the HTL.

The HTL material may be any one of known hole transport materials. Non-limiting examples thereof are a carbazole derivative, such as N-phenylcarbazole or polyvinylcarbazole; an amine derivative having an aromatic condensation ring, such as N,N'-bis(3-methylphenyl)-N,N'-diphenyl-[1,1-biphenyl]-4,4'-diamine (TPD), or 4,4'-bis[N-(1-naphthyl)-N-phenylamino]biphenyl α (-NPD); and a triphenylamine-based material, such as 4,4',4''-tris(N-carbazolyl) triphenylamine (TCTA).

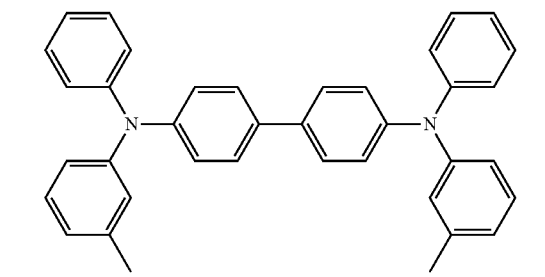

TPD

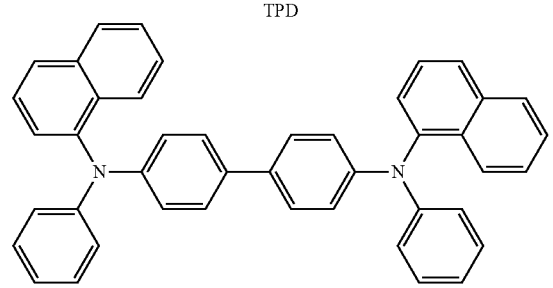

α-NPD

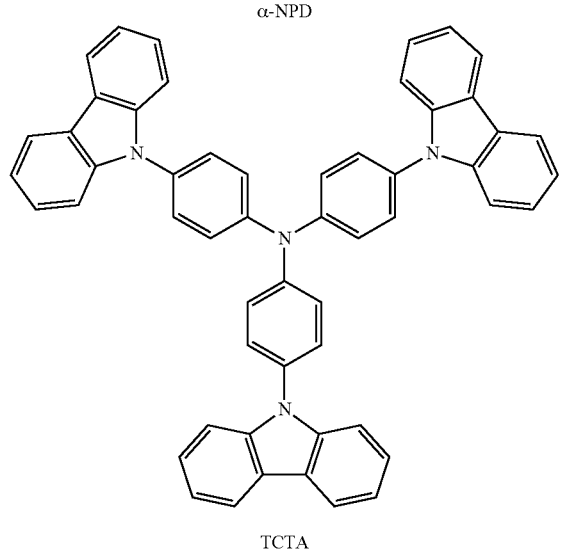

TCTA

The HTL may have a thickness of about 50 Å to about 1000 Å, for example, a thickness of about 100 Å to about 800 Å. When the thickness of the HTL is within the above ranges, the HTL may have satisfactory hole transport characteristics without a substantial increase in driving voltage.

According to another embodiment, instead of the HIL and the HTL, a layer having a hole injection function and a hole transport function may be formed. A material for forming the layer having a hole injection function and a hole transport function may be selected from known materials.

At least one selected from the group consisting of the HIL, the HTL, and the layer having a hole injection function and a hole transport function may include, in addition to known hole injection materials and hole transport materials, a charge-generation material for improving conductivity of a film.

The charge-generation material may be, for example, a p-dopant. Non-limiting examples of the p-dopant are a quinine derivative, such as tetracyanoquinonedimethein (TCNQ), or 2,3,5,6-tetra fluoro-tetracyano-1,4-benzoquinonedimethane (f4TCNQ); a metallic oxide, such as tungsten oxide or molybdenum oxide; and a cyano group-containing compound, such as Compound 100 below.

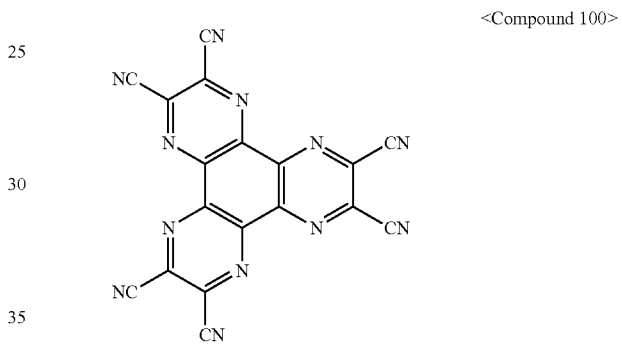

<Compound 100>

If the at least one selected from the group consisting of the HIL, the HTL, and the layer having a hole injection function and a hole transport function may include the charge-generation material, the charge-generation material may be homogeneously or non-homogeneously dispersed in the layers.

The emission layer (EML) may be formed on the HTL or the layer having a hole injection function and a hole transport function by using various methods, such as vacuum deposition, spin coating, casting, or LB. If the EML is formed by vacuum deposition or spin coating, the deposition or coating conditions may be similar to those applied to form the HIL, although the deposition or coating conditions may vary according to the material that is used to form the EML.

As an emission layer material, at least one selected from the group consisting of the heterocyclic compound represented by Formula 1 and a known light-emission material (including a host and a dopant) may be used. If the emission layer includes the heterocyclic compound represented by Formula 1, a known phosphorescent host, fluorescent host, phosphorescent dopant, or fluorescent dopant may be further used in addition to the heterocyclic compound represented by Formula 1. The heterocyclic compound may function as a phosphorescent host, a fluorescent host, or a fluorescent dopant.

For example, as a known host, Alq$_3$, 4,4'-N,N'-dicabazole-biphenyl (CBP), poly(n-vinylcabazole) (PVK), 9,10-di (naphthalene-2-yl)anthracene (ADN), TCTA, 1,3,5-tris(N-phenyl benzimidazole-2-yl)benzene (TPBI), 3-tert-butyl-9, 10-di(naphth-2-yl) anthracene (TBADN), distyrylarylene (DSA), and E3 may be used, but an example thereof is not limited thereto.

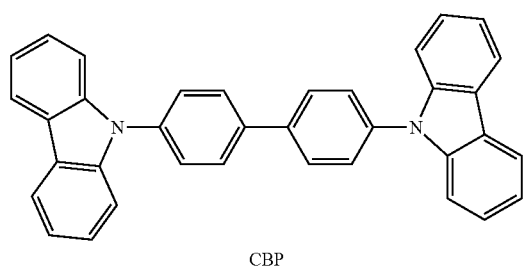

CBP

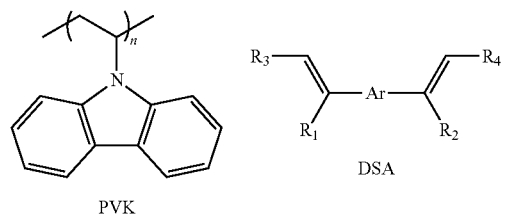

PVK  DSA

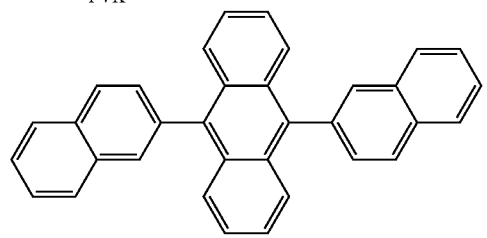

ADN

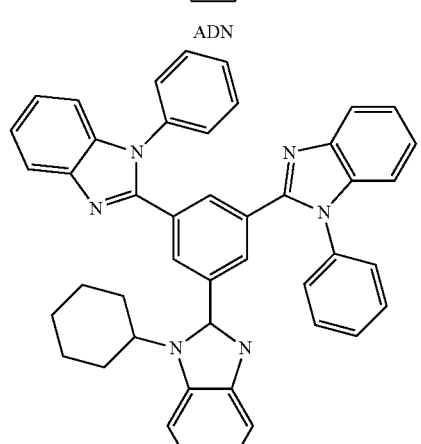

TBPI

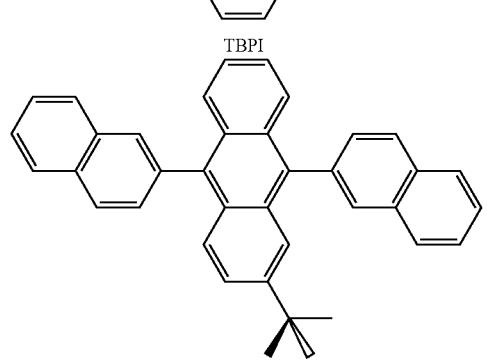

TBADN

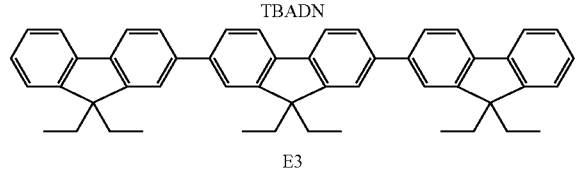

E3

As a dopant, at least one of a fluorescent dopant and a phosphorescent dopant may be used. The phosphorescent dopant may include Ir, Pt, Os, Re, Ti, Zr, Hf, or an organo metallic complex including a combination of two or more thereof, but is not limited thereto.

Also, as a red dopant, PtOEP (a structure thereof is illustrated below), Ir(piq)$_3$ (a structure thereof is illustrated below), Btp$_2$Ir(acac) (a structure thereof is illustrated below) may be used. However, the red dopant is not limited thereto.

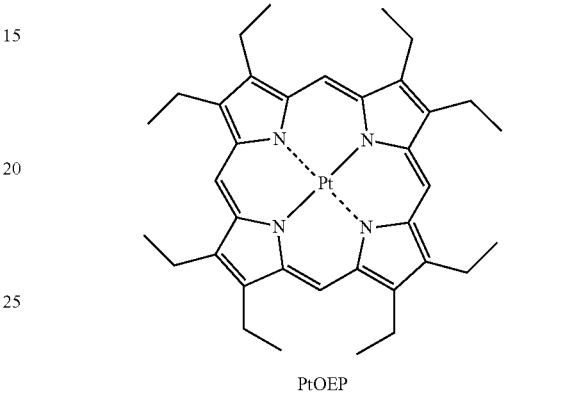

PtOEP

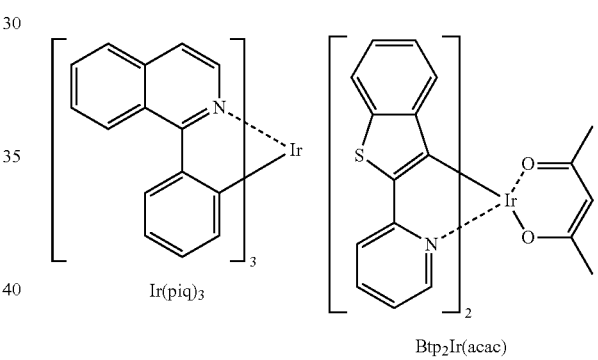

Ir(piq)$_3$   Btp$_2$Ir(acac)

Also, as a green dopant, Ir(ppy)$_3$ (ppy=phenylpyridine, a structure thereof is illustrated below), Ir(ppy)$_2$(acac) (a structure thereof is illustrated below), Ir(mppy)$_3$ (a structure thereof is illustrated below) etc. may be used, but are not limited thereto.

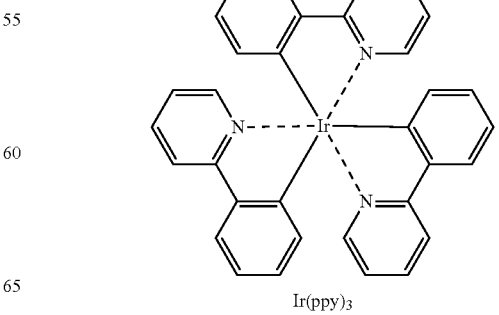

Ir(ppy)$_3$

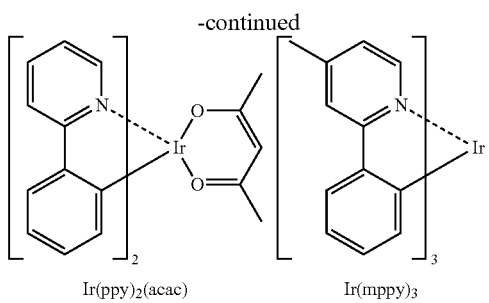

As a blue dopant, F₂Irpic (a structure thereof is illustrated below), (f₂ ppy)₂Ir(tmd) (a structure thereof is illustrated below), Ir(dfppz)₃ (a structure thereof is illustrated below), DPVBi (a structure thereof is illustrated below), DPAVBi (4,4'-bis(4-diphenylaminostaryl)biphenyl), 2,5,8,11-tetra-tert-butyl perylene (TBPe), etc. may be used, but are not limited thereto.

nescence characteristics may be obtained without a substantial increase in driving voltage.

If the EML includes a phosphorescent dopant, to prevent diffusion of a triple exciton or a hole into the electron transport layer, a hole blocking layer (HBL) (not shown in FIG. 1) may be formed between the electron transport layer and the EML by using various methods, such as vacuum deposition, spin coating, casting, or LB. If the HBL is formed by vacuum deposition or spin coating, the deposition or coating conditions may be similar to those applied to form the HIL, although the deposition or coating conditions may vary according to the material that is used to form the HBL. As a HBL material, any one of known hole blocking materials may be used, and examples thereof are an oxadiazole derivative, a triazole derivative, a phenanthroline derivative, etc.

A thickness of the HBL may be from about 50 Å to about 1000 Å, for example, about 100 Å to about 300 Å. If the thickness of the HBL is within the ranges described above, excellent hole blocking characteristics may be obtained without a substantial increase in driving voltage.

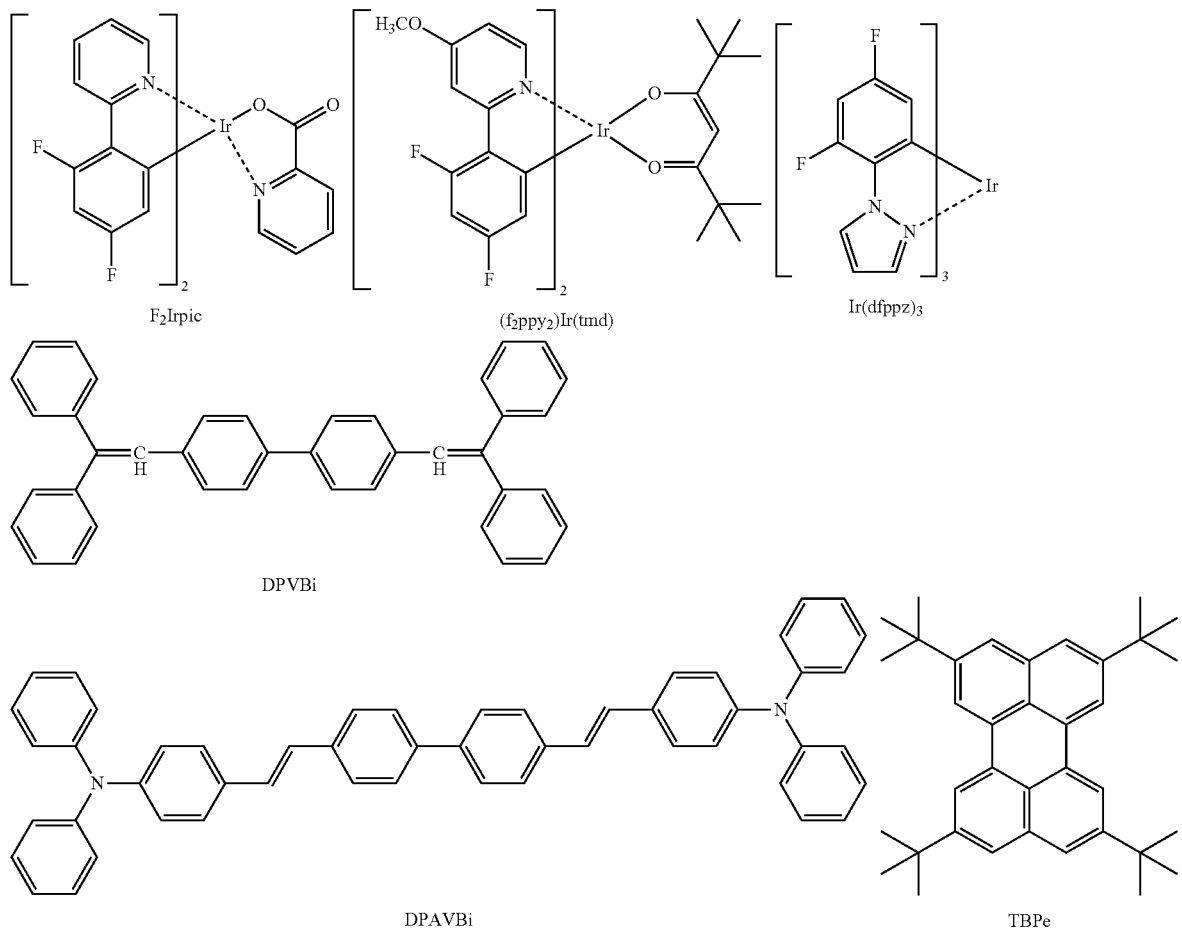

If the EML includes a host and a dopant, an amount of the dopant may be from about 0.01 to about 15 pans by weight based on about 100 parts by weight of the host, but is not limited thereto.

A thickness of the EML may be from about 100 Å to about 1000 Å, for example, about 200 Å to about 600 Å. If the thickness of the EML is within these ranges, excellent lumi- Then, the electron transport layer (ETL) may be formed by using various methods, such as the vacuum deposition, spin coating, or casting. If the ETL is formed by vacuum deposition or spin coating, the deposition or coating conditions may be similar to those applied to form the HIL, although the deposition or coating conditions may vary according to the material that is used to form the ETL.

As an ETL material, the heterocyclic compound described above may be used. Alternatively, a known electron transport material may instead be used as the ETL material. Examples of the known electron transport material are a quinoline derivative, such as, Alq$_3$(tris(8-quinolinolate)aluminum), 2,9-dimethyl-4,7-diphenyl-1,10-phenanthroline (BCP), 4,7-diphenyl-1,10-phenanthroline (Bphen), 3-(4-Biphenylyl)-4-phenyl-5-tert-butylphenyl-1,2,4-triazole (TAZ), 4-(naphthalen-1-yl)-3,5-diphenyl-4H-1,2,4-triazole (NTAZ), 2-(4-biphenylyl)-5-(4-tert-butylphenyl)-1,3,4-oxadiazole (tBu-PBD), BAlq (a structure thereof is illustrated below), and beryllium bis(benzoquinolin-10-olate) (Bebq$_2$), but are not limited thereto.

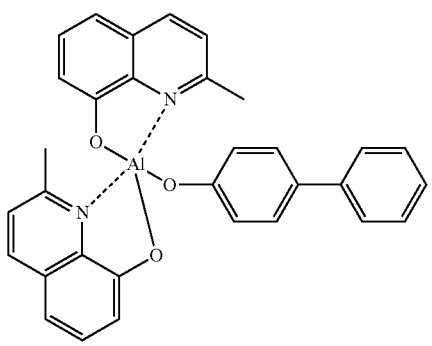

BAlq

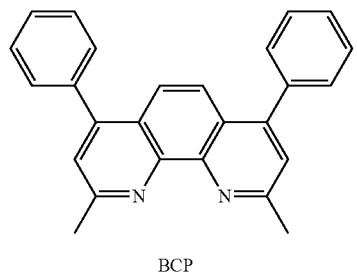

BCP

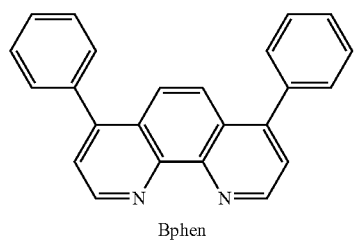

Bphen

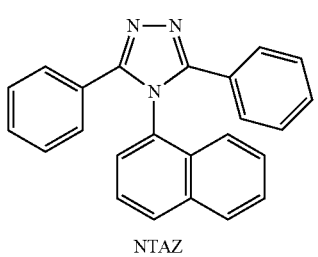

NTAZ

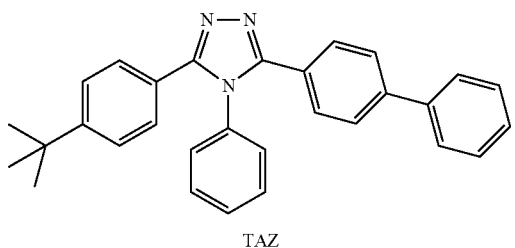

TAZ

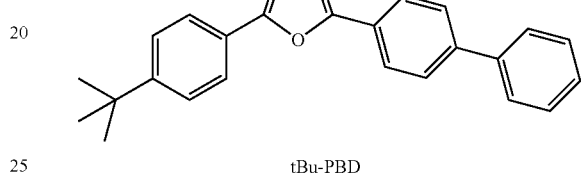

tBu-PBD

A thickness of the ETL may be from about 100 Å to about 1000 Å, for example, about 150 Å to about 500 Å. If the thickness of the ETL is within the ranges described above, satisfactory electron transporting characteristics may be obtained without a substantial increase in driving voltage.

According to another embodiment, the ETL may instead include an electron transporting organic compound and a metal-containing material. Non-limiting examples of the electron transporting organic compound are 9,10-di(naphthalene-2-yl)anthracene (ADN), and an anthracene-based compound, such as Compounds 101 and 102, but are not limited thereto.

<Compound 101>

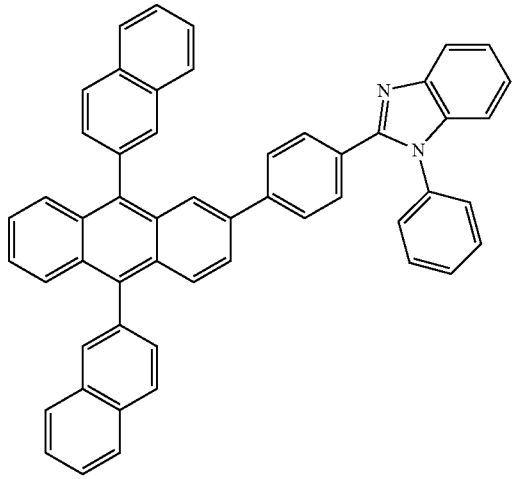

<Compound 102>

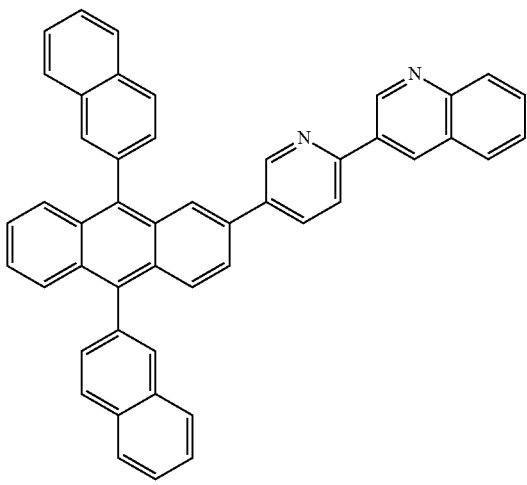

The metal-containing material may include a Li complex. Non-limiting examples of the Li complex are lithium quinolate (LiQ) and Compound 103 illustrated below.

<Compound 103>

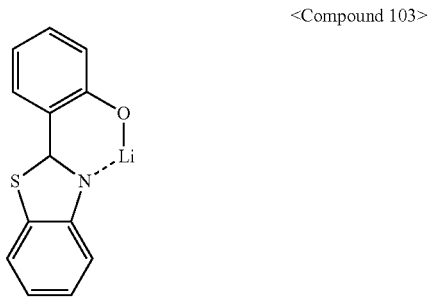

Also, the electron injection layer (EIL) may be deposited on the ETL by using a material that allows electrons to be easily injected from an anode. The material is not particularly limited.

As the material, any one of known ETL materials including, for example, LiF, NaCl, CsF, $Li_2O$, and BaO may be used. The deposition conditions for the ETL may be similar to those applied to form the HIL, although the deposition or coating conditions may vary according to the material that is used to form the ETL.

A thickness of the EIL may be from about 1 Å to about 100 Å, for example, about 3 Å to about 90 Å. If the thickness of the EIL is within the ranges described above, excellent electron injection characteristics may be obtained without a substantial increase in driving voltage.

The second electrode 17 may be formed on the organic layer 15. The second electrode 17 may be a cathode as an electron injection electrode. In this regard, a low work function metal, alloy, electrically conductive compound, and a mixture thereof may be used as a metal for forming the second electrode. In detail, lithium (Li), magnesium (Mg), aluminum (Al), aluminum-lithium (Al—Li), calcium (Ca), magnesium-indium (Mg—In), magnesium-silver (Mg—Ag), etc. may be formed as a thin film for use as a transmission electrode. Also, if the organic light-emitting diode is used in a top-emission light-emitting device, a transmission electrode may be formed using ITO or IZO.

If the first layer included in the organic light-emitting diode is a hole injection layer, a hole transport layer, or a function layer having a hole injection function and a hole transport function, the first layer may further include, in addition to the heterocyclic compound represented by Formula 1, the charge-generation material described above. Alternatively, if the first layer included in the organic light-emitting diode is an emission layer, the first layer may further include, in addition to the heterocyclic compound represented by Formula 1, the phosphorescent dopants described above.

The organic light-emitting diode may be included in a flat display device including a transistor. Accordingly, an embodiment of the present invention provides a flat display device including: a transistor including a source, a drain, a gate, and an active layer, and the organic light-emitting diode described above, wherein the source or the drain is electrically connected to the first electrode of the organic light-emitting diode. The active layer of the transistor may be an amorphous silicon layer, a crystalloid silicon layer, an organic semiconductor layer, or an oxide semiconductor layer, and is not limited thereto.

Hereinafter, organic light-emitting diodes according to one or more embodiments of the present invention will be described in detail with reference to Synthesis Examples and Examples. However, the one or more embodiments of the present invention are not limited to Synthesis Examples and Examples.

EXAMPLES

Synthesis Example 1

Synthesis of Intermediate I-6

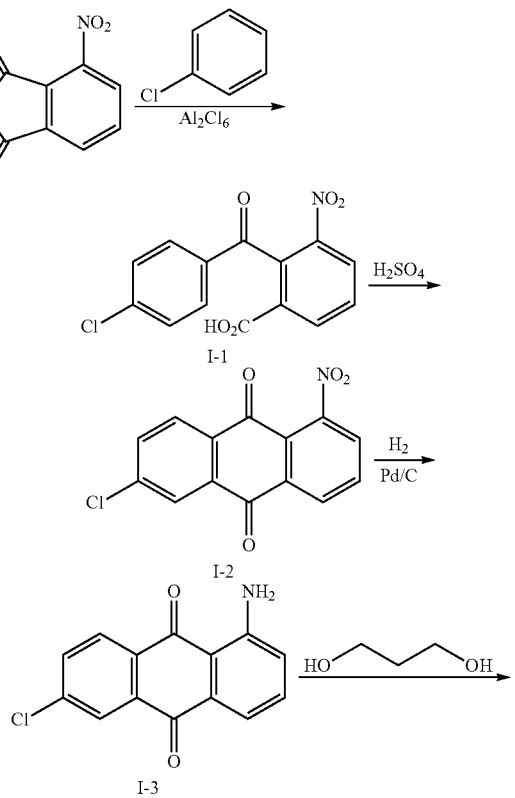

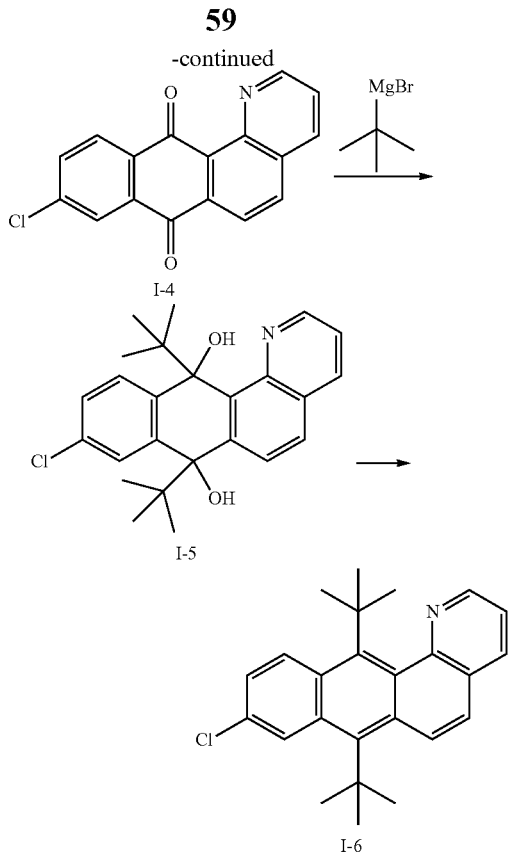

Synthesis of Intermediate I-1

19.311 g (100 mmol) of 3-nitrophthalicunhydride was dissolved in 56.28 g (500 mmol) of chlorobenzene, and 26.668 (100 mmol) of $Al_2Cl_6$ was added thereto until a hydrochloric acid was not generated. The mixture was stirred at a temperature of 100° C. for 8 hours. The resultant solution was cooled to room temperature and iced water was added thereto and distilled to remove chlorobenzene therefrom, and the residual solution was filtered and washed with warm water. Extraction was performed thereon with a 20% sodium carbonate solution, and a sulfuric acid was added thereto to generate a solid. The generated solid was filtered to obtain 12.532 g (Yield: 41%) of Intermediate I-1. The formed compound was confirmed by liquid chromatography-mass spectroscopy (LC-MS).

$C_{14}H_8ClNO_5$ calculated value: 305.6; actually measured value: 306.6

Synthesis of Intermediate I-2

A 6 equivalent amount of a sulfuric acid was added to 12.532 g (41 mmol) of Intermediate I-1 and the mixture was stirred at a temperature of 150° C. for 4 hours. The resultant solution was cooled to room temperature and a 20% sodium carbonate solution was added thereto and filtered, followed by drying at a temperature of 110° C. Soxhlet extraction was performed thereon with benzene, followed by drying, thereby obtaining 11.439 g (Yield: 97%) of Intermediate I-3. The formed compound was confirmed by LC-MS.

$C_{14}H_9ClNO_4$ calculated value: 287.6; actually measured value: 288.5

Synthesis of Intermediate I-3

11.439 g (39.7 mmol) of Intermediate I-2 and 5% Pd/C were dissolved in methanol, and the resultant solution was stirred at room temperature for 4 hours while a hydrogen gas was supplied. The reaction solution was filtered, and then the residual solution was concentrated and the residual was separation-purified by silica gel column chromatography to obtain 10.014 g (Yield: 97.7%) of Intermediate I-4. The formed compound was confirmed by LC-MS.

$C_{14}H_8ClNO_2$ calculated value: 257.6; actually measured value: 258.6

Synthesis of Intermediate I-4

10.014 g (38.8 mmol) of Intermediate I-3 and 2.952 g (38.8 mmol) of 1,3-propane diol were dissolved in 20 ml of mesitylene. 0.240 g (0.4 mmol) of chloroiridiumhydroxide, 0.720 g (12 mmol) of 2,2'-bis-diphenylphosphino-1,1'-binaphtyl (BINAP), and 1.275 g (12 mmol) of sodium carbonate were added to the solution and stirred at a temperature of 170° C. for 15 hours. The remaining solution was concentrated and the residual was separation-purified by silica gel column chromatography to obtain 11.395 g (Yield: 96%) of Intermediate I-4. The formed compound was confirmed by LC-MS.

$C_{17}H_8ClNO_2$ calculated value: 293.7; actually measured value: 294.7

Synthesis of Intermediate I-5

4.23 g (20.4 mmol) of tert-butylmagnesiumbromide was completely dissolved in 100 mL of dried THF, and then n-butyllithium (8.2 ml, 2.5M solution in hexane) was very slowly added thereto at a temperature of −78° C. After 1 hour, 11.395 g (37.2 mmol) of Intermediate I-4 was added thereto. After 30 minutes, a cooling vessel was removed and the resultant mixture was reacted at room temperature for 3 hours. After a reaction was finished, an $NH_4Cl$ aqueous solution was added thereto, followed by extraction with ethyether. The extracted reaction product was dried and concentrated with anhydrous magnesium sulfate, and then a small amount of ethylether was added thereto and stirred, and then ethanol was added thereto and stirred. Then, the reaction product was filtered and dried to obtain I-5 16.758 g (Yield: 95%) of Intermediate. The formed compound was confirmed by LC-MS.

$C_{25}H_{28}ClNO_2$ calculated value: 409.9; actually measured value: 410.8

Synthesis of Intermediate I-6

16.758 g (37.2 mmol) of Intermediate I-5, 6.15 g (37.2 mmol) of potassium iodine, and 39.45 g (372 mmol) of sodium hydrophosphite were refluxed in 500 mL of an acetic acid for 3 hours. The reaction product was cooled to room temperature and filtered, and washed several times with water and ethanol, followed by drying to obtain 9.63 g (Yield: 62%) of Intermediate I-6. The formed compound was confirmed by LC-MS.

$C_{25}H_{26}ClN$ calculated value: 375.9; actually measured value: 376.9

Synthesis Example 2

Synthesis of Intermediate II-2

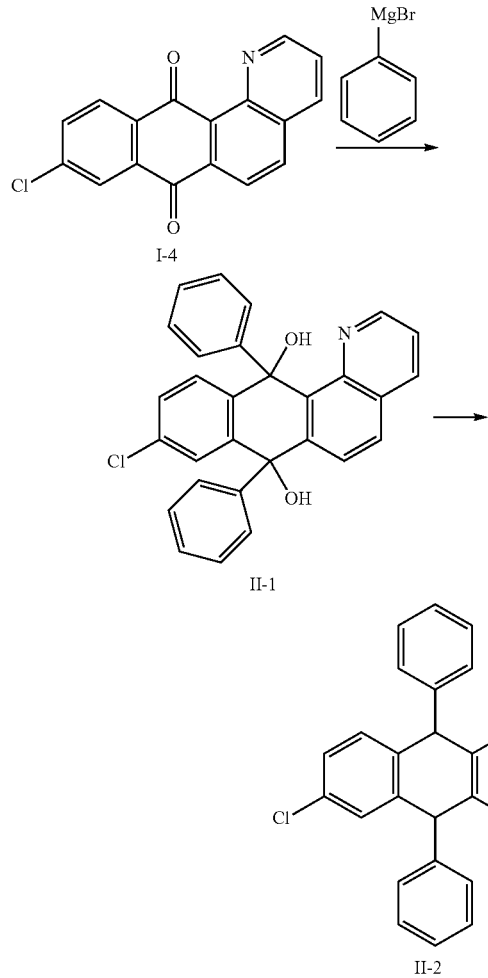

Synthesis of Intermediate II-1

Intermediate II-1 was prepared using Intermediate I-4 and phenylmagnesiumbromide by using the method used to synthesize Intermediate I-5. The formed compound was confirmed by LC-MS.

$C_{29}H_{20}ClNO_2$ calculated value: 449.9; actually measured value: 450.8

Synthesis of Intermediate II-2

Intermediate II-2 was prepared using Intermediate II-1 by using the method used to synthesize Intermediate I-6. The formed compound was confirmed by LC-MS.

$C_{29}H_{20}ClN$ calculated value: 417.9; actually measured value: 418.9

Synthesis Example 3

Synthesis of Intermediate III-2

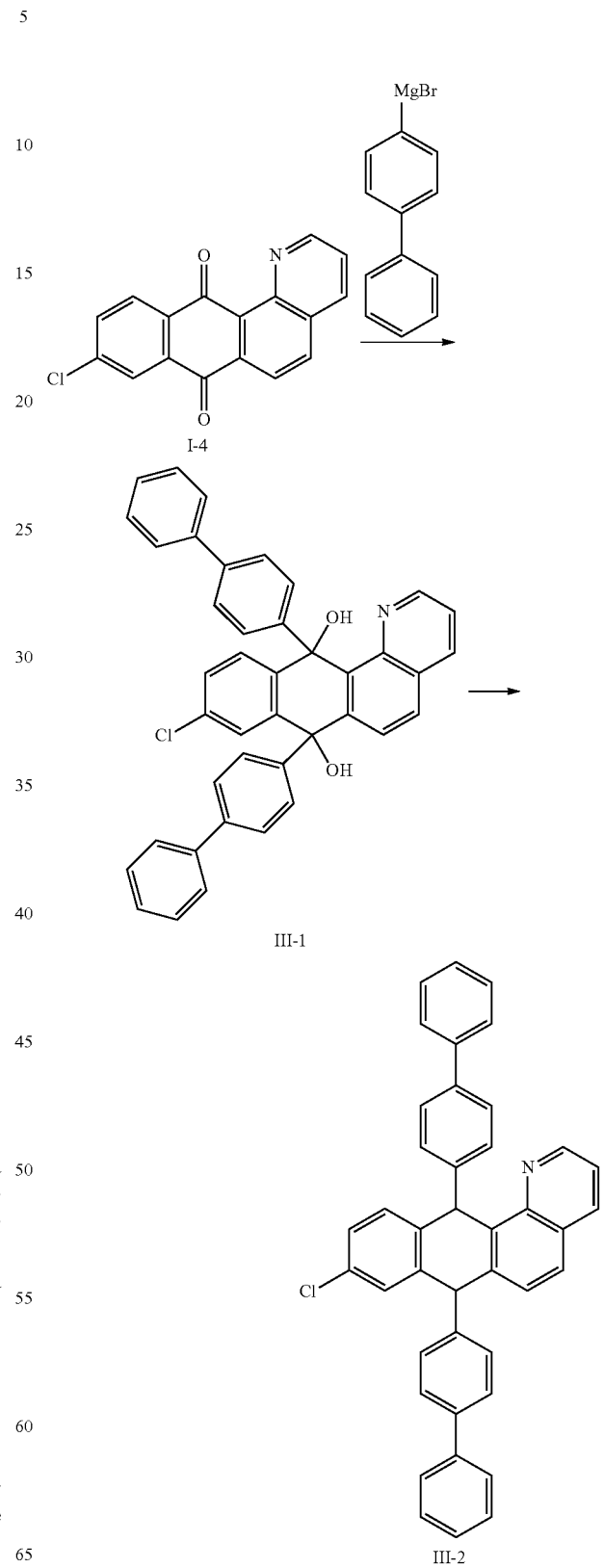

Synthesis of Intermediate III-1

Intermediate III-1 was prepared using Intermediate I-4 and biphenylmagnesiumbromide by using the method used to synthesize Intermediate I-5. The formed compound was confirmed by LC-MS.

$C_{41}H_{28}ClNO_2$ calculated value: 601.1; actually measured value: 602.2

Synthesis of Intermediate III-2

Intermediate III-2 was prepared using Intermediate III-1 by using the method used to synthesize Intermediate I-6. The formed compound was confirmed by LC-MS.

$C_{41}H_{28}ClN$ calculated value: 570.1; actually measured value: 571.1

Synthesis Example 4

Synthesis of Intermediate IV-3

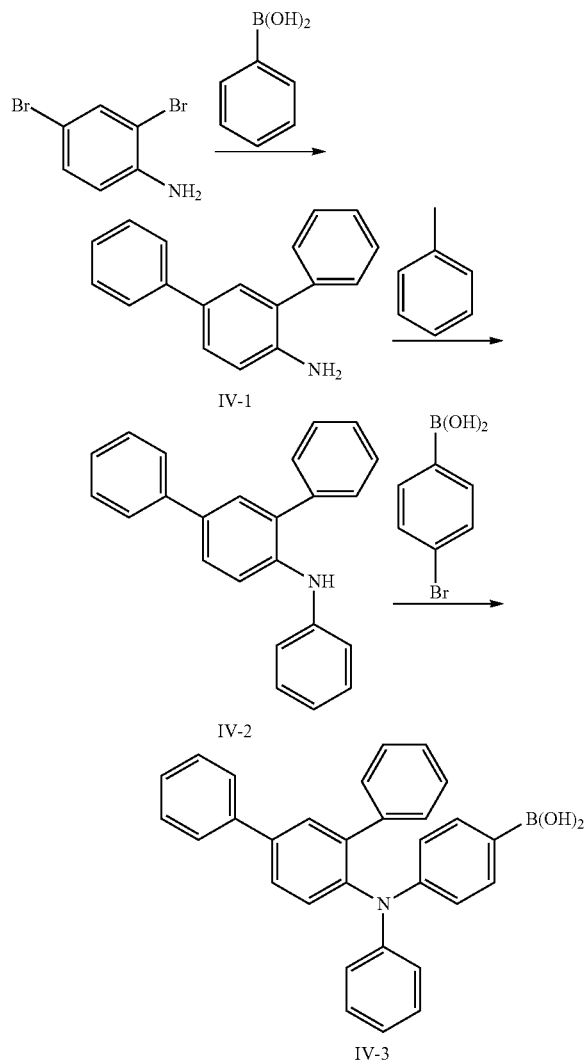

Synthesis of Intermediate IV-1

In a nitrogen atmosphere, 5.018 g (20 mmol) of 2,4-dibromoaniline, 4.877 g (40 mmol) of a phenylboronic acid, 1.15 g (1.0 mmol) of $Pd(PPh_3)_4$, and 8.29 g (60.0 mmol) of $K_2CO_3$ were dissolved in 60 ml of a $THF/H_2O$ (2/1) mixed solution, and then stirred at a temperature of 70° C. for 5 hours. The reaction solution was cooled to room temperature, and 40 mL of water was added thereto and extraction was performed three times thereon with 50 mL of ethylether. A collected organic layer was dried using magnesium sulfate, and the residual obtained by removing the used solvent therefrom by evaporation was separation purified by silica gel column chromatography to obtain Intermediate IV-1 4.464 g (Yield: 91%). The formed compound was confirmed by LC-MS.

$C_{18}H_{15}N$ calculated value: 245.3; actually measured value: 246.3

Synthesis of Intermediate IV-2

In a nitrogen atmosphere, 4.464 g (18.2 mmol) of Intermediate IV-1, 6.12 g (30.0 mmol) of benzene iodide, 0.36 g (0.4 mmol) of $Pd_2(dba)_3$, 0.08 g (0.8 mmol) of $PtBu_3$, and 3.88 g (30.0 mmol) of KOtBu were dissolved in 100 ml of toluene, and then stirred at a temperature of 85° C. for 4 hours. The reaction solution was cooled to room temperature, and then extraction was performed thereon three times with 50 mL of water and 50 mL of diethylether. A collected organic layer was dried using magnesium sulfate, and the residual obtained by removing the used solvent therefrom by evaporation was separation purified by silica gel column chromatography to obtain Intermediate IV-2 4.34 g (Yield: 75%). The formed compound was confirmed by LC-MS.

$C_{24}H_{19}N$ calculated value: 321.4; actually measured value: 322.4

Synthesis of Intermediate IV-3

In a nitrogen atmosphere, 4.34 g (13.5 mmol) of Intermediate IV-2, 4.076 g (20.0 mmol) of 4-bromophenylboronic acid, 0.36 g (0.4 mmol) of $Pd_2(dba)_3$, 0.08 g (0.8 mmol) of $PtBu_3$, and 2.16 g (20.0 mmol) of KO/Bu were dissolved in 100 ml of toluene, and then stirred at a temperature of 85° C. for 4 hours. The reaction solution was cooled to room temperature, and then extraction was performed thereon three times with 50 mL of water and 50 mL of diethylether. A collected organic layer was dried using magnesium sulfate, and the residual obtained by removing the used solvent therefrom by evaporation was separation purified by silica gel column chromatography to obtain 3.572 g (Yield: 60%) of Intermediate IV-3. The formed compound was confirmed by LC-MS.

$C_{30}H_{29}BNO_2$ calculated value: 441.3; actually measured value: 442.3

Synthesis Example 5

Synthesis of Intermediate V-3

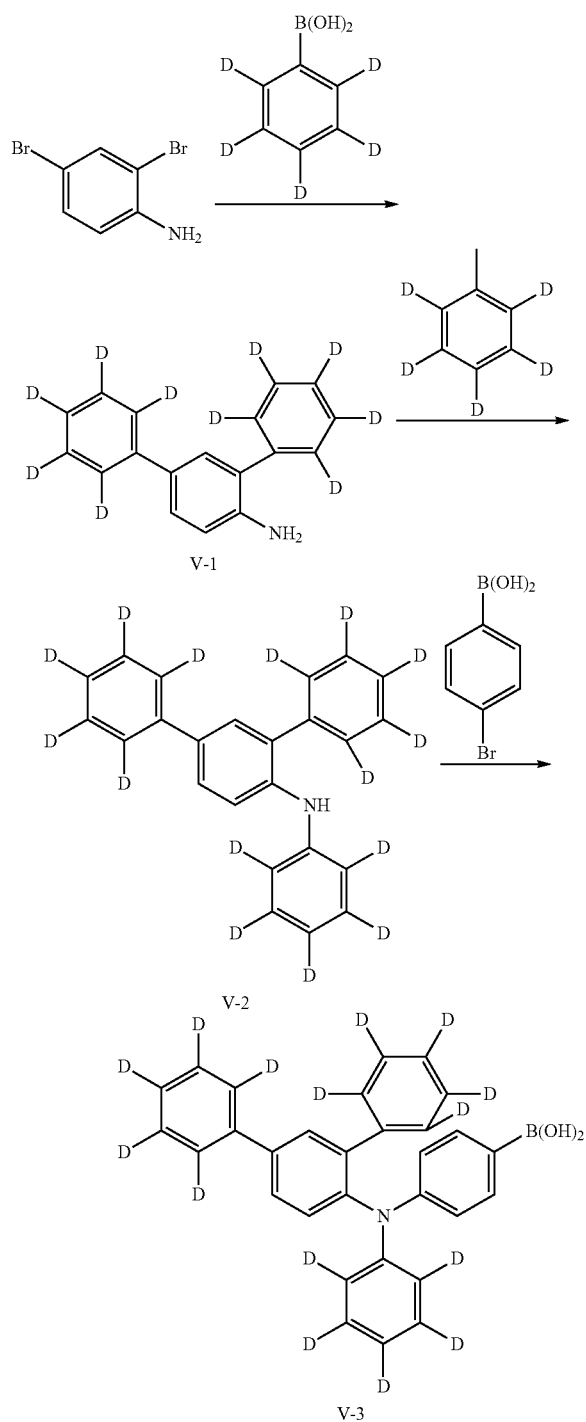

Synthesis of Intermediate V-1

In a nitrogen atmosphere, 5.018 g (20 mmol) of 2,4-dibromoaniline, 4.877 g (40 mmol) of 5D-phenylboronic acid, 1.15 g (1.0 mmol) of Pd(PPh$_3$)$_4$, and 8.29 g (60.0 mmol) of K$_2$CO$_3$ were dissolved in 60 ml of THF/H$_2$O(2/1) mixed solution, and then stirred at a temperature of 70° C. for 5 hours. The reaction solution was cooled to room temperature and then 40 mL of water was added thereto, and extraction was performed thereon three times with 50 mL of ethylether. A collected organic layer was dried using magnesium sulfate, and the residual obtained by removing the used solvent therefrom by evaporation was separation purified by silica gel column chromatography to obtain Intermediate V-1 4.443 g (Yield: 89%). The formed compound was confirmed by LC-MS.

C$_{18}$H$_5$D$_{10}$N calculated value: 255.3; actually measured value: 265.3

Synthesis of Intermediate V-2

In a nitrogen atmosphere, 4.443 g (17.8 mmol) of Intermediate V-1, 6.13 g (30.0 mmol) of 5D-benzene iodide, 0.36 g (0.4 mmol) of Pd$_2$(dba)$_3$, 0.08 g (0.8 mmol) of PtBu$_3$, and 3.88 g (30.0 mmol) of KOtBu were dissolved in 100 ml of toluene, and then stirred at a temperature of 85° C. for 4 hours. The reaction solution was cooled to room temperature, and then extraction was performed thereon three times with 50 mL of water and 50 mL of diethylether. A collected organic layer was dried using magnesium sulfate, and the residual obtained by removing the used solvent therefrom by evaporation was separation purified by silica gel column chromatography to obtain Intermediate V-2 4.192 g (Yield: 70%). The formed compound was confirmed by LC-MS.

C$_{24}$H$_4$D$_{15}$N calculated value: 336.5; actually measured value: 337.5

Synthesis of Intermediate V-3

In a nitrogen atmosphere, 4.192 g (12.4 mmol) of Intermediate V-2, 4.076 g (20.0 mmol) of 4-bromophenylboronic acid, 0.36 g (0.4 mmol) of Pd$_2$(dba)$_3$, 0.08 g (0.8 mmol) of PtBu$_3$, and 2.16 g (20.0 mmol) of KOtBu were dissolved in 100 ml of toluene, and then stirred at a temperature of 85° C. for 4 hours. The reaction solution was cooled to room temperature, and then extraction was performed thereon three times with 50 mL of water and 50 mL of diethylether. A collected organic layer was dried using magnesium sulfate, and the residual obtained by removing the used solvent therefrom by evaporation was separation purified by silica gel column chromatography to obtain Intermediate V-3 3.848 g (Yield: 68%). The formed compound was confirmed by LC-MS.

C$_{30}$H$_9$D$_{15}$BNO$_2$ calculated value: 456.4; actually measured value: 466.4.

Synthesis Example 6

Synthesis of VI-2

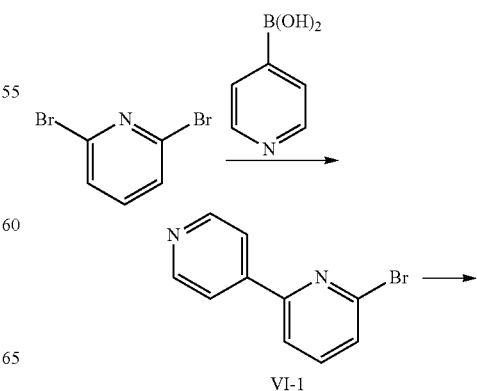

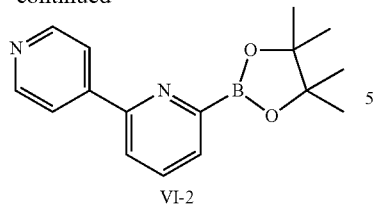

VI-2

In a nitrogen atmosphere, 7.106 g (30.0 mmol) of 2,6-dibromopyridine, 1.843 g (15.0 mmol) of 4-pyridineboronic acid, 1.733 g (1.5 mmol) of Pd(PPh$_3$)$_4$, and 4.146 g (30.0 mmol) of K$_2$CO$_3$ were dissolved in 120 ml of THF/H$_2$O (2/1) mixed solution, and then stirred at a temperature of 70° C. for 5 hours. The reaction solution was cooled to room temperature and then 70 mL of water was added thereto, and extraction was performed thereon three times with 50 mL of ethylether. A collected organic layer was dried using magnesium sulfate, and the residual obtained by removing the used solvent therefrom by evaporation was separation purified by silica gel column chromatography to obtain Intermediate VI-1 1.76 g (Yield: 25%). The formed compound was confirmed by LC-MS.

C$_{10}$H$_7$BrN$_2$ calculated value: 235.0; actually measured value: 235.9

Synthesis of Intermediate VI-2

9.72 g (30.0 mmol) of 4-bromotriphenylamine, 7.62 g (30.0 mmol) of bis(pinacolato)diborone, 1.08 g (1.5 mmol) of [1,1'-bis(diphenylphosphino)ferrocene]dichloropalladium (II)) (PdCl$_2$(dppf)$_2$), and 9 g (90.0 mmol) of KOAc were dissolved in 120 ml of DMSO, and then stirred at a temperature of 80° C. for 6 hours. The reaction solution was cooled to room temperature, and then extraction was performed thereon three times with 100 mL of water and 100 mL of diethylether. A collected organic layer was dried using magnesium sulfate, and the residual obtained by removing the used solvent therefrom by evaporation was separation purified by silica gel column chromatography to obtain intermediate VI-2 7.71 g (Yield: 89%). The formed compound was confirmed by LC-MS.

C$_{16}$H$_{19}$BN$_2$O$_2$ calculated value: 282.1; actually measured value: 283.2

Synthesis Example 7

Synthesis of Intermediate VII-1

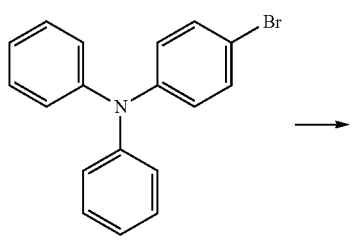

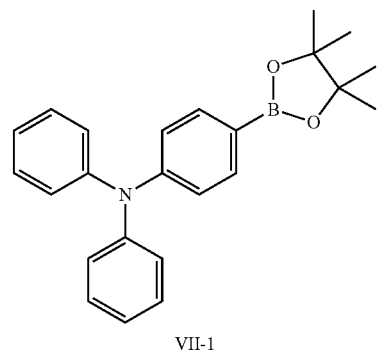

VII-1

9.72 g (30.0 mmol) of 4-bromotriphenylamine, 7.62 g (30.0 mmol) of bis(pinacolato)diborane, 1.08 g (1.5 mmol) of PdCl$_2$(dppf)$_2$), and 9 g (90.0 mmol) of KOAc were dissolved in 120 ml of DMSO, and then stirred at a temperature of 80° C. for 6 hours. The reaction solution was cooled to room temperature, and then extraction was performed thereon three times with 100 mL of water and 100 mL of diethylether. A collected organic layer was dried using magnesium sulfate, and the residual obtained by removing the used solvent therefrom by evaporation was separation purified by silica gel column chromatography to obtain 7.71 g (Yield: 89%) of Intermediate VII-1. The formed compound was confirmed by LC-MS.

C$_{24}$H$_{26}$BNO$_2$ calculated value: 371.2; actually measured value: 372.2

Synthesis Example 8

Synthesis of Intermediate VIII-3

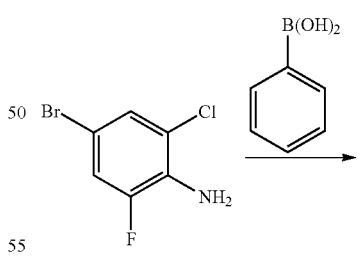

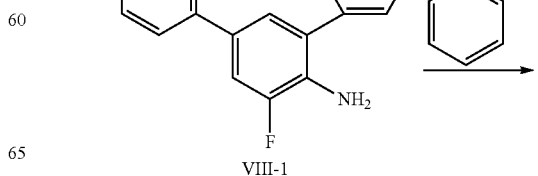

VIII-1

Synthesis of Intermediate VIII-1

In a nitrogen atmosphere, 4.449 g (20 mmol) of 2-chloro-4-bromo-6-floroaniline, 4.877 g (40 mmol) of a phenylboronic acid, 1.15 g (1.0 mmol) of Pd(PPh$_3$)$_4$, and 8.29 g (60.0 mmol) of K$_2$CO$_3$ were dissolved in 60 ml of a THF/H$_2$O (2/1) mixed solution; and then stirred at a temperature of 70° C. for 5 hours. The reaction solution was cooled to room temperature and 40 mL of water was added thereto, and then extraction was performed thereon three times with 50 mL of ethylether. A collected organic layer was dried using in magnesium sulfate, and the residual obtained by removing the used solvent therefrom by evaporation was separation purified by silica gel column chromatography to obtain Intermediate VIII-1 4.465 g (Yield: 81%). The formed compound was confirmed by LC-MS.

C$_{18}$H$_{14}$FN calculated value: 263.1; actually measured value: 264.1

Synthesis of Intermediate VIII-2

In a nitrogen atmosphere, 4.465 g (16.2 mmol) of Intermediate VIII-1, 5.10 g (25.0 mmol) of benzene iodide, 0.36 g (0.4 mmol) of tris(dibenzylideneacetone)dipalladium(0) (Pd$_2$(dba)$_3$), 0.08 g (0.8 mmol) of PtBu$_3$, and 3.88 g (30.0 mmol) of KOtBu were dissolved in 100 ml of toluene, and then stirred at a temperature of 85° C. for 4 hours. The reaction solution was cooled to room temperature room temperature, and then extraction was performed thereon three times with 50 mL of water and 50 mL of diethylether. A collected organic layer was dried using magnesium sulfate, and the residual obtained by removing the used solvent therefrom by evaporation was separation purified by silica gel column chromatography to obtain Intermediate VIII-2 3.906 g (Yield: 72%). The formed compound was confirmed by LC-MS.

C$_{24}$H$_{18}$FN calculated value: 339.40; actually measured value: 340.1

Synthesis of Intermediate VIII-3

In a nitrogen atmosphere, 3.906 g (11.5 mmol) of Intermediate VIII-2, 3.057 g (15.0 mmol) of 4-bromophenylboronic acid, 0.36 g (0.4 mmol) of Pd$_2$(dba)$_3$, 0.08 g (0.8 mmol) of PtBu$_3$, and 2.16 g (20.0 mmol) of KOtBu were dissolved in 100 ml of toluene, and then stirred at a temperature of 85° C. for 4 hours. The reaction solution was cooled to room temperature room temperature, and then extraction was performed thereon three times with 50 mL of water and 50 mL of diethylether. A collected organic layer was dried using magnesium-sulfate, and the residual obtained by removing the used solvent therefrom by evaporation was separation purified by silica gel column chromatography to obtain Intermediate VIII-3 4.12 g (Yield: 78%). The formed compound was confirmed by LC-MS.

C$_{30}$H$_{23}$BFNO$_2$ calculated value: 459.3; actually measured value: 460.2

Synthesis Example 9

Synthesis of Intermediate IX-2

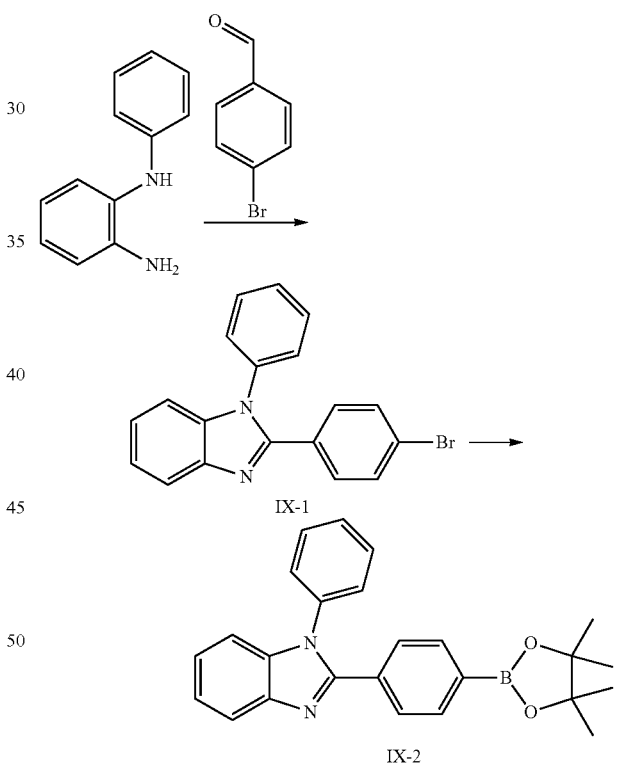

Synthesis of Intermediate IX-1

3.688 g (20.0 mmol) of 4-bromo-benzaldehyde was dispersed in 30 ml of nitrobenzene and 3.684 g (20.0 mmol) of N-phenyl-1,2-phenylenediamine was added thereto, and the mixture was heated for 6 hours at a temperature of 180° C. The reaction solution was cooled to room temperature, and the nitrobenzene was removed therefrom by distillation under reduced pressure. The resultant solution was filtered to obtain a solid, and the solid was washed with ethylether, followed by drying in vacuum conditions, thereby obtaining Intermediate IX-1(4.958 g, 71%). The formed compound was confirmed by LC-MS.

$C_{19}H_{13}BrN_2$ calculated value: 349.3; actually measured value: 350.3

Synthesis of Intermediate IX-2

4.958 g (14.2 mmol) of Intermediate DC-1, 3.812 g (15.0 mmol) of bis(pinacolato)diborane, 0.54 g (0.75 mmol) of $PdCl_2(dppf)_2$, and 4.5 g (45.0 mmol) of KOAc were dissolved in 120 ml of DMSO, and then stirred at a temperature of 80° C. for 6 hours. The reaction solution was cooled to room temperature, and extraction was performed thereon three times with 100 mL of water and 100 mL of diethylether. A collected organic layer was dried using magnesium sulfate, and the residual obtained by removing the used solvent therefrom by evaporation was separation purified by silica gel column chromatography to obtain Intermediate IX-2 7.71 g (Yield: 89%). The formed compound was confirmed by LC-MS.

$C_{25}H_{25}BN_2O_2$ calculated value: 396.3; actually measured value: 397.3

Synthesis Example 10

Synthesis of Compound 25

In a nitrogen atmosphere, 2.903 g (8.0 mmol) of Intermediate I-6, 3.528 g (8.0 mmol) of Intermediate IV-3, 0.05 g (0.04 mmol) of $Pd(PPh_3)_4$, and 2.76 g (20.0 mmol) of $K_2CO_3$ were dissolved in 60 ml of a $THF/H_2O$ (2/1) mixed solution, and then stirred at a temperature of 70° C. for 5 hours. The reaction solution was cooled to room temperature and 40 mL of water was added thereto, and then extraction was performed thereon three times with 30 mL of ethylether. A collected organic layer was dried using magnesium sulfate, and the residual obtained by removing the used solvent therefrom by evaporation was separation purified by silica gel column chromatography to obtain 3.657 g (Yield: 65%) of Compound 25. The formed compound was confirmed by LC/MS and nuclear magnetic resonance (NMR).

$C_{55}H_{48}N_2$ calculated value: 736.9; actually measured value: 737.9

$^1H$ NMR (CDCl$_3$, 400 MHz) δ (ppm) 8.88 (dd, 1H), 8.23 (d, 1H), 8.09 (d, 1H), 8.07 (d, 1H), 7.80-7.66 (m, 8H), 7.60-7.50 (m, 2H), 7.48-7.40 (m, 8H), 7.26-7.18 (m, 3H), 7.14-7.12 (m, 2H), 7.05-7.01 (m, 1H), 6.98-6.96 (m, 2H), 1.53 (s, 9H), 1.51 (s, 9H)

Synthesis Example 11

Synthesis of Compound 27

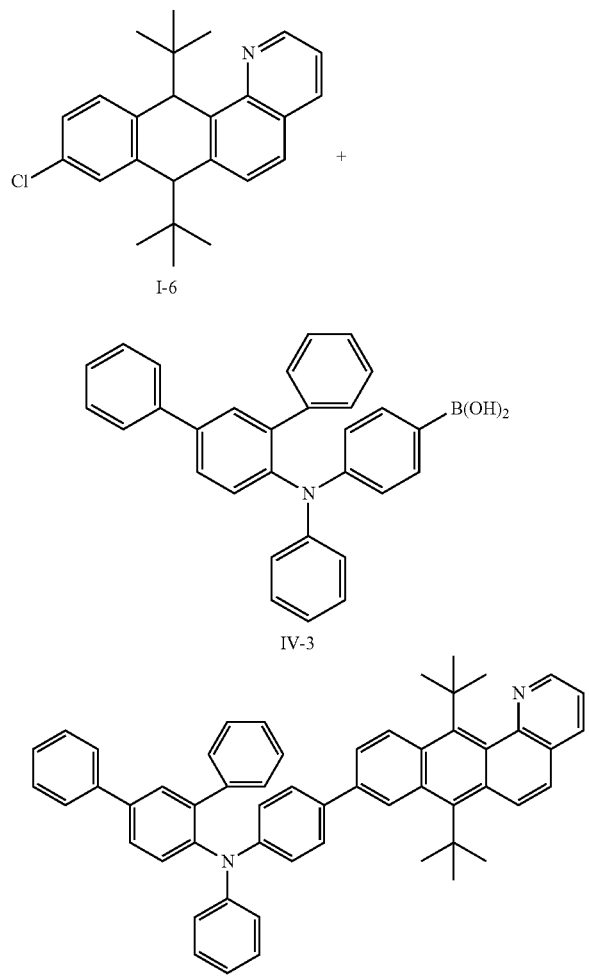

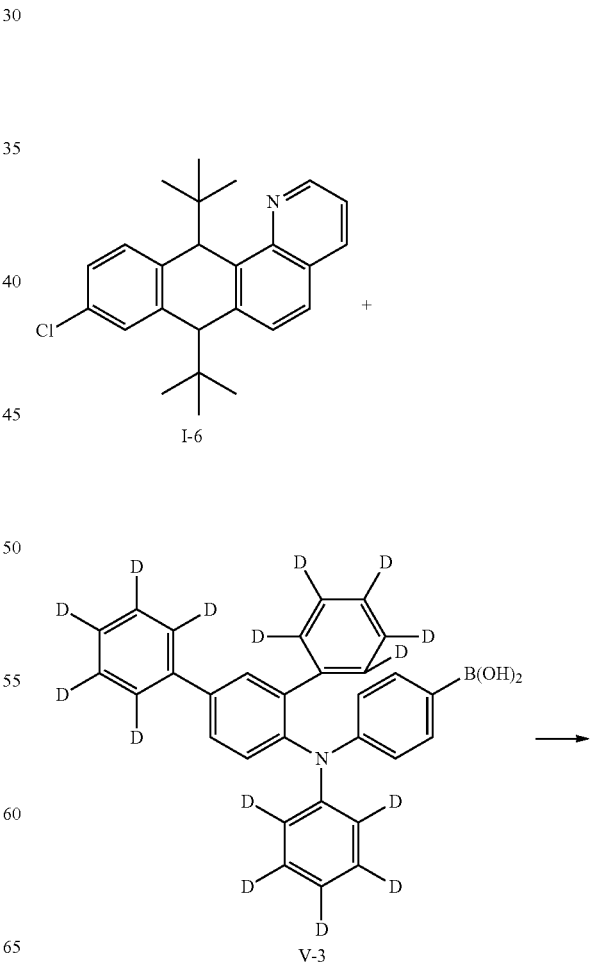

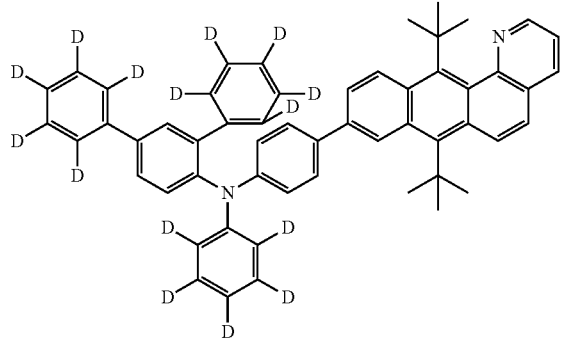

Compound 27 was obtained using Intermediate I-6 and Intermediate V-3 by using the method used to synthesize Compound 25. The formed compound was confirmed by LC/MS and NMR.

$C_{55}H_{33}D_{15}N_2$ calculated value: 752.1; actually measured value: 753.1

$^1$H NMR (CDCl$_3$, 400 MHz) δ (ppm) 8.88 (dd, 1H), 8.23 (d, 1H), 8.06 (d, 1H), 8.05 (d, 1H), 7.79 (d, 1H), 7.75 (q, 2H), 7.53-7.46 (m, 4H), 7.40 (dd, 1H), 7.26 (d 1H), 7.14 (dd, 2H), 1.53 (s, 9H), 1.51 (s, 9H)

Synthesis Example 12

Synthesis of Compound 30

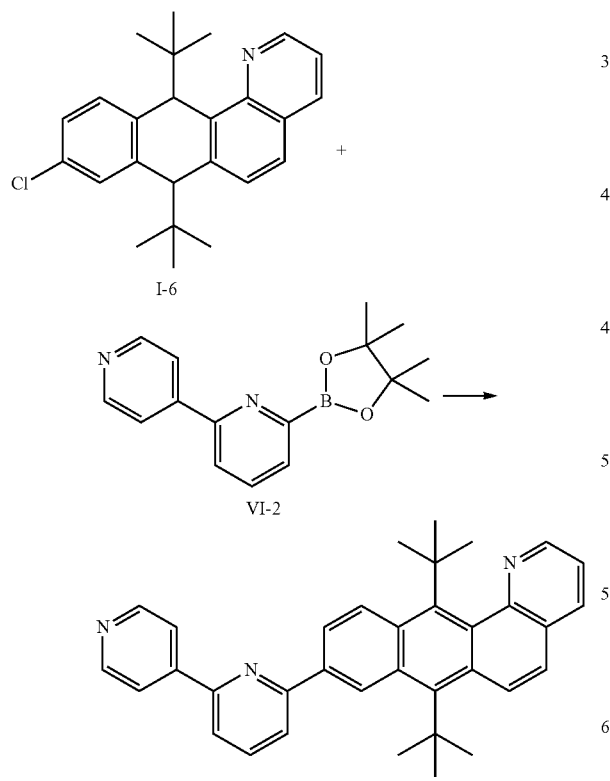

Compound 30 was obtained using Intermediate I-6 and Intermediate VI-2 by using the method used to synthesize Compound 25. The formed compound was confirmed by LC/MS and NMR.

$C_{35}H_{33}N_3$ calculated value: 495.6; actually measured value: 496.6

$^1$H NMR (CDCl$_3$, 400 MHz) δ (ppm) 8.84 (dd, 1H), 8.79 (d, 1H), 8.65 (dd, 2H), 8.24-8.21 (m, 2H), 8.09 (dd, 1H), 8.04 (dd, 2H), 7.87 (t, 1H), 7.80 (d, 1H), 7.74-7.70 (m, 3H), 7.51 (q, 1H), 1.53 (s, 9H), 1.51 (s, 9H)

Synthesis Example 13

Synthesis of Compound 54

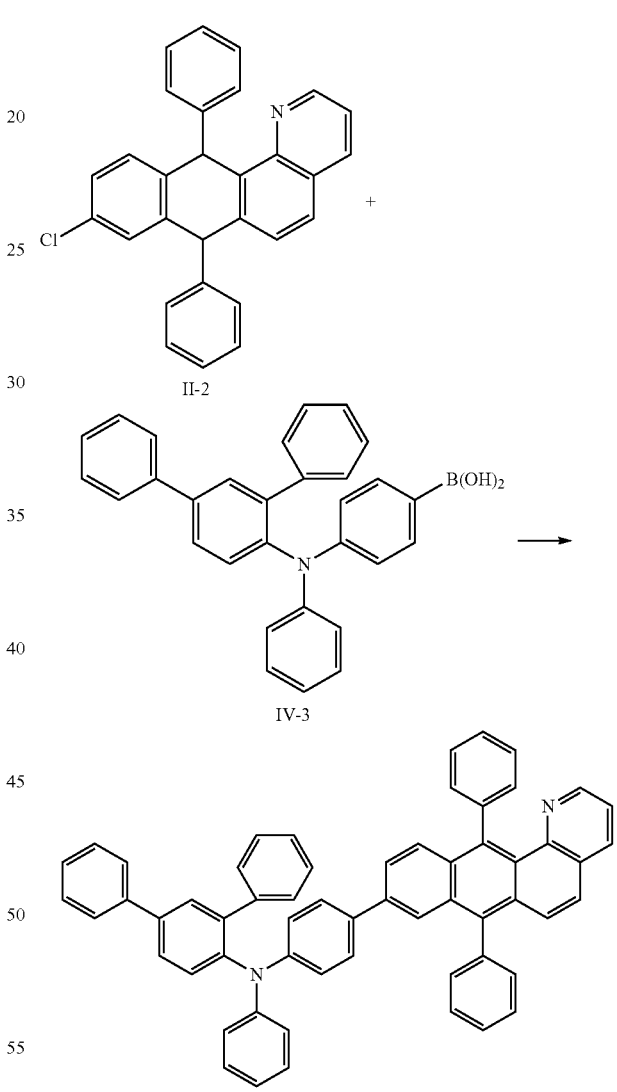

Compound 54 was obtained using Intermediate II-2 and Intermediate IV-3 by using the method used to synthesize Compound 25. The formed compound was confirmed by LC/MS and NMR.

$C_{59}H_{40}N_2$ calculated value: 776.9; actually measured value: 777.9

$^1$H NMR (CDCl$_3$, 400 MHz) δ (ppm) 8.88 (dd, 1H), 8.29 (d, 1H), 8.23 (d, 1H), 8.03 (s, 1H), 7.95 (d, 2H), 7.87 (dd, 2H), 7.85 (dd, 1H), 7.72-7.41 (m, 23H), 7.29-7.19 (m, 3H), 7.14 (d, 2H), 7.09 (t, 1H), 6.98 (m, 2H), 1.53 (s, 9H)

Synthesis Example 14

Synthesis of Compound 63

Synthesis Example 15

Synthesis of Compound 65

7.82 (dd, 1H), 7.72 (dd, 2H), 7.65-7.41 (m, 20H), 7.23 (d, 1H), 7.19 (m, 2H), 7.15 (q, 2H), 7.10 (q, 1H), 6.98 (m, 2H)

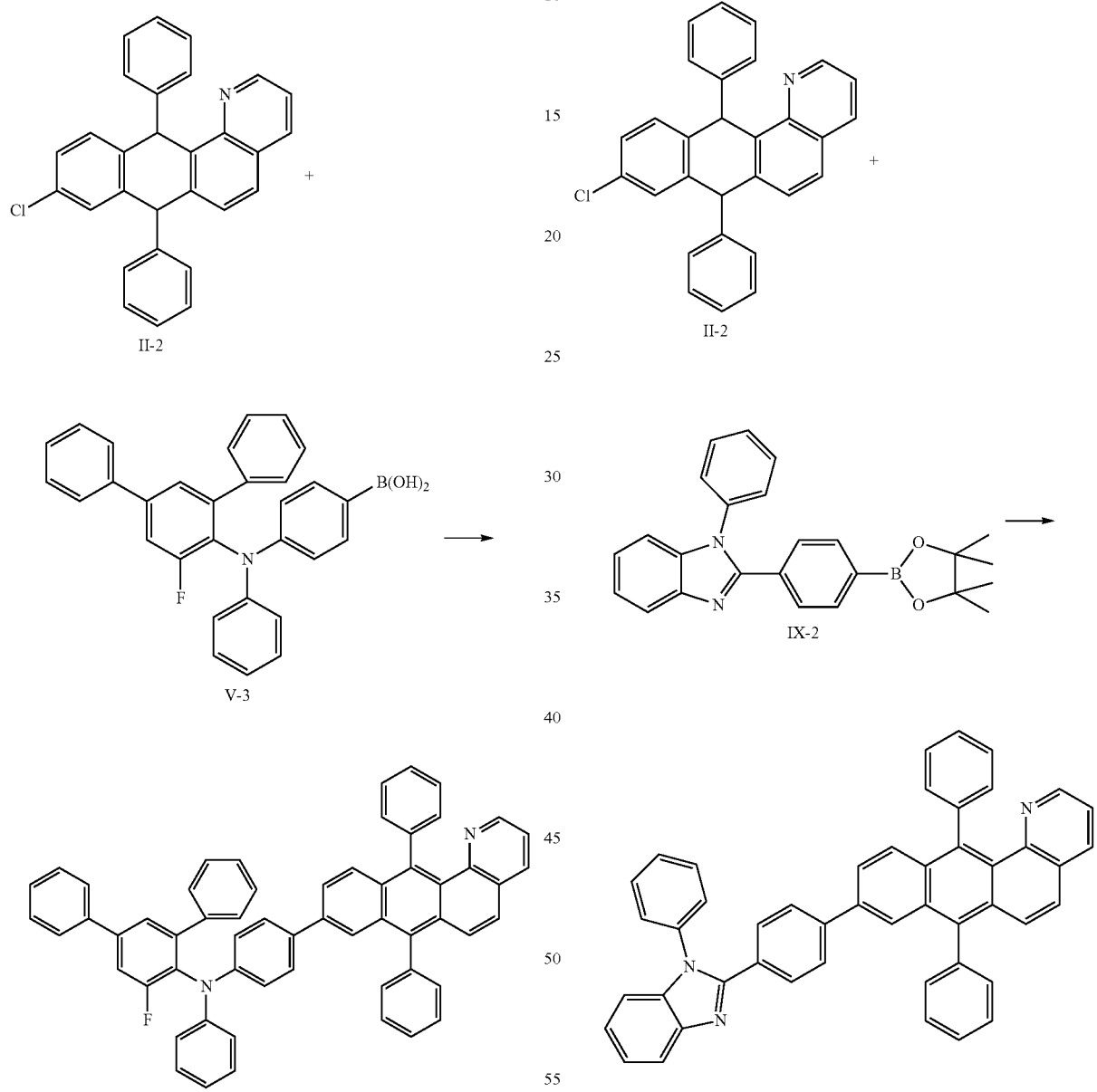

Compound 63 was obtained using Intermediate II-2 and Intermediate V-3 by using the method used to synthesize Compound 25. The formed compound was confirmed by LC/MS and NMR.

$C_{59}H_{39}FN_2$ calculated value: 794.9; actually measured value: 795.6

$^1$H NMR (CDCl$_3$, 400 MHz) δ (ppm) 8.86 (dd, 1H), 8.27 (d, 1H), 8.22 (d, 1H), 8.03 (s, 1H), 7.95 (d, 2H), 7.87 (dd, 2H), Compound 65 was obtained using Intermediate II-2 and Intermediate IX-2 by using the method used to synthesize Compound 25. The formed compound was confirmed by LC/MS and NMR.

$C_{48}H_{31}N_3$ calculated value: 649.7; actually measured value: 650.8

$^1$H NMR (CDCl$_3$, 400 MHz) δ (ppm) 8.88 (dd, 1H), 8.27 (dd, 1H), 8.22 (dd, 1H), 8.14 (d, 1H), 7.95-7.93 (m, 2H), 7.90-7.85 (m, 3H), 7.82-7.72 (m, 5H), 7.67-7.43 (m, 10H), 7.40-7.37 (m, 5H), 7.30 (dd, 1H), 7.19 (m, 1H)

Synthesis Example 16

Synthesis of Compound 75

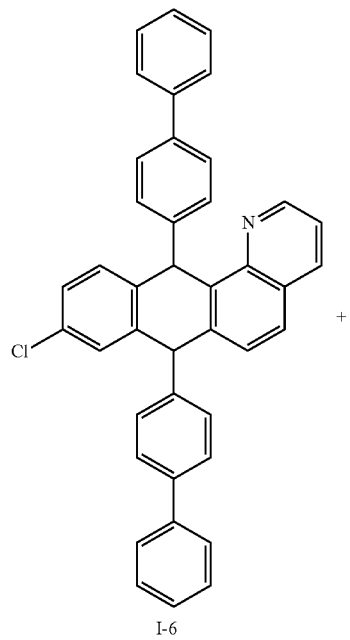

I-6

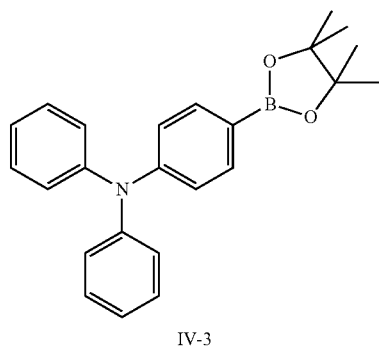

IV-3

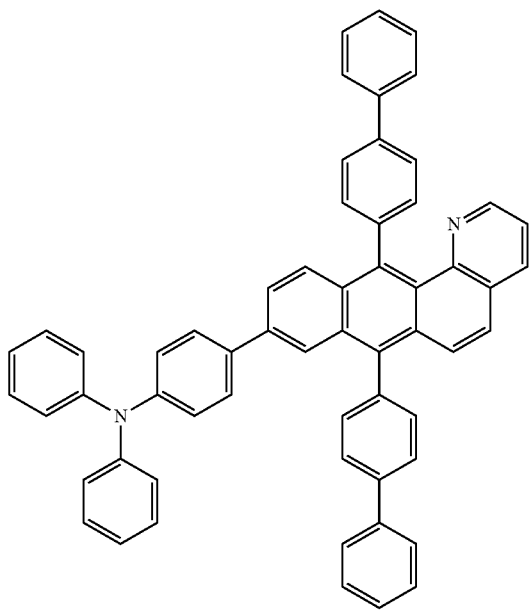

Compound 75 was obtained using Intermediate I-6 and Intermediate 1V-3 by using the method used to synthesize Compound 25. The formed compound was confirmed by LC/MS and NMR.

$C_{59}H_{40}N_2$ calculated value: 776.9; actually measured value: 777.6

$^1$H NMR (CDCl$_3$, 400 MHz) δ (ppm) 8.88 (dd, 1H), 8.29 (d, 1H), 8.23 (d, 1H), 8.06 (s, 1H), 7.94 (d, 2H), 7.85 (s, 4H), 7.82 (d, 1H), 7.72 (d, 2H), 7.63-7.58 (m, GH), 7.55-7.48 (m, 7H), 7.44-7.37 (m 2H), 7.28 (t, 4H), 7.15 (d, 2H), 7.11 (t, 2H), 7.05 (d, 4H)

Example 1

As an anode, 15 Ω/cm$^2$ (1200 Å) ITO glass substrate manufactured by Corning Co., Ltd was cut to a size of 50 mm×50 mm×0.7 mm and sonicated with isopropyl alcohol and pure water each for 5 minutes, and then ultraviolet rays were irradiated thereto for 30 minutes, followed by exposure to ozone. 2-TNATA was vacuum deposited on the ITO glass substrate to form a HIL having a thickness of 600 Å, and 4,4'-bis[N-(1-naphthyl)-N-phenyl amino]biphenyl (NPB) was vacuum deposited on the HIL to form a HTL having a thickness of 300 Å.

ADN as a blue fluorescent host and Compound 25 as a blue fluorescent dopant were co-deposited on the HTL at a weight ratio of 98:2 to form an EML having a thickness of 300 Å.

Subsequently, Alq$_3$ was vacuum deposited on the EML to form an ETL having a thickness of 10 Å. LiF was deposited on the ETL to form an ETL having a thickness of 10 Å and then, Al was vacuum deposited thereon to form a cathode having a thickness of 3000 Å, thereby completing the manufacture of an organic light-emitting diode.

Example 2

An organic light-emitting diode was manufactured in the same manner as in Example 1, except that in forming the EML, Compound 27 was used as the blue fluorescent dopant instead of Compound 25.

Example 3

An organic light-emitting diode was manufactured in the same manner as in Example 1, except that in forming the EML, Compound 54 was used as the blue fluorescent dopant instead of Compound 25.

Example 4

An organic light-emitting diode was manufactured in the same manner as in Example 1, except that in forming the EML, Compound 63 was used as the blue fluorescent dopant instead of Compound 25.

Example 5

An organic light-emitting diode was manufactured in the same manner as in Example 1, except that in forming the EML, Compound 75 was used as the blue fluorescent dopant instead of Compound 25.

Example 6

An organic light-emitting diode was manufactured in the same manner as in Example 3, except that in forming the ETL, Compound 30 was used instead of Alq$_3$.

Example 7

An organic light-emitting diode was manufactured in the same manner as in Example 1, except that in forming the ETL, Compound 65 was used instead of Alq$_3$.

Comparative Example 1

An organic light-emitting diode was manufactured in the same manner as in Example 1, except that in forming the EML, DPAVBi was used as the blue fluorescent dopant instead of Compound 25.

Evaluation Example

The driving voltage, current density, brightness, efficiency, emission color, and half lifetime of each of the organic light-emitting diodes manufactured according to Examples 1 to 7 and Comparative Example 1 were evaluated using PR650 Spectroscan Source Measurement Unit (a product of Photo-Research Co., Ltd); results thereof are shown in Table 1 below.

TABLE 1

|  | Emission layer host | Emission layer dopant | Electron transport layer | Driving voltage (V) | Current density (mA/cm$^2$) | Brightness (cd/m$^2$) | Efficiency (cd/A) | Emission color | Half lifetime (hr)† |
|---|---|---|---|---|---|---|---|---|---|
| Example 1 | ADN | Compound 25 | Alq3 | 6.04 | 50 | 3,021 | 6.04 | blue | 227 |
| Example 2 | ADN | Compound 27 | Alq3 | 6.15 | 50 | 3,095 | 6.19 | blue | 243 |
| Example 3 | ADN | Compound 54 | Alq3 | 6.23 | 50 | 3,230 | 6.46 | blue | 284 |
| Example 4 | ADN | Compound 63 | Alq3 | 6.14 | 50 | 3,620 | 7.24 | blue | 276 |
| Example 5 | ADN | Compound 75 | Alq3 | 6.33 | 50 | 3,427 | 6.85 | blue | 285 |
| Example 6 | ADN | Compound 54 | Compound 30 | 5.25 | 50 | 3,415 | 6.83 | blue | 230 |
| Example 7 | ADN | Compound 54 | Compound 65 | 5.74 | 50 | 3,270 | 6.54 | blue | 361 |
| Comparative Example 1 | ADN | DPAVBi | Alq3 | 7.35 | 50 | 2,065 | 4.13 | blue | 145 |

†Reference current density of half lifetime: 100 mA/cm$^2$

From Table 1, it was confirmed that the organic light-emitting diodes manufactured according to Examples 1 to 7 have better driving voltage, brightness, efficiency, and lifetime characteristics than the organic light-emitting diode manufactured according to Comparative Example 1.

An organic light-emitting diode including the heterocyclic compound represented by Formula 1 shows excellent performance, for example, a low driving voltage, high brightness, high efficiency, and a long lifetime, and thus is provided to a high quality flat display device.

While the present invention has been particularly shown, and described with reference to exemplary embodiments thereof, it will be understood by those of ordinary skill in the art that various changes in form, and details may be made therein without departing from the spirit, and scope of the present invention as defined by the following claims.

What is claimed is:

1. A heterocyclic compound represented by Formula 1 below:

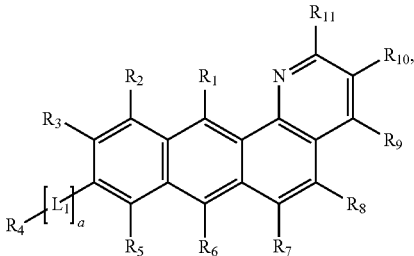

<Formula 1> wherein $R_1$ to $R_{11}$ are each independently a hydrogen atom, a deuterium atom, a halogen atom, a hydroxyl group, a cyano group, a nitro group, a carboxyl group, a substituted or unsubstituted $C_1$-$C_{30}$ alkyl group, a substituted or unsubstituted $C_2$-$C_{30}$ alkenyl group, a substituted or unsubstituted $C_2$-$C_{30}$ alkynyl group, a substituted or unsubstituted $C_1$-$C_{30}$ alkoxy group, a substituted or unsubstituted $C_3$-$C_{30}$ cycloalkyl group, a substituted or unsubstituted $C_3$-$C_{30}$ cycloalkenyl group, a substituted or unsubstituted $C_6$-$C_{30}$ aryl group, a substituted or unsubstituted $C_2$-$C_{30}$ heteroaryl group, a substituted or unsubstituted $C_6$-$C_{30}$ aryloxy group, a substituted or unsubstituted $C_6$-$C_{30}$ arylthio group, or a group represented by $N(Q_1)(Q_2)$ where $Q_1$ and $Q_2$ are each independently a hydrogen atom, a deuterium atom, a substituted or unsubstituted methyl group, a substituted or unsubstituted ethyl group, a substituted or unsubstituted propyl group, a substituted or unsubstituted butyl group, a substituted or unsubstituted pentyl group, a substituted or unsubstituted phenyl group, a substituted or unsubstituted pyridinyl group, a substituted or unsubstituted naphthyl group, a substituted or unsubstituted anthryl group, a substituted or unsubstituted fluorenyl group, a substituted or unsubstituted carbazolyl group, or a substituted or unsubstituted pyrimidinyl group, and $L_1$ is a substituted or unsubstituted $C_6$-$C_{30}$ arylene group, or a substituted or unsubstituted $C_3$-$C_{30}$ heteroarylene group, and a is an integer of 1 or 2, wherein if a is 2, two $L_1$ are identical to or different from each other.

2. The heterocyclic compound of claim 1, wherein $R_1$ to $R_{11}$ are each independently a hydrogen atom, a deuterium atom, a halogen atom, a hydroxyl group, a cyano group, a nitro group, a carboxyl group, a substituted or unsubstituted methyl group, a substituted or unsubstituted ethyl group, a substituted or unsubstituted propyl group, a substituted or unsubstituted butyl group, a substituted or unsubstituted pentyl group, a substituted or unsubstituted phenyl group, a substituted or unsubstituted biphenyl group, a substituted or unsubstituted terphenyl group, a substituted or unsubstituted phenoxy group, a substituted or unsubstituted fluorenyl group, a substituted or unsubstituted carbazolyl group, a substituted or unsubstituted naphthyl group, a substituted or unsubstituted phenanthrenyl group, a substituted or unsubstituted pyridinyl group, a substituted or unsubstituted diazinyl group, a substituted or unsubstituted triazinyl group, a substituted or unsubstituted quinolinyl group, a substituted or unsubstituted benzimidazolyl group, a substituted or unsubstituted benzoxazolyl group, a substituted or unsubstituted pentalenyl group, a substituted or unsubstituted indenyl group, a substituted or unsubstituted azulenyl group, a substituted or unsubstituted heptalenyl group, a substituted or unsubstituted indacenyl group, a substituted or unsubstituted acenaphthyl group, a substituted or unsubstituted spiro-fluorenyl group, a substituted or unsubstituted phenalenyl group, a substituted or unsubstituted phenanthridinyl group, a substituted or unsubstituted phenanthrolinyl group, a substituted or unsubstituted anthryl group, a substituted or unsubstituted fluoranthenyl group, a substituted or unsubstituted triphenylenyl group, a substituted or unsubstituted pyrenyl group, a substituted or unsubstituted chricenyl group, a substituted or unsubstituted naphthacenyl group, a substituted or unsubstituted picenyl group, a substituted or unsubstituted perylenyl group, a substituted or unsubstituted pentaphenyl group, a substituted or unsubstituted hexacenyl group, a substituted or unsubstituted pyrrolyl group, a substituted or unsubstituted imidazolyl group, a substituted or unsubstituted pyrazolyl group, a substituted or unsubstituted imidazopyrimidinyl group, a substituted or unsubstituted pyridazinyl group, a substituted or unsubstituted pyrimidinyl group, a substituted or unsubstituted imidazopyrimidinyl group, a substituted or unsubstituted pyridazinyl group, a substituted or unsubstituted indolyl group, a substituted or unsubstituted isoindolyl group, a substituted or unsubstituted pyrido indolyl group, a substituted or unsubstituted indazolyl group, a substituted or unsubstituted purinyl group, a substituted or unsubstituted benzoquinolinyl group, a substituted or unsubstituted phthalazinyl group, a substituted or unsubstituted naphthyridinyl group, a substituted or unsubstituted quinoxalinyl group, a substituted or unsubstituted quinazolinyl group, a substituted or unsubstituted phenazinyl group, a substituted or unsubstituted furanyl group, a substituted or unsubstituted benzofuranyl group, a substituted or unsubstituted dibenzofuranyl group, a substituted or unsubstituted thiophenyl group, a substituted or unsubstituted benzothiophenyl group, a substituted or unsubstituted dibenzothiophenyl group, a substituted or unsubstituted thiazolyl group, a substituted or unsubstituted isothiazolyl group, a substituted or unsubstituted benzothiazolyl group, a substituted or unsubstituted oxazolyl group, a substituted or unsubstituted isooxazolyl group, a substituted or unsubstituted oxadiazolyl group, a substituted or unsubstituted triazolyl group, a substituted or unsubstituted tetrazolyl group, or a group represented by $N(Q_1)(Q_2)$, where $Q_1$ and $Q_2$ are each independently a hydrogen atom, a deuterium atom, a substituted or unsubstituted methyl group, a substituted or unsubstituted ethyl group, a substituted or unsubstituted propyl group, a substituted or unsubstituted butyl group, a substituted or unsubstituted pentyl group, a substituted or unsubstituted phenyl group, a substituted or unsubstituted pyridinyl group, a substituted or unsubstituted naphthyl group, a substituted or unsubstituted anthryl group, a substituted or unsubstituted fluorenyl group, a substituted or unsubstituted carbazolyl group, or a substituted or unsubstituted pyrimidinyl group.

3. The heterocyclic compound of claim 1, wherein $R_1$ to $R_{11}$ are each independently a hydrogen atom, a deuterium atom, halogen atom, a substituted or unsubstituted methyl group, a substituted or unsubstituted ethyl group, a substituted or unsubstituted propyl group, a substituted or unsubstituted butyl group, or one of the groups represented by Formulae 2A to 2P below:

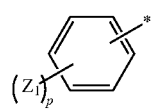
<Formula 2A>

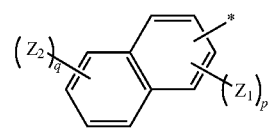
<Formula 2B>

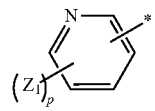
<Formula 2C>

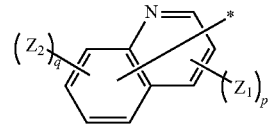
<Formula 2D>

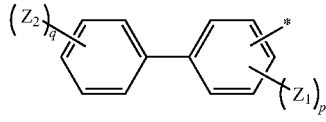
<Formula 2E>

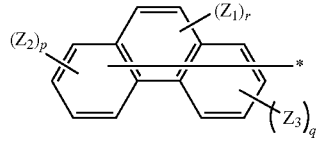
<Formula 2F>

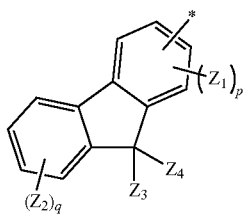
<Formula 2G>

-continued

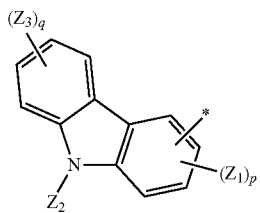
<Formula 2H>

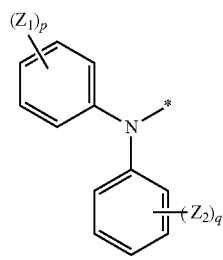
<Formula 2I>

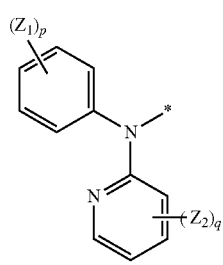
<Formula 2J>

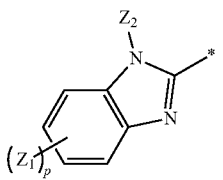
<Formula 2K>

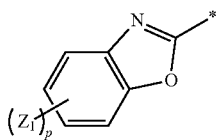
<Formula 2L>

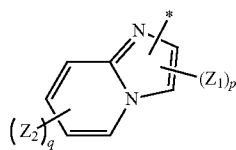
<Formula 2M>

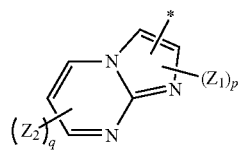
<Formula 2N>

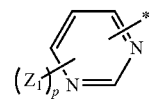
<Formula 2O>

-continued

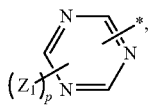
<Formula 2P> wherein $Z_1$, $Z_2$, $Z_3$, and $Z_4$ are each independently a hydrogen atom, a deuterium atom, a halogen atom, a hydroxyl group, a cyano group, a substituted or unsubstituted methyl group, a substituted or unsubstituted ethyl group, a substituted or unsubstituted propyl group, a substituted or unsubstituted butyl group, a substituted or unsubstituted methoxy group, a substituted or unsubstituted ethoxy group, a substituted or unsubstituted phenyl group, a substituted or unsubstituted naphthyl group, a substituted or unsubstituted anthryl group, and a substituted or unsubstituted quinolinyl group, or a substituted or unsubstituted pyridinyl group, a plurality of each of $Z_1$, $Z_2$, $Z_3$, and $Z_4$ are identical to or different from each other, p and q each are an integer of 1 to 5, r is 1 or 2, and * indicates a binding site.

4. The heterocyclic compound of claim 1, wherein $R_1$ to $R_{11}$ are each independently a hydrogen atom, a deuterium atom, halogen atom, a substituted or unsubstituted methyl group, a substituted or unsubstituted ethyl group, a substituted or unsubstituted propyl group, a substituted or unsubstituted tert-butyl group, or a group represented by Formulae 3A to 3R below:

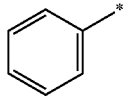
<Formula 3A>

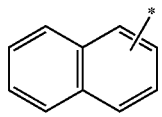
<Formula 3B>

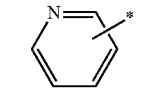
<Formula 3C>

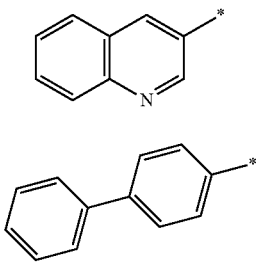
<Formula 3D>

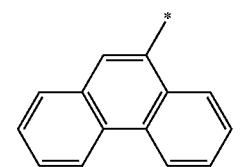
<Formula 3E>

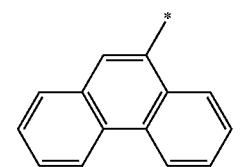
<Formula 3F>

<Formula 3G>
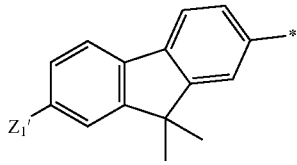

<Formula 3H>
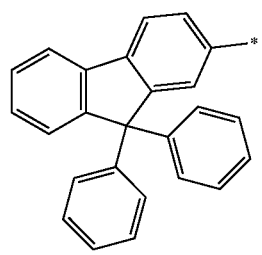

<Formula 3I>
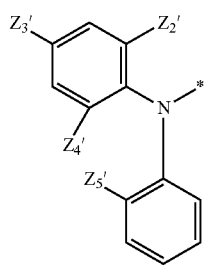

<Formula 3J>
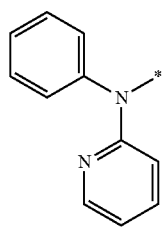

<Formula 3K>
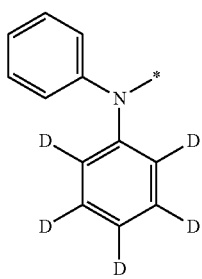

<Formula 3L>
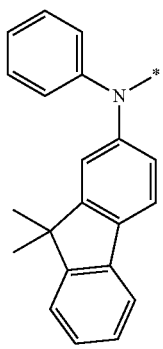

<Formula 3M>
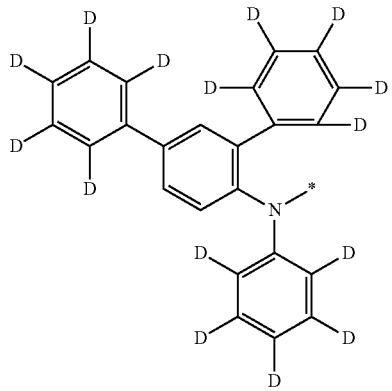

<Formula 3N>

<Formula 3O>
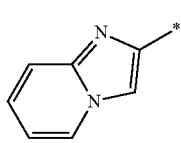

<Formula 3P>
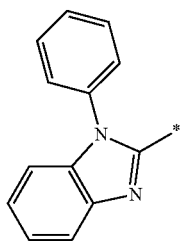

<Formula 3Q>
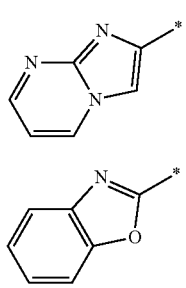

<Formula 3R>
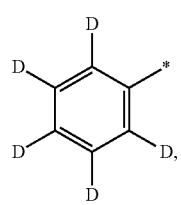

wherein $Z_1$ is a hydrogen atom or a phenyl group, $Z_{2'}$, $Z_{3'}$, $Z_{4'}$, and $Z_{5'}$ are each independently a hydrogen atom, a deuterium atom, a fluoro group, a methyl group, or a phenyl group, a plurality of each of $Z_{2'}$, $Z_{3'}$, $Z_{4'}$, and $Z_{5'}$ are identical to or different from each other, and * indicates a binding site.

5. The heterocyclic compound of claim 1, wherein $L_1$ is a substituted or unsubstituted phenylene group, a substituted or unsubstituted naphthylene group, a substituted or unsubstituted fluorenylene group, a substituted or unsubstituted carbazolylene group, a substituted or unsubstituted pyridinylene group, a substituted or unsubstituted pyrimidinylene group, a substituted or unsubstituted triazinylene group, a substituted or unsubstituted anthrylene group, a substituted or unsubstituted phenanthrenylene group, a substituted or unsubstituted pyrenylene group, a substituted or unsubstituted chrycenylene group, a substituted or unsubstituted perilenylene group, a substituted or unsubstituted spiro-fluorenyl group, or a substituted or unsubstituted oxadiazolylene group.

6. The heterocyclic compound of claim 1, wherein $L_1$ comprises one of the groups represented by Formulae 4A to 4H below:

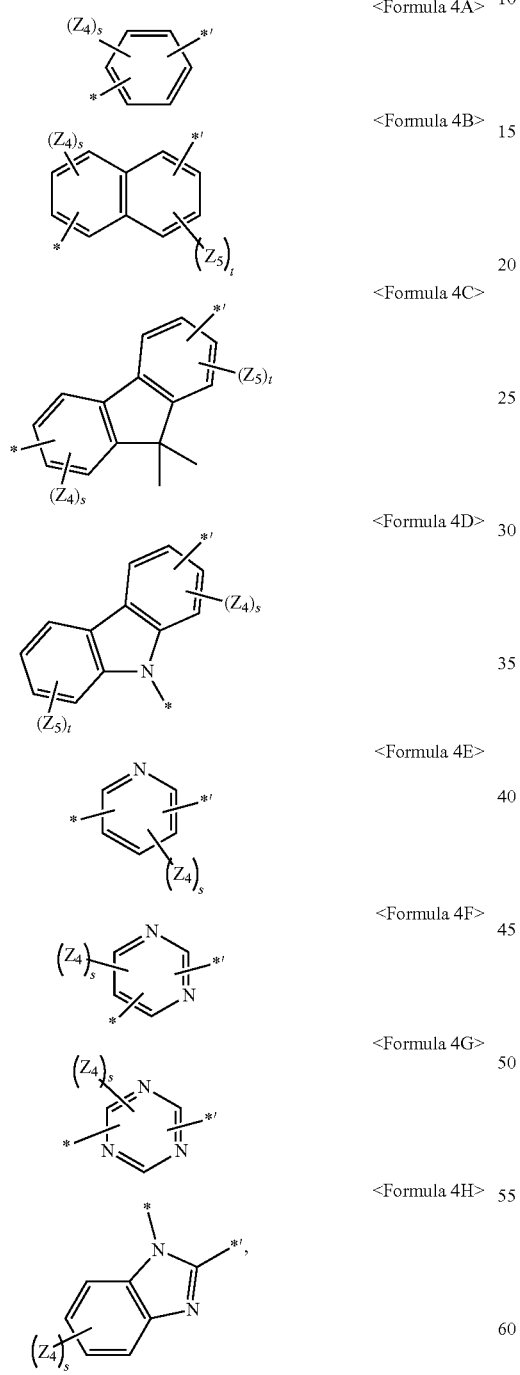

wherein
$Z_4$ and $Z_5$ are each independently a hydrogen atom, a deuterium atom, halogen atom, a substituted or unsubstituted methyl group, a substituted or unsubstituted ethyl group, a substituted or unsubstituted propyl group, a substituted or unsubstituted butyl group, or a substituted or unsubstituted phenyl group, a plurality of each of $Z_4$ and $Z_5$ are identical to or different from each other, and s and t are an integer of 1 to 4, *' indicates a binding site with the anthracene back bone, and * indicates a binding site with $R_3$.

7. The heterocyclic compound of claim 1, wherein $L_1$ comprises one of the groups represented by Formulae 5A to 5I:

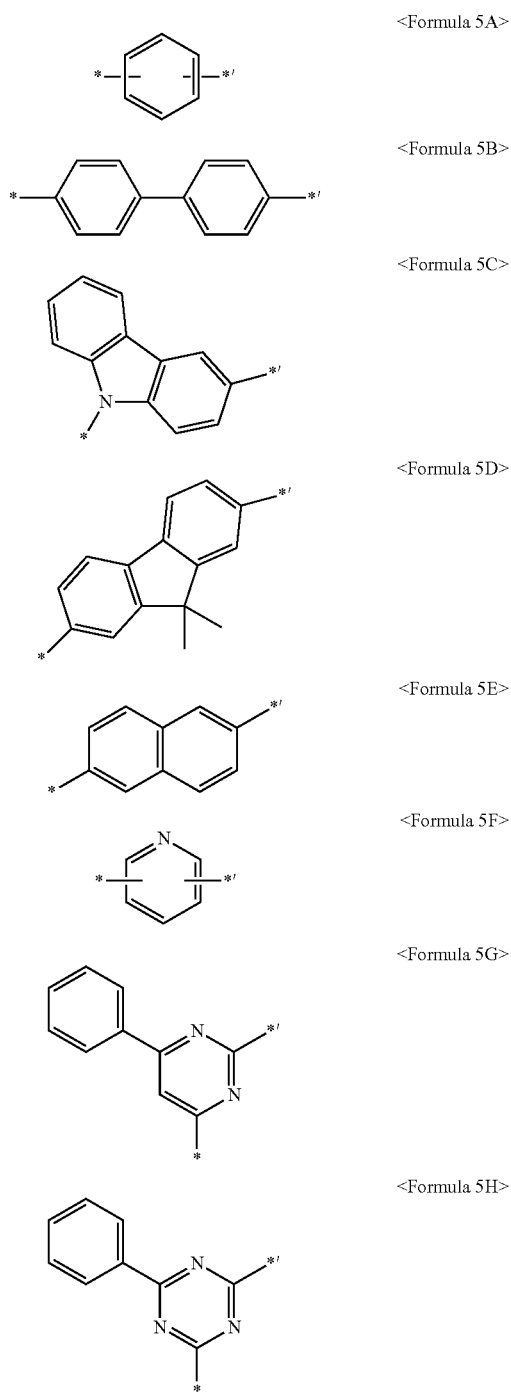

<Formula 5I>

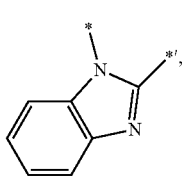

wherein *' indicates a binding site with the anthracene backbone, and * indicates a binding site with $R_3$.

8. The heterocyclic compound of claim 1, wherein the heterocyclic compound is represented by Formula 1a below:

<Formula 1a>

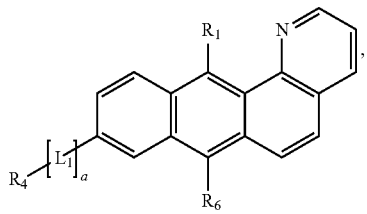

wherein $R_1$, $R_4$, and $R_6$ are each independently a hydrogen atom, a deuterium atom, a halogen atom, a hydroxyl group, a cyano group, a nitro group, a carboxyl group, a substituted or unsubstituted methyl group, a substituted or unsubstituted ethyl group, a substituted or unsubstituted propyl group, a substituted or unsubstituted butyl group, a substituted or unsubstituted pentyl group, a substituted or unsubstituted phenyl group, a substituted or unsubstituted biphenyl group, a substituted or unsubstituted fluorenyl group, a substituted or unsubstituted carbazolyl group, a substituted or unsubstituted naphthyl group, a substituted or unsubstituted phenanthrenyl group, a substituted or unsubstituted pyridinyl group, a substituted or unsubstituted diazinyl group, a substituted or unsubstituted triazinyl group, a substituted or unsubstituted quinolinyl group, a substituted or unsubstituted benzimidazolyl group, a substituted or unsubstituted benzoxazolyl group, a substituted or unsubstituted imidazopyrimidinyl group, a substituted or unsubstituted pyrimidinyl group, a substituted or unsubstituted imidazopyrimidinyl group, a substituted or unsubstituted indolyl group, a substituted or unsubstituted pyrido indolyl group, a substituted or unsubstituted furanyl group, a substituted or unsubstituted benzofuranyl group, a substituted or unsubstituted dibenzofuranyl group, a substituted or unsubstituted thiophenyl group, a substituted or unsubstituted benzothiophenyl group, a substituted or unsubstituted dibenzothiophenyl group, a substituted or unsubstituted oxazolyl group, a substituted or unsubstituted oxadiazolyl group, or a group represented by $N(Q_1)(Q_2)$ where $Q_1$ and $Q_2$ are each independently a hydrogen atom, a deuterium atom, a substituted or unsubstituted methyl group, a substituted or unsubstituted ethyl group, a substituted or unsubstituted propyl group, a substituted or unsubstituted butyl group, a substituted or unsubstituted phenyl group, a substituted or unsubstituted pyridinyl group, a substituted or unsubstituted naphthyl group, a substituted or unsubstituted fluorenyl group, or a substituted or unsubstituted carbazolyl group, $L_1$ is a substituted or unsubstituted phenylene group, a substituted or unsubstituted naphthylene group, a substituted or unsubstituted fluorenylene group, a substituted or unsubstituted carbazolylene group, a substituted or unsubstituted pyridinylene group, a substituted or unsubstituted pyrimidinylene group, a substituted or unsubstituted triazinylene group, a substituted or unsubstituted anthrylene group, a substituted or unsubstituted phenanthrenylene group, a substituted or unsubstituted pyrenylene group, a substituted or unsubstituted chrycenylene group, a substituted or unsubstituted perilenylene group, a substituted or unsubstituted spiro-fluorenyl group, or a substituted or unsubstituted oxadiazolylene group, and a is an integer of 1 or 2, and if a is 2, the two $L_1$ are identical to or different from each other.

9. The heterocyclic compound of claim 8, wherein $R_1$, $R_4$, and $R_6$ are each independently a hydrogen atom, a deuterium atom, halogen atom, a substituted or unsubstituted methyl group, a substituted or unsubstituted ethyl group, a substituted or unsubstituted propyl group, a substituted or unsubstituted butyl group, or one of the groups represented by Formulae 2A to 2P below:

<Formula 2A>

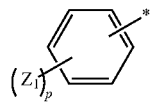

<Formula 2B>

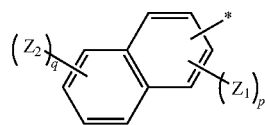

<Formula 2C>

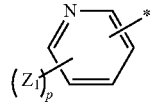

<Formula 2D>

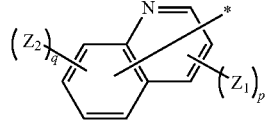

<Formula 2E>

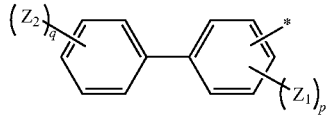

<Formula 2F>

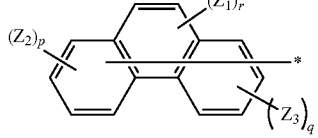

<Formula 2G>

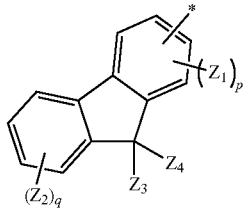

-continued

<Formula 2H>
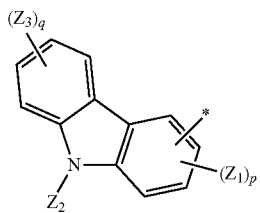

<Formula 2I>
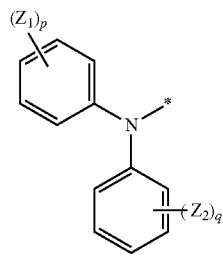

<Formula 2J>
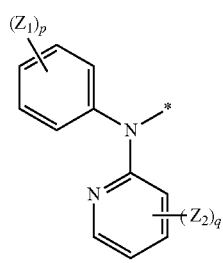

<Formula 2K>
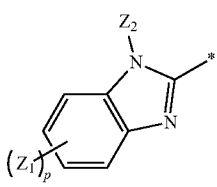

<Formula 2L>
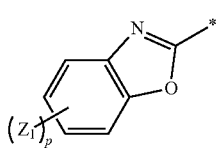

<Formula 2M>
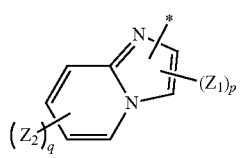

<Formula 2N>
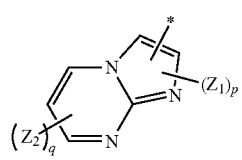

<Formula 2O>
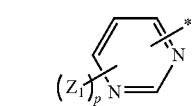

-continued

<Formula 2P>
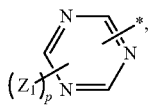

wherein $Z_1$, $Z_2$, $Z_3$, and $Z_4$ are each independently a hydrogen atom, a deuterium atom, a halogen atom, a hydroxyl group, a cyano group, a substituted or unsubstituted methyl group, a substituted or unsubstituted ethyl group, a substituted or unsubstituted propyl group, a substituted or unsubstituted butyl group, a substituted or unsubstituted methoxy group, a substituted or unsubstituted ethoxy group, a substituted or unsubstituted phenyl group, a substituted or unsubstituted naphthyl group, a substituted or unsubstituted anthryl group, and a substituted or unsubstituted quinolinyl group, or a substituted or unsubstituted pyridinyl group, a plurality of each of $Z_1$, $Z_2$, $Z_3$, and $Z_4$ are identical to or different from each other, p and q each are an integer of 1 to 5, r is 1 or 2, and * indicates a binding site, and $L_1$ is one of the groups manufactured according to Formulae 4A to 4H below:

<Formula 4A>
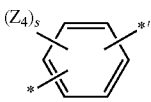

<Formula 4B>
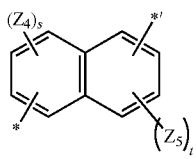

<Formula 4C>
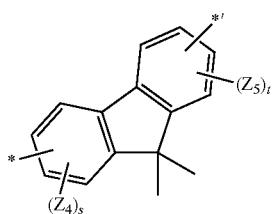

<Formula 4D>
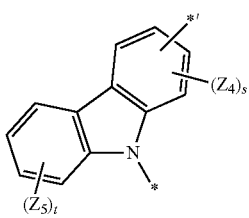

<Formula 4E>
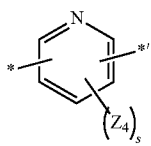

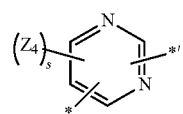
<Formula 4F>

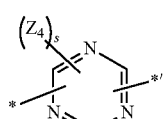
<Formula 4G>

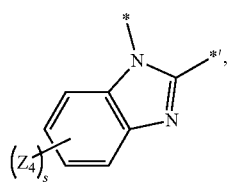
<Formula 4H> wherein $Z_4$ and $Z_5$ are each independently a hydrogen atom, a deuterium atom, halogen atom, a substituted or unsubstituted methyl group, a substituted or unsubstituted ethyl group, a substituted or unsubstituted propyl group, a substituted or unsubstituted butyl group, or a substituted or unsubstituted phenyl group, a plurality of each of $Z_4$ and $Z_5$ are identical to or different from each other, s and t is an integer of 1 to 4, *' indicates a binding site with the anthracene back bone, and * indicates a binding site with $R_3$.

10. The heterocyclic compound of claim 8, wherein $R_1$, $R_4$, and $R_6$ are each independently a hydrogen atom, a deuterium atom, halogen atom, a substituted or unsubstituted methyl group, a substituted or unsubstituted ethyl group, a substituted or unsubstituted propyl group, a substituted or unsubstituted tert-butyl group, or one of the groups represented by Formulae 3A to 3R below:

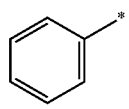
<Formula 3A>

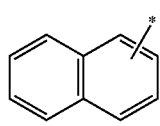
<Formula 3B>

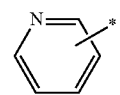
<Formula 3C>

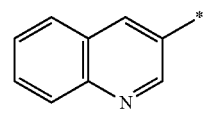
<Formula 3D>

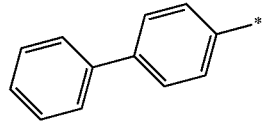
<Formula 3E>

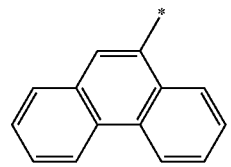
<Formula 3F>

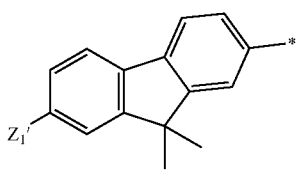
<Formula 3G>

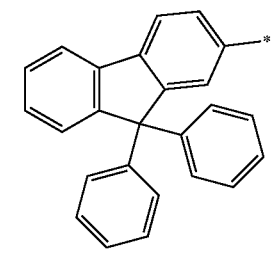
<Formula 3H>

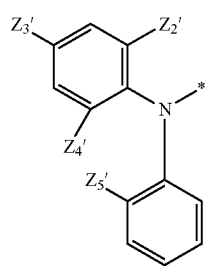
<Formula 3I>

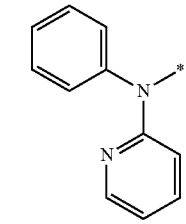
<Formula 3J>

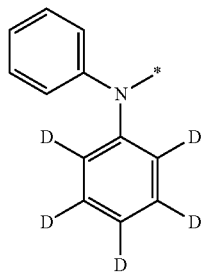
<Formula 3K>

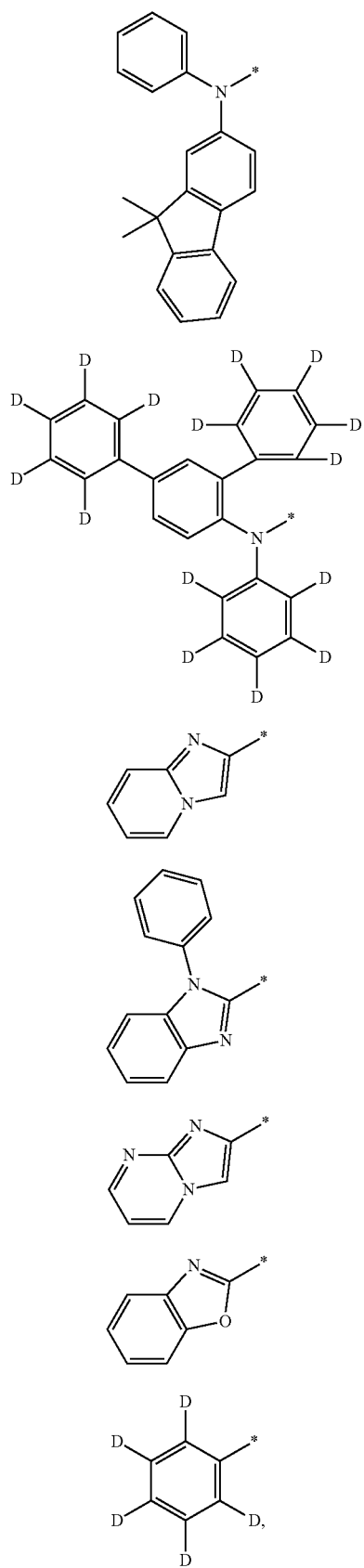

wherein

Z$_{1'}$ is a hydrogen atom or a phenyl group, Z$_{2'}$, Z$_{3'}$, Z$_{4'}$, and Z$_{5'}$ are each independently a hydrogen atom, a deuterium atom, a fluoro group, a methyl group, or a phenyl group, and a plurality of each of Z$_{2'}$, Z$_{3'}$, Z$_{4'}$, and Z$_{5'}$ are identical to or different from each other, and * indicates a binding site, and L$_1$ comprises one of the groups represented by Formulae 5A to 5I below:

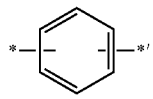
<Formula 5A>

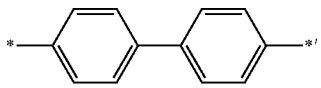
<Formula 5B>

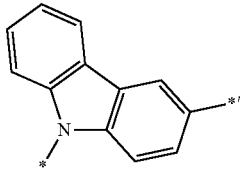
<Formula 5C>

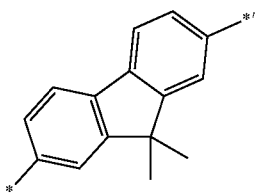
<Formula 5D>

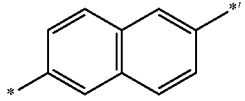
<Formula 5E>

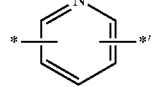
<Formula 5F>

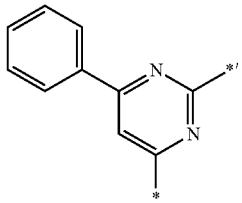
<Formula 5G>

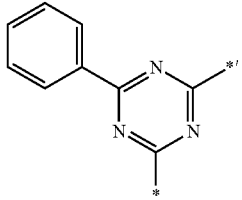
<Formula 5H>

<Formula 5I>
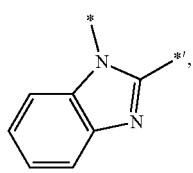
wherein *' indicates a binding site with the anthracene backbone, and * indicates a binding site with R₃.
11. The heterocyclic compound of claim 1, wherein the heterocyclic compound represented by Formula 1 is one of Compounds 1 to 80 below:
1
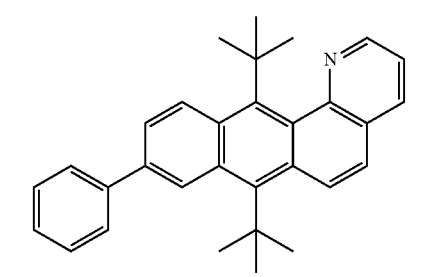
2
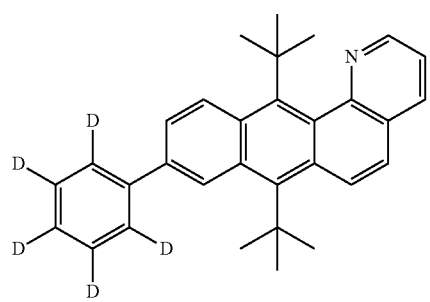
3
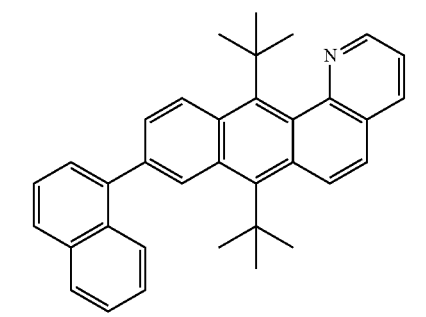
4
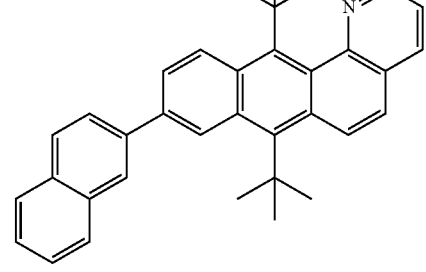
5
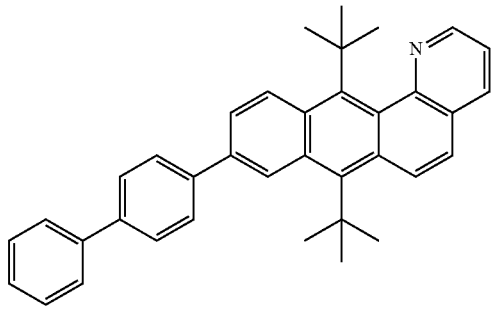
6
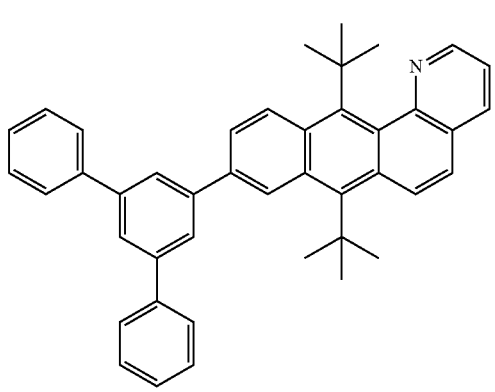
7
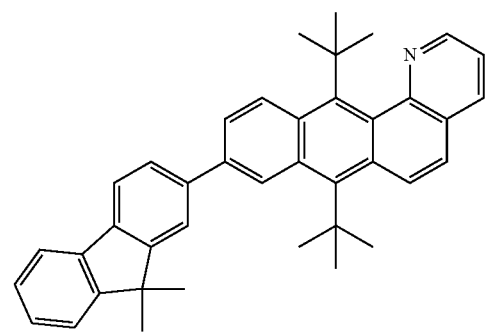
8
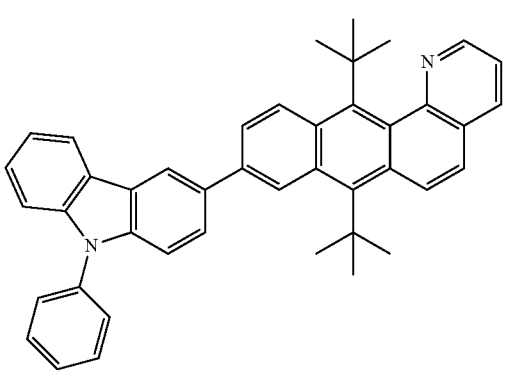

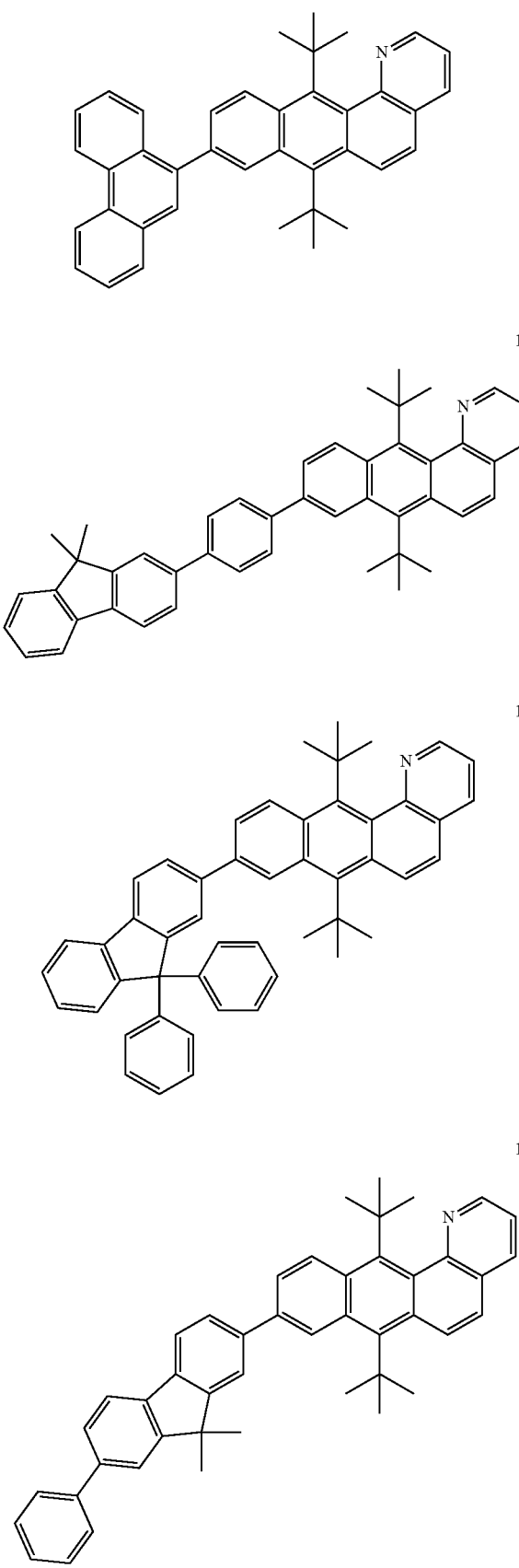
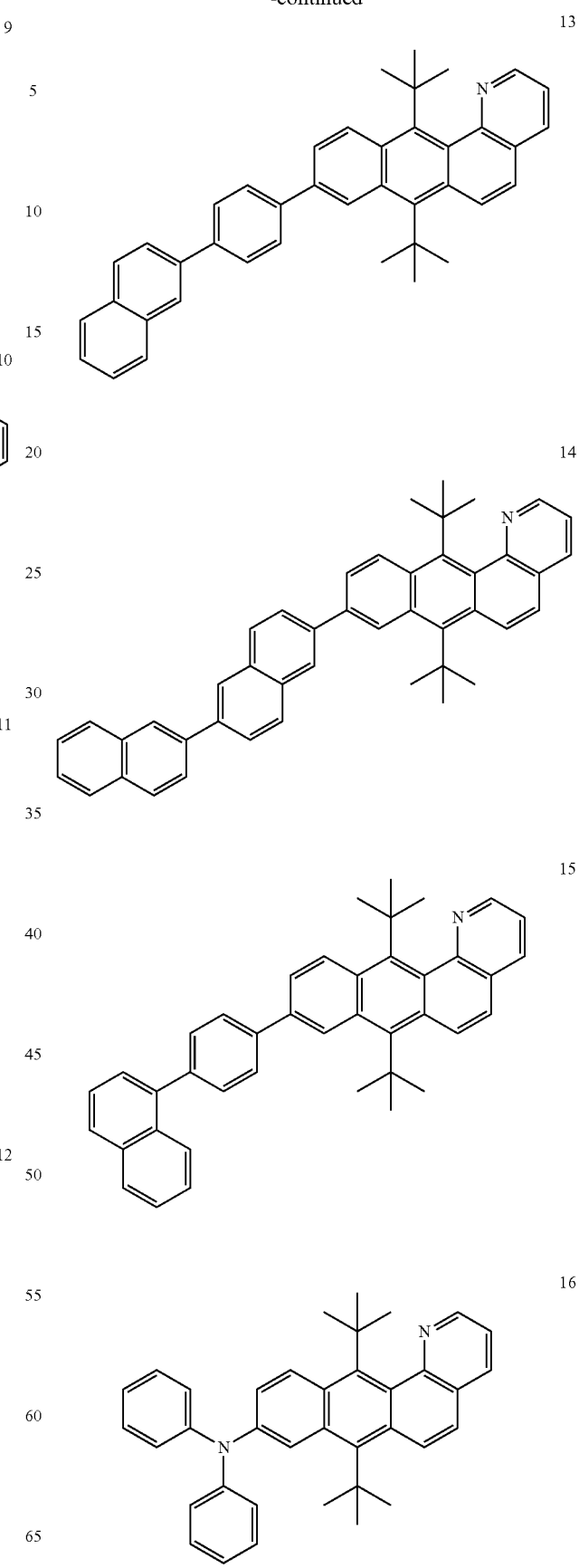

17
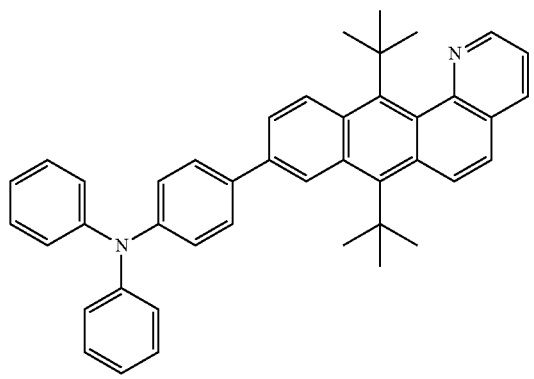
18
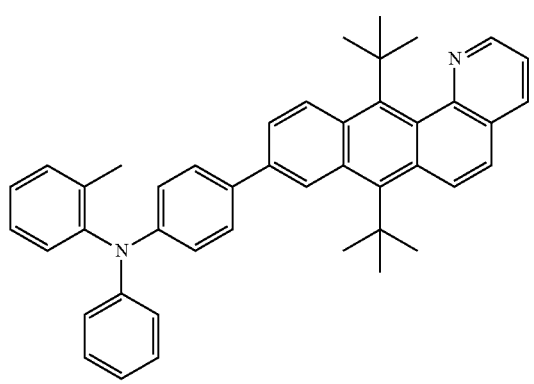
19
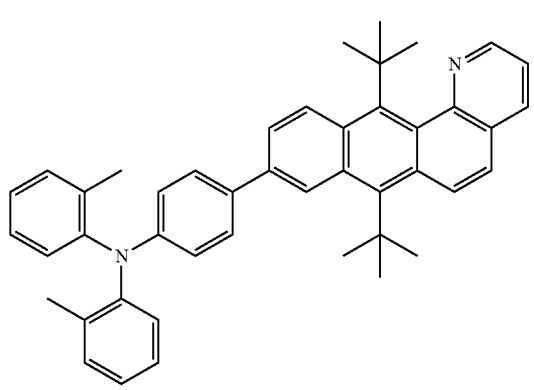
20
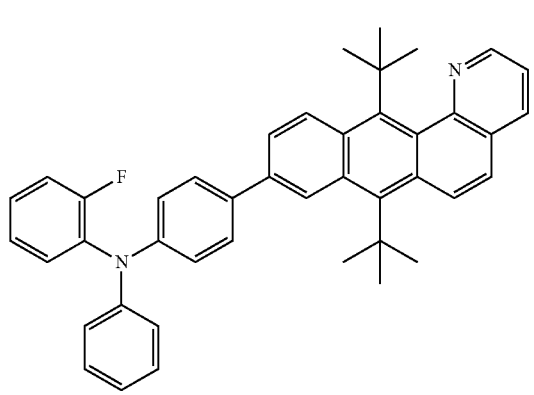
21
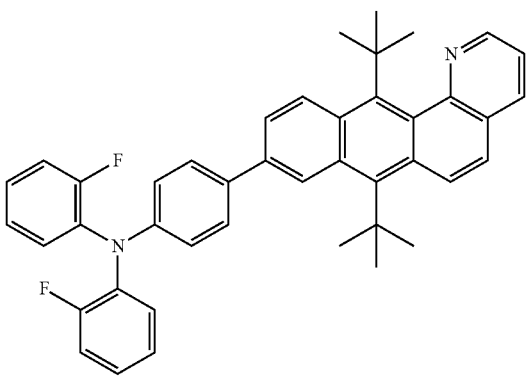
22
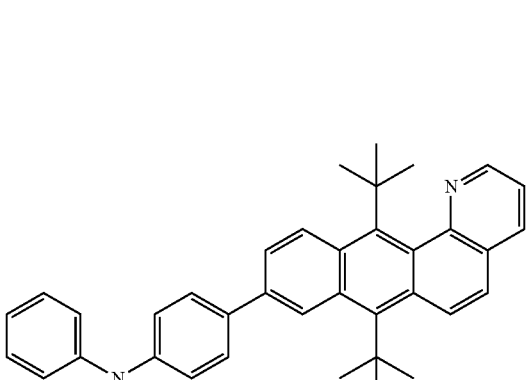
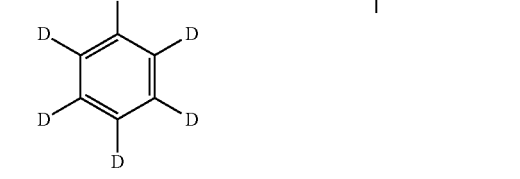
23
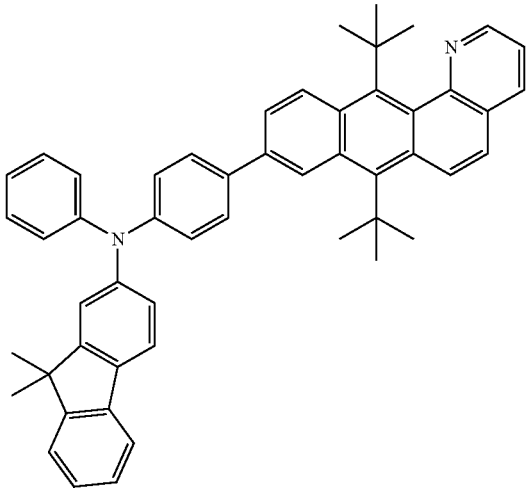

24
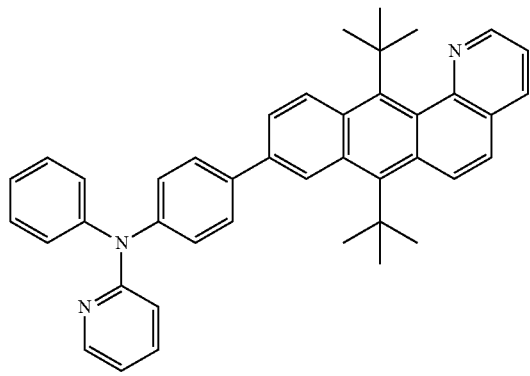
25
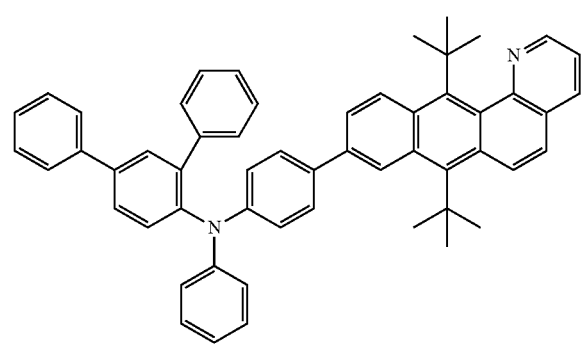
26
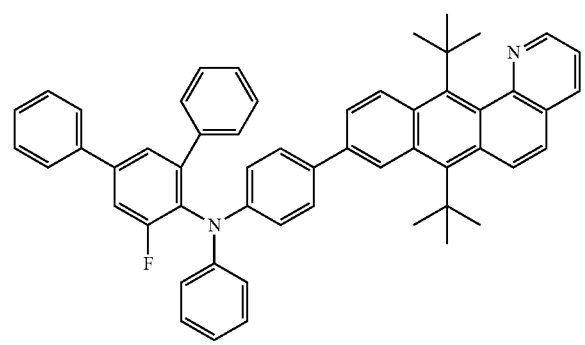
27
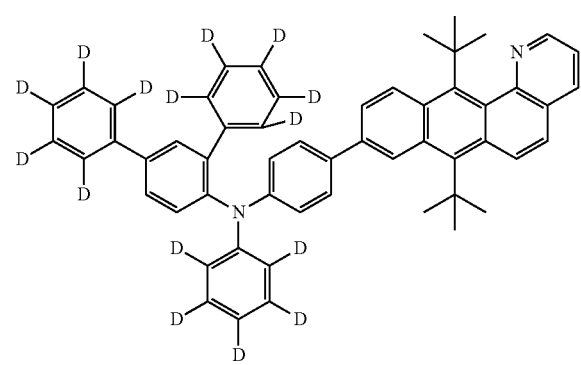
28
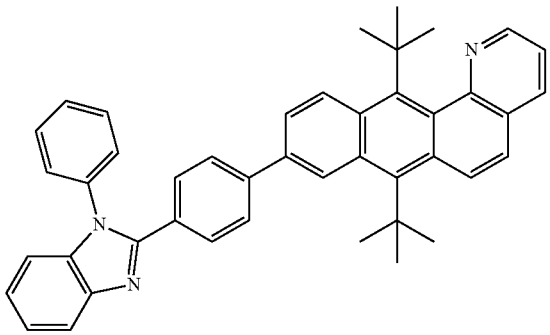
29
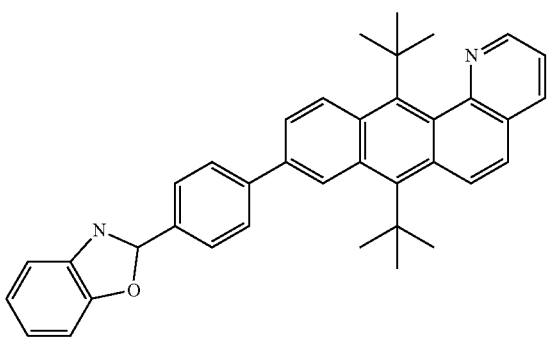
30
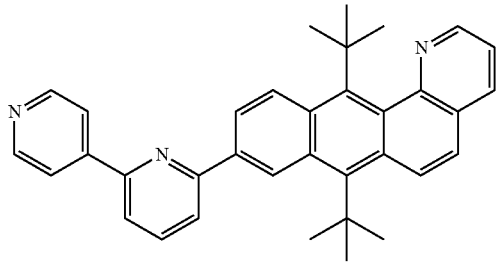
31
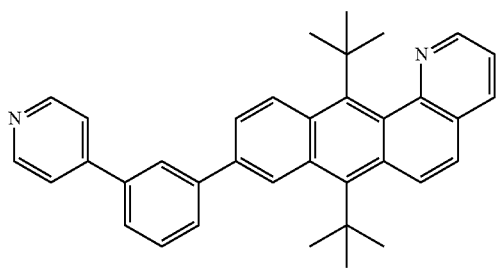
32
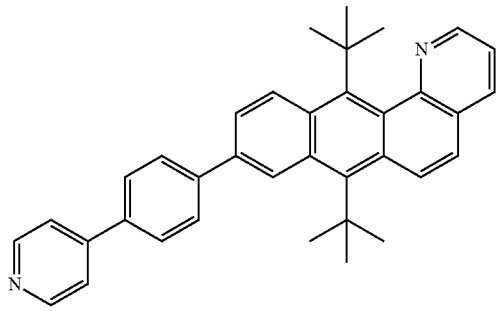

33
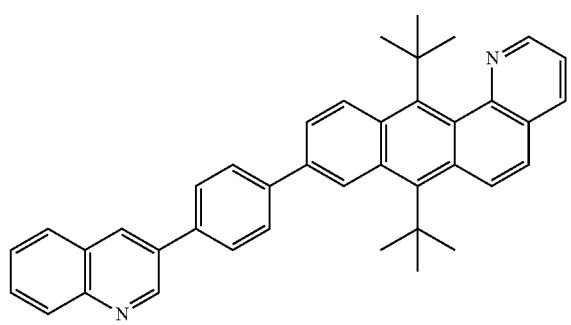
34
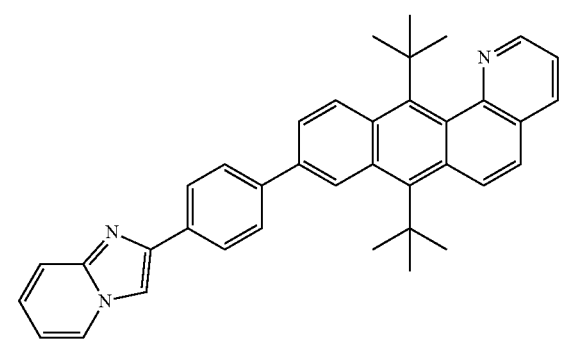
35
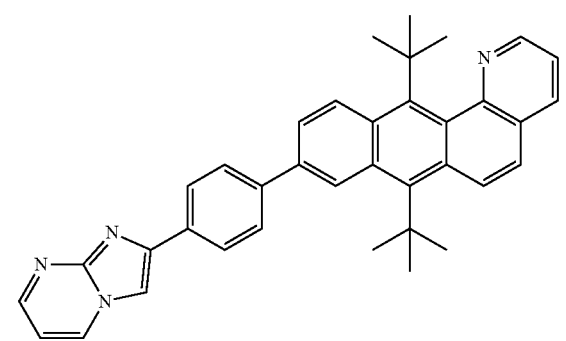
36
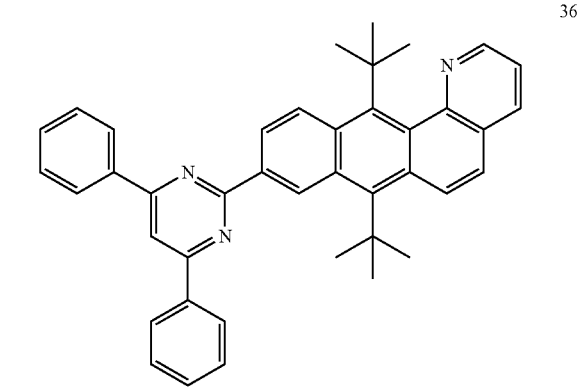
37
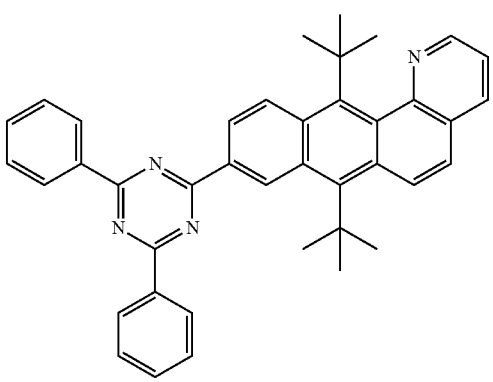
38
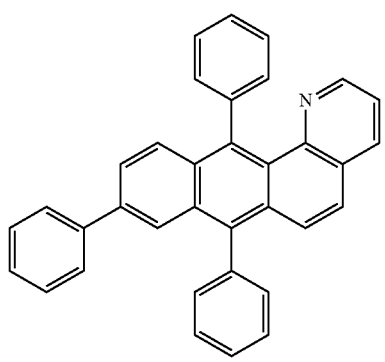
39
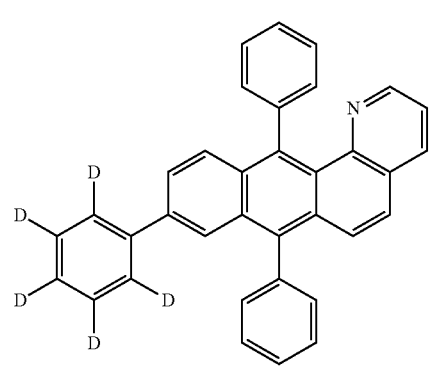
40
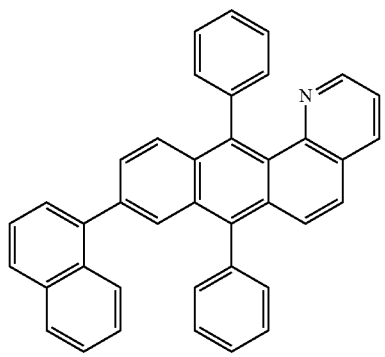

107
-continued
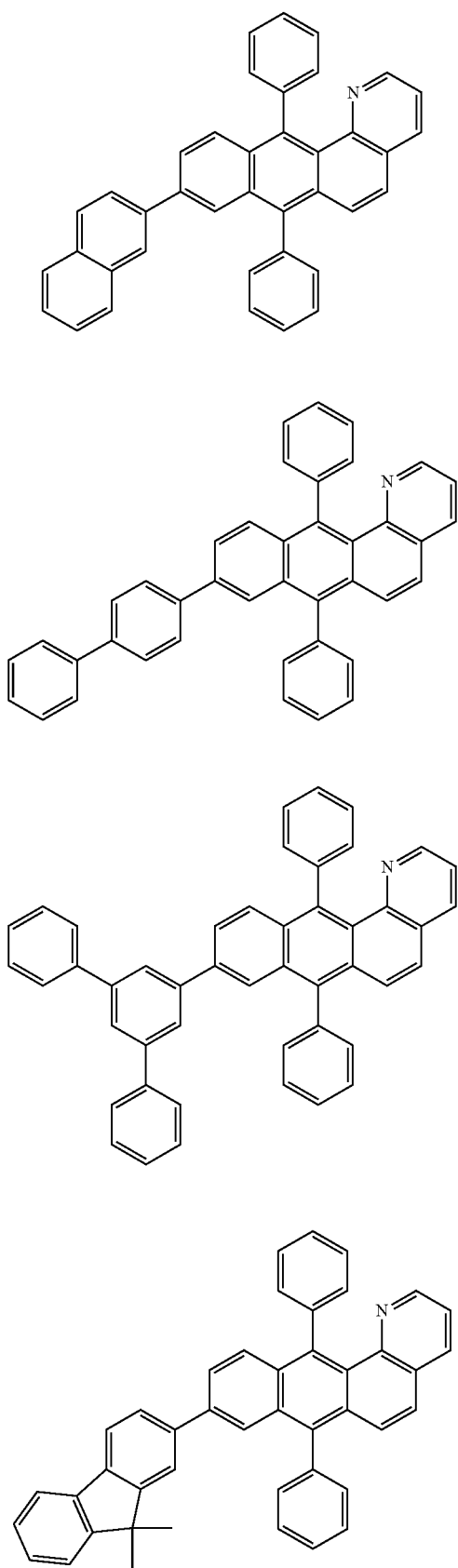
108
-continued
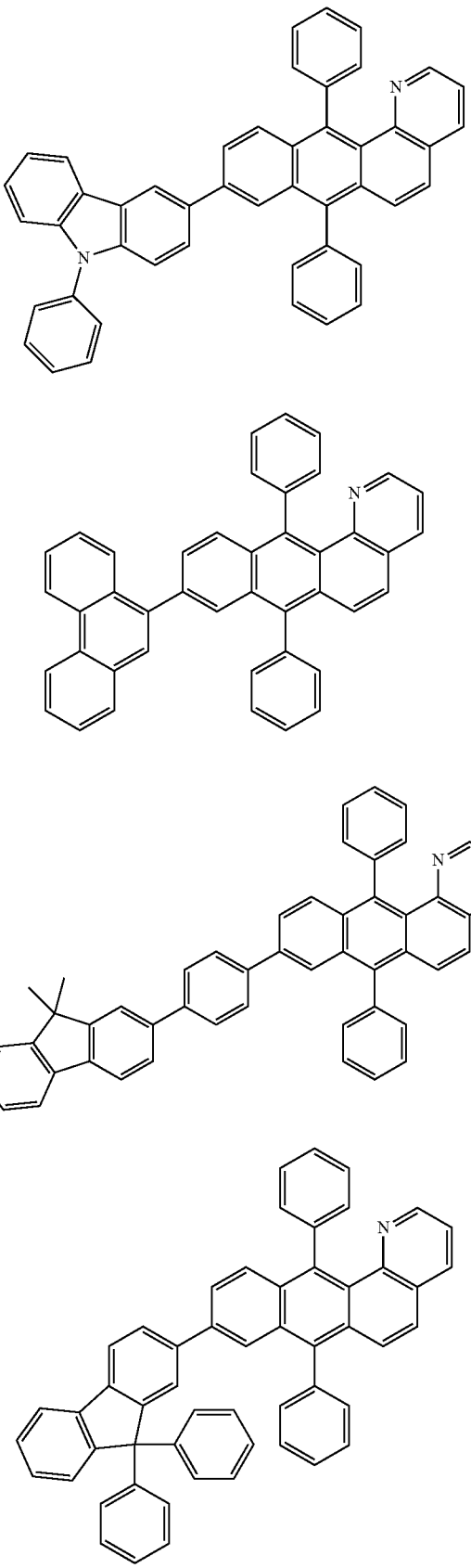

49
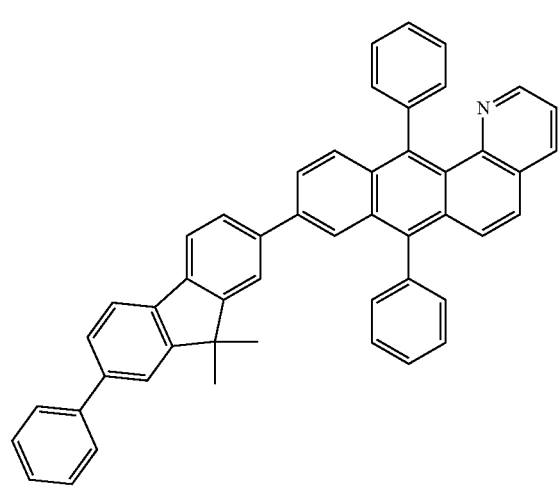
50
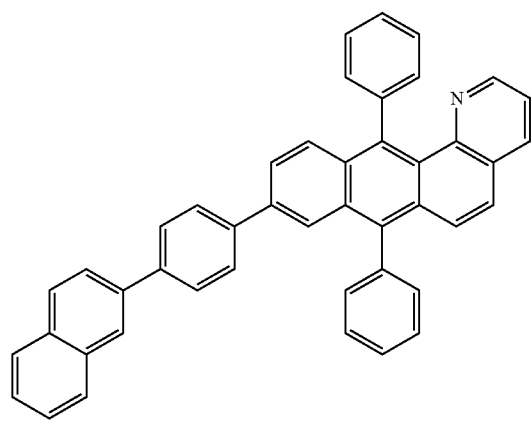
51
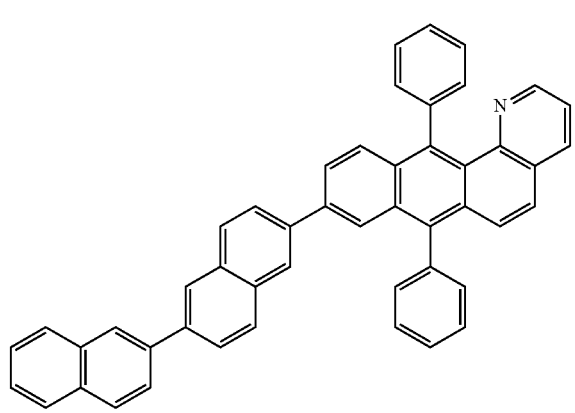
52
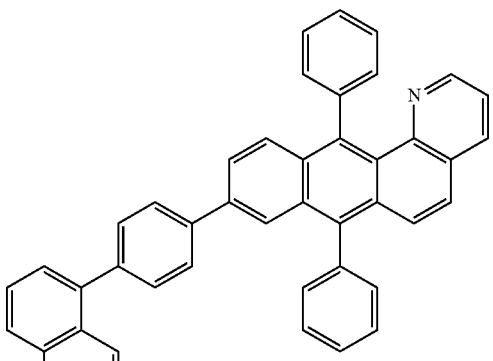
53
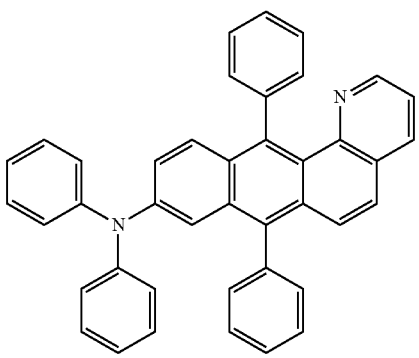
54
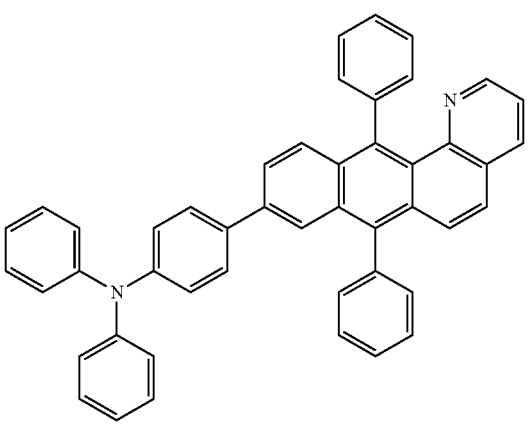
55
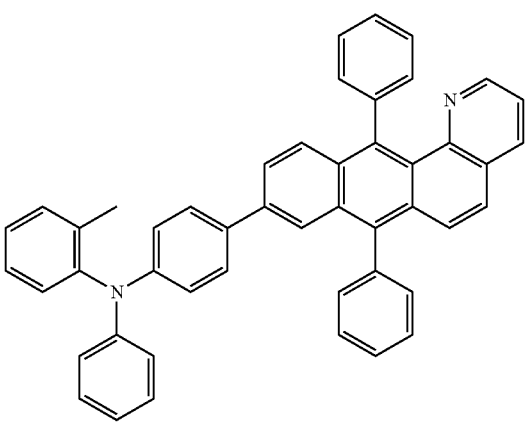

-continued
56
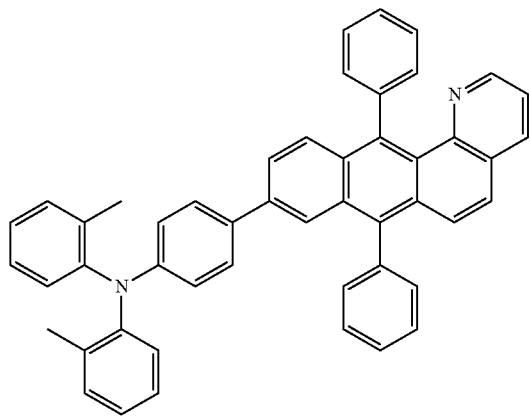
57
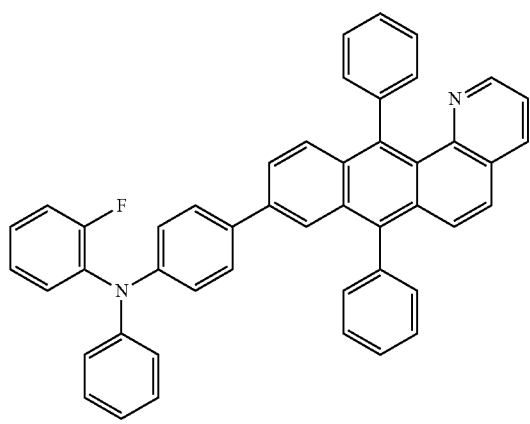
58
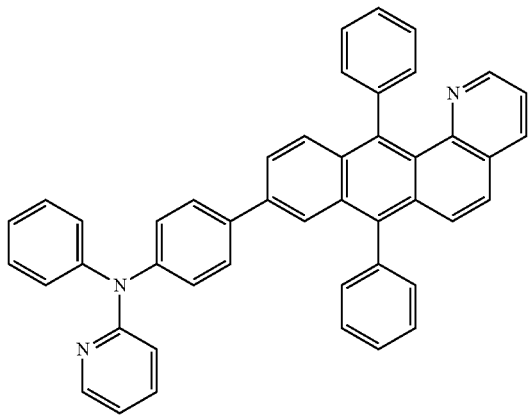
-continued
59
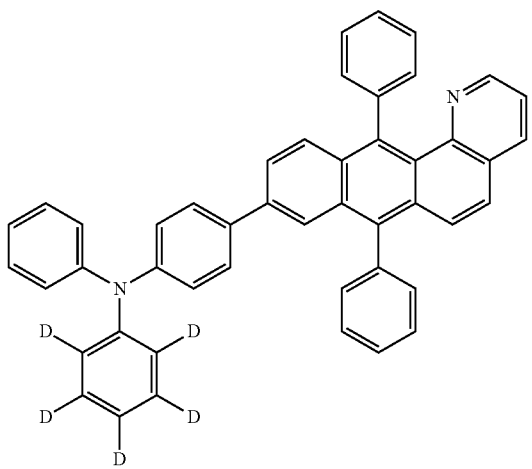
60
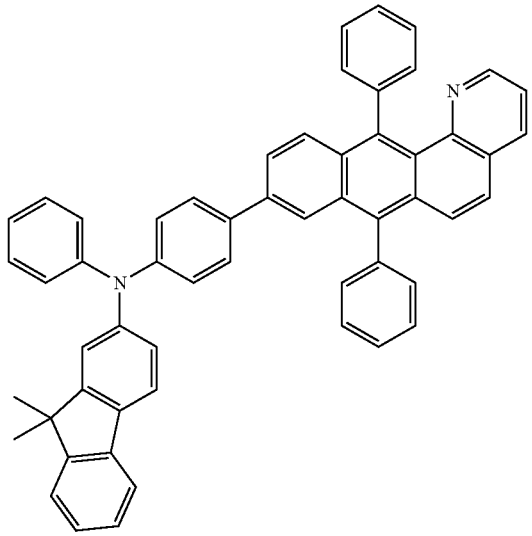
61

62
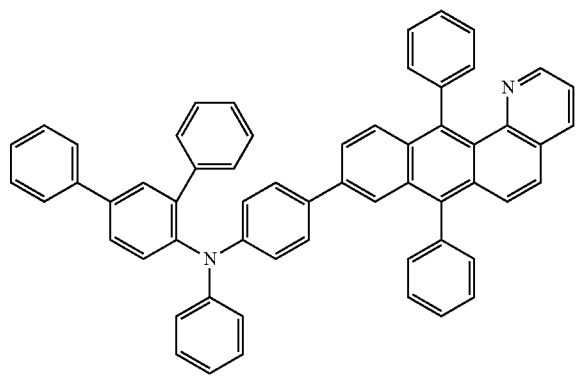
63
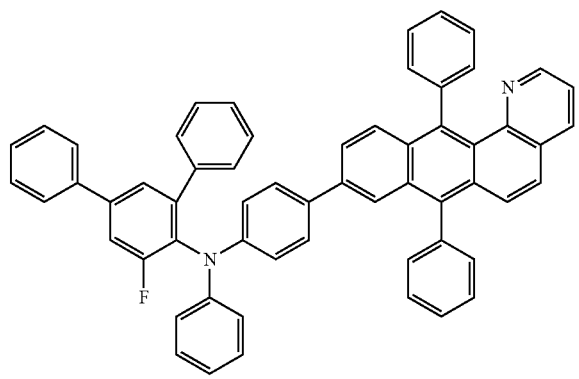
64
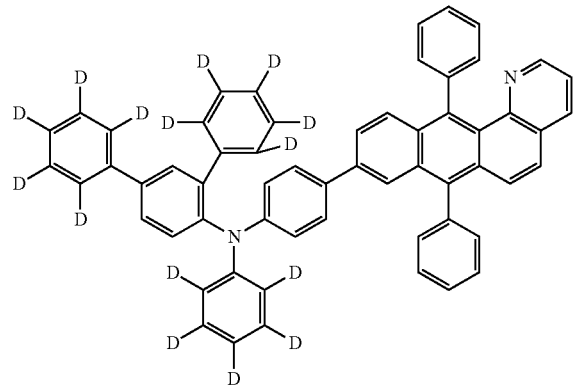
65
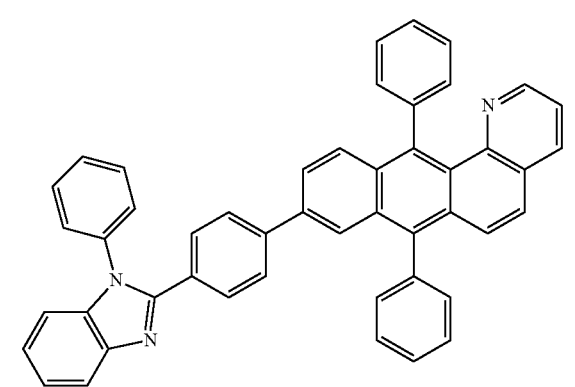
66
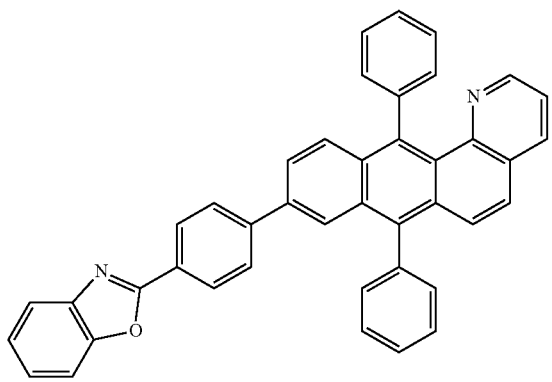
67
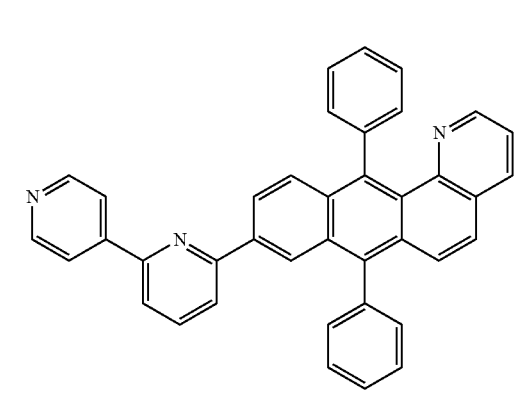
68
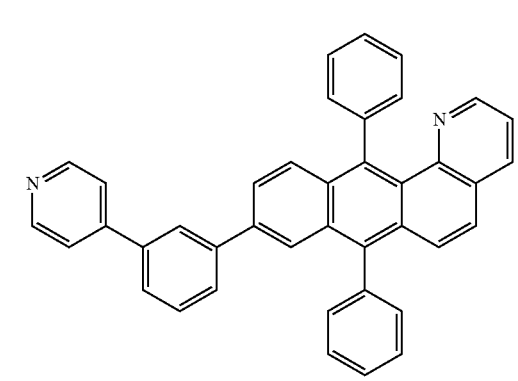
69
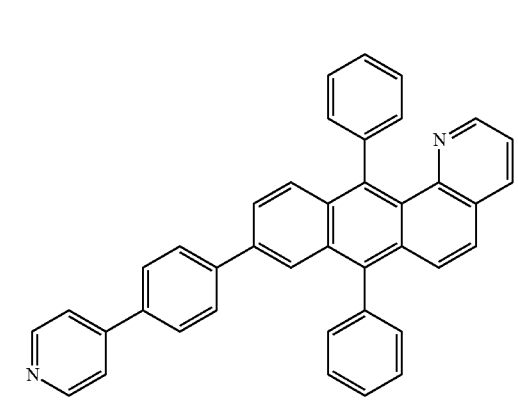

115
70
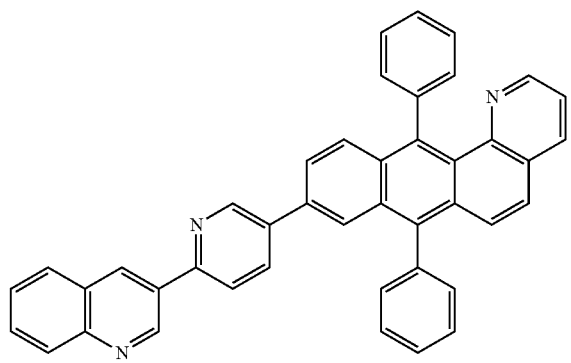
71
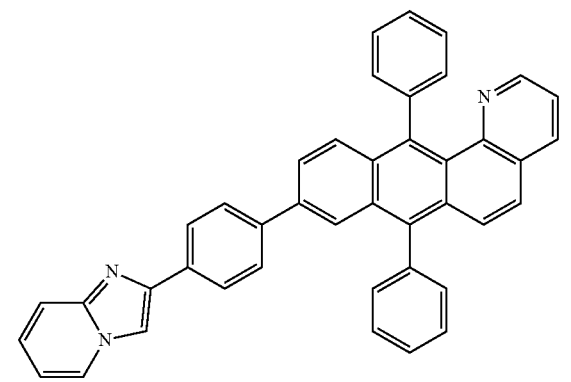
72
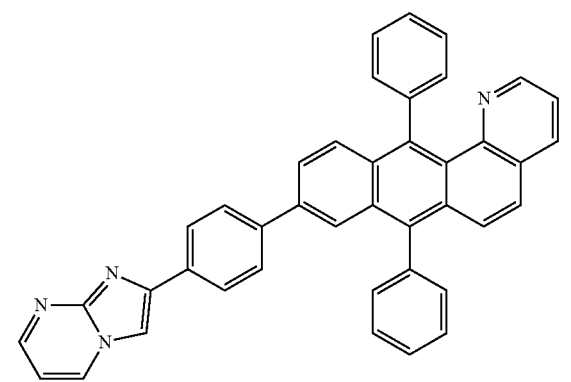
73
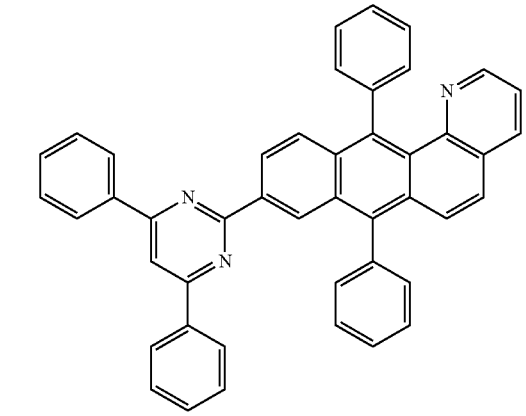
116
74
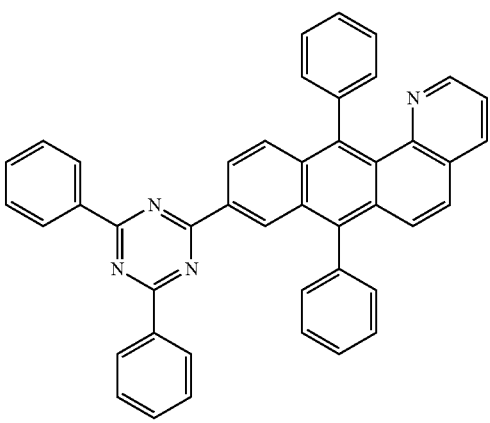
75
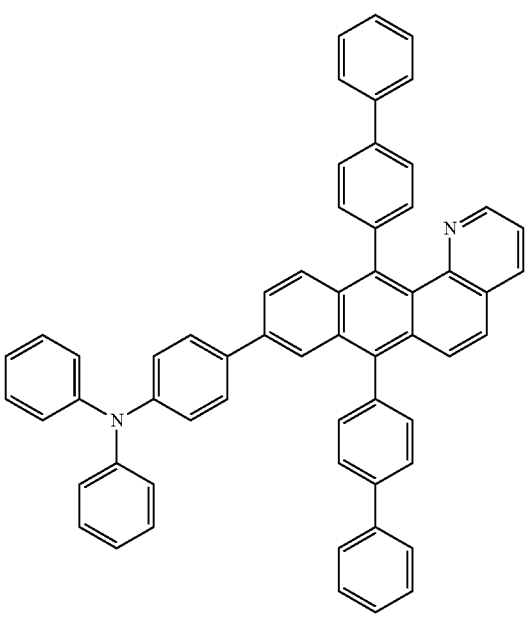
76
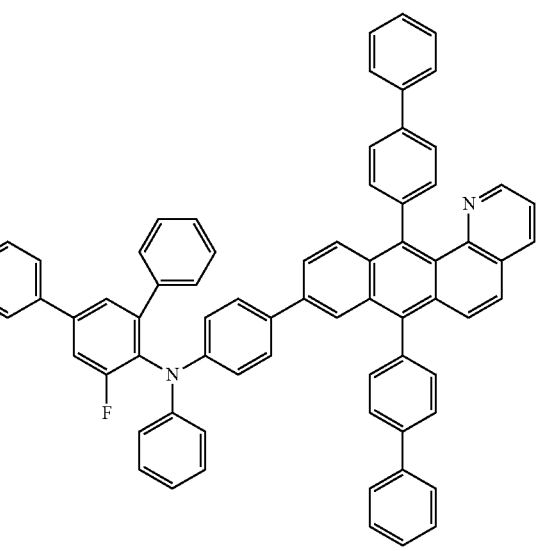

-continued

77

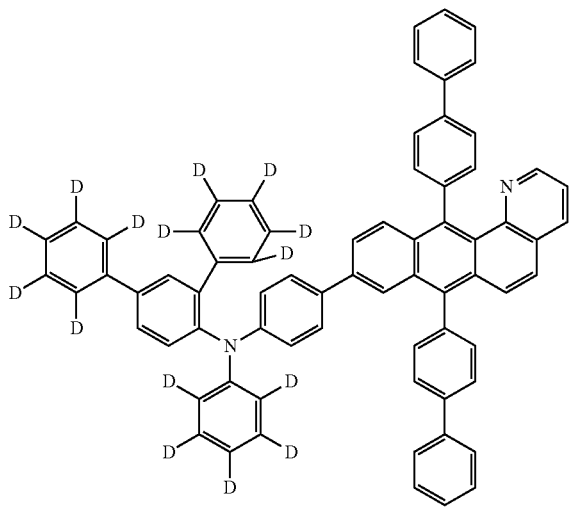

78

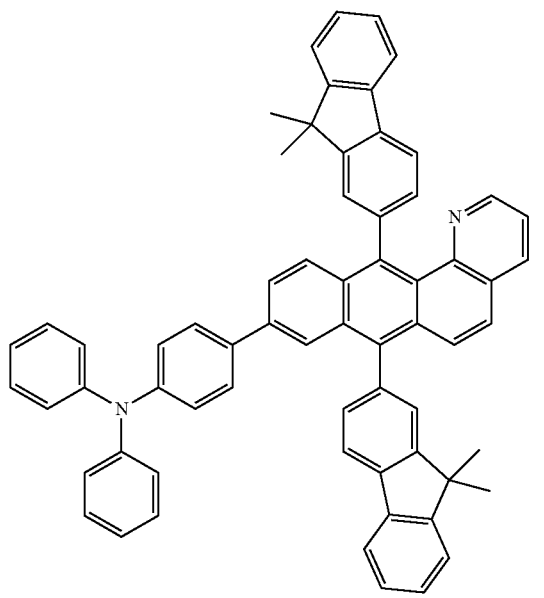

79

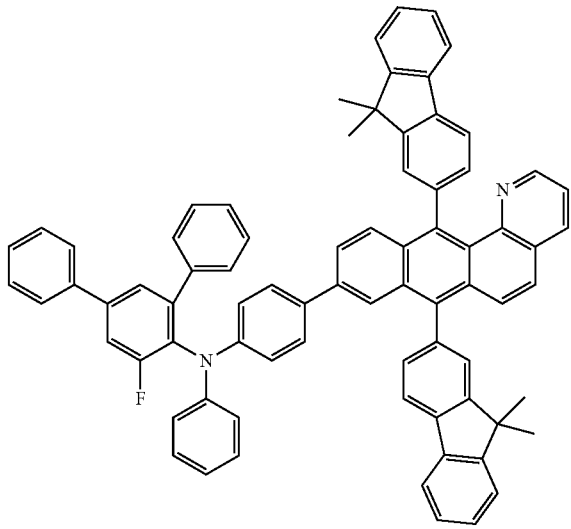

-continued

80

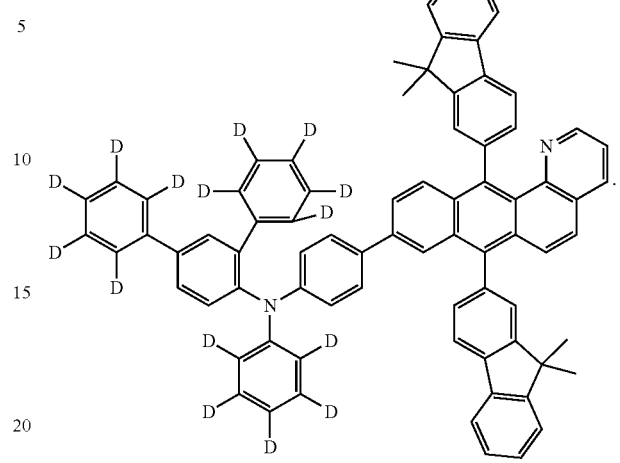

12. An organic light-emitting diode comprising:
a first electrode;
a second electrode facing the first electrode; and
a first layer interposed between the first electrode and the second electrode, wherein the first layer comprises the heterocyclic compound of claim 1.

13. The organic light-emitting diode of claim 12, wherein the first layer comprises at least one selected from the group consisting of an electron injection layer, an electron transport layer, a layer having an electron injection function and an electron transport function, and an emission layer.

14. The organic light-emitting diode of claim 13, wherein the first layer comprises an emission layer, and the heterocyclic compound is a fluorescent host, a phosphorescent host, or a fluorescent dopant in the emission layer.

15. The organic light-emitting diode of claim 13, wherein the first layer comprises an emission layer, and the emission layer further comprises an anthracene compound, an arylamine compound, or a styryl compound.

16. The organic light-emitting diode of claim 12, further comprising, between the first electrode and the second electrode, in addition to the first layer, a hole injection layer, a hole transport layer, a layer having a hole injection function and a hole transport function, an emission layer, a hole blocking layer, an electron injection layer, an electron transport layer, a layer having an electron injection function and an electron transport function, or a combination of two or more thereof.

17. The organic light-emitting diode of claim 16, wherein the layer in addition to the first layer comprises an emission layer, and the emission layer comprises a host and a dopant, and the dopant is a fluorescent dopant or a phosphorescent dopant.

18. The organic light-emitting diode of claim 16, wherein the layer in addition to the first layer comprises an emission layer, and the emission layer further comprises an anthracene compound, an arylamine compound, or a styryl compound.

19. The organic light-emitting diode of claim 12, wherein the first layer comprises an electron transport layer, and the electron transport layer comprises a heterocyclic compound and a metal-containing material.

20. The organic light-emitting diode of claim 12, wherein at least one layer selected from the group consisting of the first layer and the layer in addition to the first layer is formed by using a wet process.

21. A flat display device comprising:
a transistor comprising a source, a drain, a gate, and an active layer; and
the organic light-emitting diode of claim 12,
wherein one of the source and the drain is electrically connected to the first electrode of the organic light-emitting diode.

22. A heterocyclic compound represented by Formula 1 below:

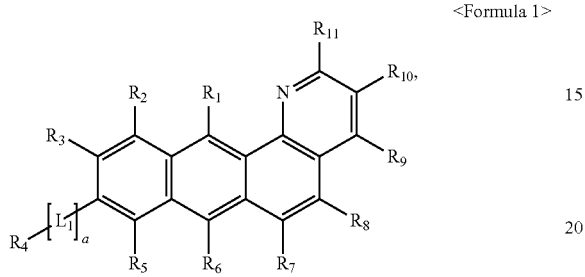

<Formula 1> wherein
$R_1$ to $R_{11}$ are each independently a hydrogen atom, a deuterium atom, a halogen atom, a hydroxyl group, a cyano group, a nitro group, a carboxyl group, a substituted or unsubstituted $C_1$-$C_{30}$ alkyl group, a substituted or unsubstituted $C_2$-$C_{30}$ alkenyl group, a substituted or unsubstituted $C_2$-$C_{30}$ alkynyl group, a substituted or unsubstituted $C_1$-$C_{30}$ alkoxy group, a substituted or unsubstituted $C_3$-$C_{30}$ cycloalkyl group, a substituted or unsubstituted $C_3$-$C_{30}$ cycloalkenyl group, a substituted or unsubstituted $C_6$-$C_{30}$ aryl group, a substituted or unsubstituted $C_2$-$C_{30}$ heteroaryl group, a substituted or unsubstituted $C_6$-$C_{30}$ aryloxy group, a substituted or unsubstituted $C_6$-$C_{30}$ arylthio group, or a group represented by $N(Q_1)(Q_2)$ where $Q_1$ and $Q_2$ are each independently a hydrogen atom, a deuterium atom, a substituted or unsubstituted methyl group, a substituted or unsubstituted ethyl group, a substituted or unsubstituted propyl group, a substituted or unsubstituted butyl group, a substituted or unsubstituted pentyl group, a substituted or unsubstituted phenyl group, a substituted or unsubstituted pyridinyl group, a substituted or unsubstituted naphthyl group, a substituted or unsubstituted anthryl group, a substituted or unsubstituted fluorenyl group, a substituted or unsubstituted carbazolyl group, or a substituted or unsubstituted pyrimidinyl group, provided that $R_{11}$ is not a phenyl, and $L_1$ is a substituted or unsubstituted $C_6$-$C_{30}$ arylene group, or a substituted or unsubstituted $C_3$-$C_{30}$ heteroarylene group, and a is an integer of 1 or 2, wherein if a is 2, two $L_1$ are identical to or different from each other.

23. The heterocyclic compound of claim 1, wherein $R_{11}$ is a hydrogen atom.

* * * * *